United States Patent [19]

Bierer

[11] Patent Number: 5,681,958

[45] Date of Patent: Oct. 28, 1997

[54] CRYPTOLEPINE ANALOGS WITH HYPOGLYCEMIC ACTIVITY

[75] Inventor: Donald E. Bierer, Daly City, Calif.

[73] Assignee: Shaman Pharmaceuticals, Inc., South San Francisco, Calif.

[21] Appl. No.: 484,424

[22] Filed: Jun. 7, 1995

[51] Int. Cl.$^6$ .................................................. C07D 519/00
[52] U.S. Cl. .................... 546/70; 546/61; 546/62
[58] Field of Search ........................... 514/284, 285; 546/61, 62, 70

[56] References Cited

U.S. PATENT DOCUMENTS

| | | | |
|---|---|---|---|
| 3,374,264 | 3/1968 | Uskokovic et al. | |
| 4,826,850 | 5/1989 | Yamato | |
| 4,841,063 | 6/1989 | Virgilio et al. | 548/213 |
| 5,070,088 | 12/1991 | Atwal | 514/212 |
| 5,223,506 | 6/1993 | Luzzio et al. | 514/279 |
| 5,428,040 | 6/1995 | Magolda et al. | 514/284 |

FOREIGN PATENT DOCUMENTS

| | | |
|---|---|---|
| 0 376 166 A1 | 7/1990 | European Pat. Off. |
| 132752 | 11/1978 | German Dem. Rep. |
| 5-306284 | 11/1993 | Japan |
| WO 94/18203 | 8/1994 | WIPO |

OTHER PUBLICATIONS

Ablordeppey et al., 1990, "$^1$H-NMR and $^{13}$C-NMR Assignments of cryptolepine, A 3:4-benz-δ-carboline derivative isolated from *Cryptolepis sanguinolentai*", Planta Medica 56:416–417.

Anon, 1982, "Cryptolepine hydrochloride", Drugs of the Future 7:466.

Armit and Robinson, 1922, "Polynuclear heterocyclic aromatic types. Part I. Some indenoquinoline derivatives", J Chem Soc pp. 827–839.

Baldwin and Magnus (eds.), 1994, in *Organic Synthesis Based on Name Reactions and Unnamed Reactions*, vol. 11, pp. 36.

Bamgbose and Noamesi, 1981, "Studies on Cryptolepine", Planta Medica 41:392–396.

Blount et al., 1929, "Stereoisomerism in polycyclic systems. Part VI", J Chem Soc 1975–1987.

Boakye-Yiadom and Heman-Ackah, 1979, "Cryptolepine hydrochloride effect on *Staphylococcus aureus*", J Pharm Sci 68(12):1510–1514.

Chang et al., 1992, "Synthesis of 7-substituted indolo[3,2-b]-quinoline derivatives", Heterocycle 33(1):147–152.

Cimanga et al., 1991, "Biological Activities of Cryptolepine, An Alkaloid from *Cryptolepis sanguinolenta*", Planta Medica 57 Supp. 2 A98–A99.

Clinquart et al., 1929, "Sur la compestion chimique de *Cryptolepis triangularis* plante congolaise", Bull. Acad. R. Med. Belg. 12:627–635.

Degutis and Ezyarskaite, 1986, "Alkylation of quindoline and quindoline-11-carboxyic acid", Khimiya Geterotsiklicheskikh Soedinenii 10:1375–1379.

Desearbre and Merour, 1994, "Synthesis and reactivity of 1-substituted-3H-pyrrolo[2,3-b] pyridin-3-one", Tetrahedrom Letters 35(13):1995–1998.

Dwuma-Badu et al., 1978, "Constituents of West African medicinal plants XX: Quindoline from *Cryptolepis sanguinolenta*", J Pharm Sci 67(3):433–434.

Ezyarskaite, 1989, "On the synthesis of 7-bromoquindoline derivatives", Izv Khim 22:101–105.

Fichter and Boehreinger, 1906, "*Ueber chindolin*", Diese Berichte 3932–3942.

Fichter and Rohner, 1910, "Uber einige derivate des chindolins", Chem Ber 43:3489–3499.

Fichter and Probst, 1907, "Zur kenntnis des methyl-chindolanols", Diese Berichte 40:3478.

Galun et al., 1979, "Derivatives of Indole-3-oxyacetic acid", J Heterocyclic Chem 16:641–643.

Gellért et al., 1951, "Die konstitution des alkaloids cryptolepin", Helvetica Chimica Acta 34:642–651.

Giraud, 1879, "Sur quelques dérivés de l'indigotine", Comptes Rendus pp. 104–105.

Giraud, 1880, "Préparation de l'indoline et de ses composés", Comptes Rendus pp. 1429–1430.

Görlitzer and Weber, 1981, "Hemmung der thrombocytenaggregation dutch anellierte chinoline mit 3-dimethylaminopropylmercapto-substituenten", Arch Phar 315:532–537.

Görlitzer et al., 1994, "Anti-malaria active 10H-indolo[3,2-b]quinoline-11-yl-amines. Part I. Phenil-Mannich-bases of the amodiaquine and cycloquine type", Pharmazie 49:231–235.

Görlitzer and Weber, 1981, "10-hydroxy-10H-indolo[3,2-b]chinolin-5-oxid ('Dioxychindolin')", Arch Pharm 314:850–852.

Görlitzer and Weber, 1981, "10H-indolo[3,2-b]chinolin", Arch Pharm 314:852–861.

Görlitzer et al., 1995, "Gegen malaria wirksame 10H-indolo[3,2-b]chinolin-11-yl-amine", Pharmazie 50:105–111.

Görlitzer, 1976, "Untersuchungen an 1,3-dicarbonylverbindungen, 6. Mitt. Anerllierte Chinolone", Arch Pharm 309:18–25.

Görlitzer and Weber, 1980, "11-oxo-5,11 -dihydro-benzothieno[3,2-B][1] chinoline, s,s-dioxide und thionierungsprodukte", Arch Pharm 314:76–84.

Görlitzer and Weber, 1980, "Anellierte chinoline III), 11-oxo-5,11-dihydro-benzothieno-[3,2-b][1] chinoline", Arch Pharm 313:27–34.

Görlitzer, 1979, "Anellierte chinolone II, N- und O-alkylierungs produkte", Arch Pharm 312:254–261.

(List continued on next page.)

Primary Examiner—C. Warren Ivy
Assistant Examiner—Garth M. Dahlen
Attorney, Agent, or Firm—Pennie & Edmonds LLP

[57] ABSTRACT

Novel cryptolepine analogs useful as hypoglycemic agents and methods for their use as hypoglycemic agents, for example, in the treatment of diabetes, and a method for their synthesis are described. As hypoglycemic agents, the novel crytolepine analogs are useful for the treatment of insulindependent diabetes mellitus (IDDM or Type I) and non-insulin dependent diabetes mellitus (NIDDM or Type II).

13 Claims, 9 Drawing Sheets

OTHER PUBLICATIONS

Gunatilaka et al., 1980, "Studies on the medicinal plants of Sri Lanka", Planta Medica 39:66–72.

Holt and Petrow, 1948, "Carbazoles, carbolines, and related compounds. Part II. Transformations of some quarternary salts of quindoline", pp. 919–922.

Holt and Petrow, 1947, "Carbazoles, carbolines, and related compounds. Part I. Quindoline derivatives", pp. 607–611.

Holt and Petrow, 1948, "Carbazoles, carbolines, and related compounds. Part III. Quinindoline derivatives", pp. 922–924.

Jezerskaite et al., 1989, "New heterocyclic sensitizers for electrophotography", Izv Khim 22:113–121.

Kempter et al., 1963, Z Chem 3:352–353.

Merour et al., 1982, "Syntheses of 2(5)-substituted 1-acetyl-3-oxo-2,3-dihydroindoles, 3-acetoxy-1-acetylindoles, and of 2-methyl-5-methoxyindole-3-acetic acid", Synthesis 12: 1053–1056.

Mooradian et al., 1949, "'A new series of testosterone esters", J Amer Chem Soc 71:3372–3374.

Nenitzescu and Raileanu, 1958, "Synthesen des heteroauxins, des tryptamins und des serotonins", Chem Ber 91:1141–1145.

Oyekan, 1994, "Role of the Endothelium and Cyclic GMP in Renal Vasodilator Responses to Cryptolepine in Rats", J. Cardiovasc. Pharmacol. 23:602–611.

Ossman et al., 1988, "Synthesis of 2-cyanomethyl-3, 1-benzoxazin-4(H)-one", Egypt J Chem 31 (3):381–385.

Oyekan and Ablordeppey, 1993, "The mechanism(s) of the antiaggregatory effects of cryptolepine: The role of cyclic adenosine monophosphate and cellular $Ca^{2+}$", Gen Pharmacol 24(2):461–469.

Oyekan and Ablordeppey, 1993, "Effects of cryptolepine on collagen-induced aggregation and on the mobilization and metabolism of arachidonic acid by rabbit platelets", Gert Pharmacol 24(5):1285–1290.

Oyekan and Okafor, 1989, "Effects of cryptolepine alone and in combination with dipyridamole on a mouse model of arterial thrombosis", J Ethnopharmacol 27:141–148.

Paulo et al., 1994, "In vitro antibacterial screening of Cryptolepis sanguinolenta alkaloids", J Ethnopharmacol 44:127–130.

Potential Antimalarial in Ghanian Plant, IMS Pharmaceutical Marketletter, May 7, 1984, p., 13.

Proceeding from the First International Seminar on Cryptolepine at the University of Science and Technology Kumasi, July 27–30 1983, Boakye–Yiadom and Bamgbose (eds.), pp.1–82.

Rauwald et al., 1992, "Cryptolepis sanguinolenta:Antimuscarinic Properties of Cryptolepine and the Alkaloid Fraction at M1, M2 and M3 Receptors," Planta Medica, 58:486–488.

Raymond–Hamet et al., 1938, "Pharmacologie—Sur les Effects Hypotenseurs et Vaso–dilatateurs de la Cryptolepine", C.R. Acad. Sci. 207:1015–1018.

Raymond–Hamet et al., 1937, "Sur Quelques Proprietes Physiologiques des Alcaloides du Crytloepis sanguinolenta Schlechter", C.R. Soc. Biol. 126:768–770.

Schoen and Bogdanowicz–Szwed, 1964, "The reaction of α–indanone anils with phenylisocyanate. Anilides of 1-arylamino–indene-2-carboxylic acids", Roczniki Chemii Ann Soc Chim Polonorum 38:425–435.

Schulte et al., 1971, "Kondensierte indole aus 2-chlorindoaldehyd-(3)", Arch Pharmaz 305:523–533.

Schutzenberger, 1877, "Note sur un nouveau dérivé de l'indigotine", Comptes Rendus pp. 147–149.

Sevodin et al., 1984, "New method of synthesis of quindolines from 1,5–diketones of the indoline series", Chem Heterocyclic Comp 20(12):1374–131380.

Sevodin et al., 1982, "New methods for the synthesis of quindolines on the basis of 1,5–diketones of the indolinone series", Chem Heterocyclic Compounds 18(8):865.

Spitzer et al., 1991, "Total assignment of the proton and carbon NMR spectra of the alkaloid quindoline—Utilization of HMQC–TOCSY to indirectly establish protonated carbon–protonated carbon connectivities", J Heterocyclic Chem 28:2065–2070.

Sunder and Peet, 1978, "Synthesis of benzofuro[3,2-b] quinolin–6(11H) one and derivatives", J Heterocyclic Chem 15:1379–1382.

Tackie et al., 1991, "Assignment of the proton and carbon NMR spectra of the indoloquinoline alkaloid cryptolepine", J Heterocyclic Chem 28:1429–1435.

Takeuchi et al., 1992, "Synthesis and antitumor activity of fused quinoline derivatives. III. Novel N-glycosylamino–indolo[3,2–b]quinolines", Chem Pharm Bull 40(6):1481–1485.

Takeuchi et al., 1991, "Synthesis and antitumor activity of 7–(N–glycosylamino)–indolo[3,2–b]quinolines", Chem Pharm Bull 39(6):1629–1631.

Yamato et al., 1990, "Synthesis and antitumor activity of fused quinoline derivatives", Chem Pharm Bull 38(11):3048–3052.

Yamato et al., 1989, "Synthesis and antitumor activity of fused tetracyclic quinoline derivatives", J Med Chem 32:1295–1300.

Yamato et al., 1992, "Synthesis and antitumor activity of fused quinoline derivatives. II. Novel 4–and 7–hydroxyindolo[3,2–b]quinolines", Chem Pharm Bull 40(2):528–530.

Noamesi et al., 1980, "The alpha–adrenoceptor blocking properties of cryptolepine on the rat isolated vas deferens", Planta Medica 39:51–56.

Mutschler E. et al, Drug Actions: Basic Principles and Therapeutic Aspects, 1995, pages 271–279.

Cromwell, N.H. et al, J. Heterocycl. Chem. 1979, 16, pp. 699–704.

Beisler, J.A., J. Med. Chem. 1971, 14(11), pp. 1116–1118.

Chang, M. et al, Heterocycles, 1992, 33(1), pp. 147–152.

Anon, Drugs of the Future, 1982, 7, p. 466.

Gorlitzer, K., Arch. Pharm. 1979, 312, pp. 254–261.

Holt, S.J, et al, J. Chem. Soc. 1948, p. 919.

Gorlitzer, K. et al, Pharmazie, 1995, 50, pp. 105–111.

Gorlitzer, K. et al, Arch. Pharm. (Weinheim, Ger.) 1981, 314(1), pp. 76–84.

Oyekan, A.O. et al, Gen. Pharmac. 1993, 24(2), pp. 461–469.

Elslager, E.F. et al, J. Med. Chem. 1971, 15(1), pp. 61–65.

5,681,958

CRYPTOLEPINE ANALOGS WITH HYPOGLYCEMIC ACTIVITY

TABLE OF CONTENTS
1. FIELD OF THE INVENTION
2. BACKGROUND OF THE INVENTION
   2.1 SYNTHESES OF CRYPTOLEPINE AND CRYPTOLEPINE ANALOGS
   2.2 ISOLATION OF NATURAL CRYPTOLEPINE
   2.3 BIOLOGICAL ACTIVITY OF CRYPTOLEPINE AND CRYPTOLEPINE ANALOGS
3. SUMMARY OF THE INVENTION
4. DESCRIPTION OF THE FIGURES
5. DETAILED DESCRIPTION OF THE INVENTION
   5.1 SYNTHESIS OF THE CRYPTOLEPINE ANALOGS
   5.2 METHODS FOR USE OF CRYPTOLEPINE ANALOGS
6. EXAMPLE: SYNTHESIS OF CRYPTOLEPINE ANALOGS
   6.1 MATERIALS AND METHODS
   6.2 CRYPTOLEPINE ANALOGS SYNTHESIZED
7. EXAMPLE: HYPOGLYCEMIC ACTIVITY OF THE CRYPTOLEPINE ANALOGS
   7.1 IN VIVO ACTIVITY OF THE CRYPTOLEPINE ANALOGS
      7.1.1 PROTOCOL FOR IN VIVO EXPERIMENTS
      7.1.2 RESULTS
   7.2 IN VIVO ACTIVITY OF THE CRYPTOLEPINE ANALOGS
      7.2.1 PROTOCOL FOR IN VITRO EXPERIMENTS
      7.2.2 RESULTS

1. FIELD OF THE INVENTION

This invention pertains to a novel group of cryptolepine analogs that are useful as hypoglycemic agents and useful for the treatment of diabetes mellitus, and pertains to a new synthetic process to obtain the novel cryptolepine analogs.

2. BACKGROUND OF THE INVENTION

2.1 SYNTHESES OF CRYPTOLEPINE AND CRYPTOLEPINE ANALOGS

Cryptolepine (I), a member of the quindoline family of alkaloids, is among a rare class of natural products whose synthesis was reported prior to its isolation from nature.

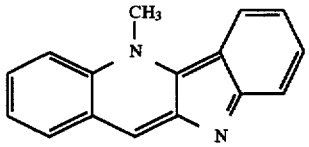

Cryptolepine (I) as its hydrogen iodide salt was first synthesized in 1906 by Fichter and Boehringer [Fichter, F.; Boehringer, R. Chem. Ber. 1906, 39, 3932] from quindoline (II), which was prepared by treatment of a bis-o-nitrobenzylmalonester with alcoholic sodium hydroxide followed by reduction of the intermediate dihydroxyquindoline derivative with HI/Phosphorous.

Proton and carbon NMR (DMSO-d$_6$) spectra for cryptolepine were assigned by Tackie et. al [Tackie, A. N.; Sharaf, M. H. M.; Schiff Jr., P. L.; Boye, G. L.; Couch, R. C.; Martin, G. E. J. Heterocyclic Chem. 1991, 28, 1419]; and by Ablordeppy et. al [Ablordeppy, S. Y; Hufford, C. D.; Borne, R. F.; Dwuma-Badu, D. Planta Med. 1990, 416, 56.

Only a limited number of analogs of cryptolepine (I) have been synthesized. 5-Methylquindolinium chloride [chloride salt of cryptolepine (I)], 5-methylquindoline [cryptolepine (I)], 7-nitro-5-methylquindolinium chloride, 7-amino-5-methylquindolinium chloride (prepared by iron reduction of 7-nitro-5-methylquindolinium chloride), the free base 7-amino-5-methylquindoline, 11-amino-5-methylquindolinium iodide and its chloride salt, and 11-carboxy-5-methylquindolinium chloride and its methosulphate salt have been prepared by Holt and Petrow or Armit and Robinson [(1) Holt, S. J.; Petrow, V. J. Chem Soc. 1948, 919; (2) Armit, J. W.; Robinson, R. J. J. Chem. Soc. 1922, 827]; 5-methyl-10-benzyl-11-benzyloxycarbonyl quindolinium iodide (incorrectly named in literature) has been prepared by Deguitis and Ezyarskaite [Deguitis, Y. A.; Ezyarskaite, A. B. Khim. Geterotsik. Soedin. 1986, 1375]; 5-ethylquindolinium iodide was prepared by Fichter and Boehringer [Fichter, F.; Boehringer, R. Chem. Ber. 1906, 39, 3932]; and 5,10-dimethyl-11-chloroquindolinium chloride and 5,10-dimethyl-11-[N-[4-(diethylamino)-1-methyl-1-aminobutyl] quindolinium dichloride have been synthesized by Görlitzer [Görlitzer, K.; Stockmann, R.; Walter, R. D. Pharmazie 1995, 50, 105].

The cryptolepine analogs of (I) described above were prepared by alkylation with methyl iodide, ethyl iodide or dimethylsulphate. These procedures require the use of high temperatures, long reaction times and/or the use of high pressure vessels to effect alkylation. These procedures are highly impractical for scale-up purposes and lead to decomposition when the cryptolepine nucleus is functionalized with a variety of groups.

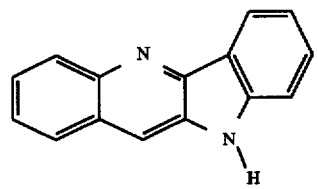

Quindoline (II) had previously been prepared from indigo upon action with base in the presence of a reducing agent followed by decarboxylation with sodium amalgam, and had also been prepared from indigo white in the presence of barium hydroxide and zinc [(1) Giraud, E. Compt. Rend. 1879, 89, 104; (2) Giraud, E. Compt. Rend. 1880, 90, 1429; (3) Schutzenberger, P. Compt. Rend. 1877, 85, 147]. In 1910, Fichter and Rohner synthesized quindoline (II) from isatin and indoxyl followed by decarboxylation of the intermediate quindoline-11-carboxylic acid in the presence of KOH/zinc [Fichter, F. Rohner, B. Chem. Ber. 1910, 43, 3489]. The procedure for the synthesis of quindoline-11-carboxylic acid was later improved by Holt and Petrow, who used the less-readily oxidizable N-acetyl- and O,N-diacetylindoxyls as starting materials [Holt, J. S.; Petrow, V. J. Chem. Soc. 1947, 607].

2.2 ISOLATION OF NATURAL CRYPTOLEPINE

The natural product cryptolepine (I) was first isolated from the plant Cryptolepis triangularis of the family Periplocaceae in 1929 [Clinquart, E. Bull. Acad. R. Med. Belg. 1929, 12, 6237]. Cryptolepine was reisolated from Cryptolepis sanguinolenta in 1951 by Gelleft and Schlittler [Gellert, E.; Raymond-Hamet, Schlittler, E. Helv. Chim. Acta 1951, 34, 642] and again in 1978 together with quindoline (II) and other uncharacterized alkaloids [Dwuma-Badu, D., Ayim, J. S. K.; Fiagbe, N. I. Y.; Knapp, J. E.; Schiff Jr., P. L.; Slatkin, D. J. J. Pharm. Sci. 1978, 67, 433]. In a study of Sri-Lankan medicinal plants, cryptolepine was identified as the major alkaloid in *Sida acuta* [Gunatilaka, A. A., *Planta Medica* 1980, 39, 66].

2.3 BIOLOGICAL ACTIVITY OF CRYPTOLEPINE AND CRYPTOLEPINE ANALOGS

According to the West African Pharmaceutical Federation *Cryptolepis sanguinolenta* has been widely used in folk medicine for the treatment of malaria, gonorrhoea, and hypertension. The antimalarial activity of Cryptolepis roots is linked to the presence of cryptolepine. As an antiinflammatory agent it is claimed to be as active as piroxicam or indomethacin [IMS Pharmaceutical Marketletter, May 7, 1984, p. 13].

A study conducted in 1937 described marked hypothermia in dogs after administration of cryptolepine and noted an antagonistic effect to epinephrine characterized by decreased hypertension and renal vasoconstriction; a lethal dose was determined in guinea pigs after i.p. injection as 120 mg/kg [Raymond-Hamet, C., *C. R. Soc. Biol.* 1937, 126, 768]. A 1938 study showed a marked and protracted hypotensive response in vasectomized dogs after i. v. administration of cryptolepine [Raymond-Hamet, C., *C. R. Acad. Sci.*, 1938, 208, 105]. A report claimed that cryptolepine possessed hypotensive and antibacterial properties [*Drugs Future*, 1982, 7, 466]. More detailed antimicrobial activities for alcoholic extracts of *Cryptolepis sanguinolenta* were described [Boakye-Yiadom, K.; Heman-Ackah, S. M., *J. Pharm. Sci.* 1979, 68, 1510].

5-Methylquindolinium chloride [chloride salt of cryptolepine (I)], 7-nitro-5-methylquindolinium chloride, 7-amino-5-methylquindolinium chloride, 11-amino-5-methylquindolinium chloride, and 11-carboxy-5-methylquindolinium chloride were evaluated for use as antimalarial and antibacterial agents. Among these, 11-amino-5-methylquindolinium chloride showed marginal activity against *T. congolense*, and 7-amino-5-methylquindolinium chloride and 11-amino-5-methylquindolinium chloride had antibacterial activity against *E. coli* and *S. aureus* [Holt, S. J.; Petrow, V. *J. Chem Soc.* 1948, 919].

In 1980, a paper described the noradrenoreceptor antagonism of cryptolepine in isolated rat vas deferens [Naomesi, B. K. and Bangbose, S. O. A., *Planta Medica* 1980, 39, 51]. Cryptolepine's antiinflammatory action was reported in 1981 by the same researchers who identified prostaglandin E2 antagonism as the cause. [Bangbose, S. O. A. and Noamesi, B. K., *Planta Medica*, 1981, 41, 392].

New synthetic methodology toward the quindoline ring system has been developed [(1) Sevodin, V. P.; Velezheva, V. S.; Erofeev, Y. V.; Suvorov, N. N. *Khim. Geterotsik. Soedin.* 1984, 1667; (2) Sevodin, V. P.; Velezheva, V. S.; Suvorov, N. N. *Khim. Geterotsik. Soedin.* 1982, 1125; (3) Buzas, A.; Merour, J. Y.; *Synthesis*, 1989, 458; (4) Merour, J. Y.; Coadou, J. Y.; Tatibouet, F. *Synthesis* 1982, 1053; (5) Görlitzer, K.; Weber, J. *Arch. Pharm.* (Weinheim) 1981, 314, 852.

The effects of cryptolepine alone and in combination with dipyridamole were studied in a mouse model of arterial thrombosis in 1989. [Oyekam, A. O.; Okafor, J. P. O., *J. Ethnopharm.* 1989, 27, 141].

Cryptolepine was found to possess high anti-Candida activity as well as pronounced activity against Gram-positive bacteria. Additionally, weak activity against some Gram-negative bacteria but no antiviral activity was observed [Cimanga, K.; Pieters, L.; Clayes, M.; Vanden Berghe, D.; Vlientick, A. J. *Planta Medica* 1992, 57. Supp 2, A98].

More recently, cryptolepine and related alkaloids were found to possess antimuscarinic activity at the M1, M2, and M3 receptors [Rauwald, H. W.; Kober, N. C.; Mutschler, E.; Lambrecht, G. *Planta Medica* 1992, 58, 486].

Cryptolepine has been described to have an effect on collagen-induced platelet aggregation and on the mobilization and metabolism of arachidonic acid in a rabbit model [Oyekan, A. O.; Ablordeppey, S. Y. *Gen Pharmacol* 1993, 24, 1285]. Cryptolepine's hypotensive and vasodilator mechanisms of action on perfused rat kidney were further described [Oyekan, A. O. *J. Cardiovasc. Pharmacol.* 1994, 23, 602].

Over the years there has been interest in the use of substituted analogs of quindoline (II), indolo[3,2-b]quinolines, for use as antitumor agents, DNA intercalators and antileukemic agents [(1) Yamato, M.; Takeuchi, Y.; Chang, M.-r.; Hashigaki, K. *Chem. Pharm. Bull.* 1992, 40, 528; (2) Yamato, M.; Takeuchi, Y.; Chang, M.-r.; Hashigaki, K.; Tsuruo, T.; Tashiro, T.; Tsukagoshi, S. *Chem. Pharm. Bull.* 1990, 38, 3048; (3) Takeuchi, Y.; Chang, M.-r.; Hashigaki, K.; Yamato, M. *Chem. Pharm. Bull.* 1991, 39, 1629; (4) Chang, M.-r.; Takeuchi, Y.; Hashigaki, K.; Yamato, M. *Heterocycles* 1992, 33, 147; (5) Takeuchi, Y.; Chang, M.-r.; Hashigaki, K.; Tashiro, T.; Tsuruo, T.; Tsukagoshi, S.; Yamato, M. *Chem. Pharm. Bull.* 1992, 40, 1481; (6) G örlitzer, K.; Stockmann, R.; Walter, W. D. *Pharmazie*, 1994, 49, 231; (7) Yamato, M; Takeuchi, Y.; Hashigaki, K.; Ikeda, Y.; Chang, M.-r.; Takeuchi, K.; Matsushima, M.; Tsuruo, T.; Tashiro, T.; Tsukagoshi, S.; Yamashita, Y.; Nakano, H. *J. Med. Chem.* 1989, 32, 1295; (8) Yamato, M.; Hashigaki, K. EP 376166 A1], antimalarial agents [(1) Görlitzer, K.; Stockmann, R.; Walter, W. D. *Pharmazie* 1994, 49, 231; (2) Görlitzer, K.; Stockmann, R.; Walter, R. D. *Pharmazie* 1995, 50, 105; (3) Tackie, A.; Schiff, P.; Sharaf, M. WO 9418203], blood platelet inhibitors [Görlitzer, K.; Weber, J. *Arch. Pharm. (Weinheim)* 1982, 315, 532] and for use in electrophotography [(1) Jezerskaite, A.; Deguitis, J.; Undzenas, A.; Kalcheva, V. *Izv. Khim.* 1989, 22, 113; (2) Ezerskaite, A. *Izv. Khim.* 1989, 22, 101; (3) Degutis, Y. A.; Ezyarskaite, A. B. *Khim. Geterotsik. Soedin.* 1986, 1375].

To the knowledge of the inventors, no prior study has described any hypoglycemic activity of Cryptolepine analogs of (I) nor was there any suggestion in the prior art that cryptolepine analogs would be useful as hypoglycemic agents.

Citation or identification of any reference in Section 2 of this application shall not be construed as an admission that such reference is available as prior art to the present invention.

3. SUMMARY OF THE INVENTION

The present invention provides novel cryptolepine analogs, as well as pharmaceutically acceptable salts thereof, having hypoglycemic activity or having activity as agents to lower triglyceride levels, for example in diabetic subjects, and a process to prepare the novel cryptolepine analogs. Particularly, the invention provides cryptolepine compounds having formula III:

[Structure III shown with positions labeled 1-11, 4a, 5a, 5b, 9a, 10a, 11a, with substituents $R_1$ through $R_{11}$ and N at position 5 and position 10]

and pharmaceutically acceptable salts thereof, wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_5$ is selected from the group consisting of $C_1$–$C_{10}$ alkyl, $C_2$–$C_{10}$ alkenyl or $C_2$–$C_{10}$ alkynyl groups, $C_3$–$C_6$ cycloalkyl and phenylmethyl; said $C_1$–$C_{10}$ alkyl, $C_2$–$C_{10}$ alkenyl and $C_2$–$C_{10}$ alkynyl groups being optionally substituted with one or more groups consisting of halogen, amino, methylamino, dimethylamino, trimethylamino, hydroxy, methoxy, ethoxy, phenoxy, phenyl and $C_1$–$C_6$ alkyl; said $C_3$–$C_6$ cycloalkyl group being optionally substituted with one or more groups selected from the group consisting of halogen, phenyl, and $C_1$–$C_6$ alkyl; said phenylmethyl being optionally substituted with one or more groups selected from the group consisting of halogen, amino, dimethylamino, hydroxy, methoxy, ethoxy, $C_1$–$C_6$ alkyl, isopropyl, isobutyl, tert-butyl, and phenyl;

$R_6$, $R_7$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl;

$R_{11}$ is selected from the group consisting of hydrogen, halogen, azide, cyano, $COOR_{12}$, $OR_{13}$, $NHR_{13}$, $SR_{13}$, phenyl, optionally substituted phenyl, a $C_1$–$C_{10}$ alkyl group, a $C_2$–$C_{10}$ alkenyl group or a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, or phenyl; said $C_1$–$C_{10}$ alkyl group, $C_2$–$C_{10}$ alkenyl group or a $C_2$–$C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1$–$C_6$ alkyl or phenyl;

each $R_{12}$ is selected from the group consisting of hydrogen and a $C_1$–$C_6$ alkyl group; said $C_1$–$C_6$ alkyl group being optionally substituted with one or more groups selected from the group consisting of phenyl and $C_1$–$C_3$ alkyl; and each $R_{13}$ is selected from the group consisting of hydrogen, phenyl and a $C_1$–$C_6$ alkyl group; said $C_1$–$C_6$ alkyl group being optionally substituted with one or more groups selected from the group consisting of phenyl and $C_1$–$C_3$ alkyl; said phenyl being optionally substituted with one or more groups selected from the group consisting of halogen, methoxy, ethoxy, hydroxy, amino, and $C_1$–$C_6$ alkyl;

with the proviso that when $R_1$–$R_4$, $R_6$–$R_9$ and $R_{11}$ are H, $R_5$ is not $CH_3$ or $CH_2CH_3$; and with the further proviso that the compound of Formula III is not selected from the group consisting of:
5-methylquindoline;
7-nitro-5-methylquindoline;
7-amino-5-methylquindoline;
11-amino-5-methylquindoline; and
11-carboxy-5-methylquindoline.

The novel cryptolepine analogs of Formula III are useful as hypoglycemic agents.

The invention further provides cryptolepine compounds having formula IV:

[Structure IV shown, similar to III but with $N^+$ at position 5, $X^-$ counterion, and $R_{10}$ on the nitrogen at position 10]

and pharmaceutically acceptable salts thereof, wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_5$ is selected from the group consisting of $C_1$–$C_{10}$ alkyl, $C_2$–$C_{10}$ alkenyl or $C_2$–$C_{10}$ alkynyl groups, $C_3$–$C_6$ cycloalkyl, and phenylmethyl; said $C_1$–$C_{10}$ alkyl, $C_2$–$C_{10}$ alkenyl and $C_2$–$C_{10}$ alkynyl groups being optionally substituted with one or more groups consisting of halogen, amino, methylamino, dimethylamino, trimethylamino, hydroxy, methoxy, ethoxy, phenoxy, phenyl and $C_1$–$C_6$ alkyl; said $C_3$–$C_6$ cycloalkyl group being optionally substituted with one or more groups selected from the group consisting of halogen, phenyl, and $C_1$–$C_6$ alkyl; said phenylmethyl being optionally substituted with one or more groups selected from the group consisting of halogen, amino, dimethylamino, hydroxy, methoxy, ethoxy, $C_1$–$C_6$ alkyl, isopropyl, isobutyl, tert-butyl, and phenyl;

$R_6$, $R_7$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, optionally substituted phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of $C_1$–$C_6$ alkyl and phenyl;

$R_{10}$ is selected from the group consisting of hydrogen, acetyl, $C_1$–$C_{10}$ alkyl group, $C_2$–$C_{10}$ alkenyl group, $C_2$–$C_{10}$ alkynyl group and phenylmethyl; said $C_1$–$C_{10}$ alkyl, $C_1$–$C_{10}$ alkenyl and $C_2$–$C_{10}$ alkynyl groups being optionally substituted with one or more groups selected from the group consisting of halogen, amino, methylamino, dimethylamino, trimethylamino, hydroxy, methoxy, ethoxy, phenoxy, phenyl and $C_1$–$C_6$ alkyl; said phenylmethyl being optionally substituted with one or more groups selected from the group consisting of halogen, amino, dimethylamino, hydroxy, methoxy, ethoxy, $C_1$–$C_6$ alkyl, isopropyl, isobutyl, tert-butyl, and phenyl;

$R_{11}$ is selected from the group consisting of hydrogen, halogen, azide, cyano, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1$–$C_6$ alkyl and phenyl;

$R_{12}$ is selected from the group consisting of hydrogen and a $C_1$–$C_6$ alkyl group; said $C_1$–$C_6$ alkyl group being optionally substituted with one or more groups selected from the group consisting of phenyl and $C_1$–$C_3$ alkyl;

each $R_{13}$ is selected from the group consisting of hydrogen, phenyl and a $C_1$–$C_6$ alkyl group; said $C_1$–$C_6$ alkyl group being optionally substituted with one or more groups selected from the group consisting of phenyl and $C_1$–$C_3$ alkyl; said phenyl being optionally substituted with one or more groups selected from the group consisting of halogen, methoxy, ethoxy, hydroxy, amino, and $C_1$–$C_6$ alkyl;

$X^{31}$ is selected from the group consisting of acetate, iodide, chloride, bromide, fluoride, hydroxide, sulfate, hydrogensulfate, methanesulfonate, trifluoromethanesulfonate, toluenesulfonate, benzenesulfonate, phosphate, hydrogenphosphate, dihydrogenphosphate, succinate, ascorbate, tartrate, gluconate, benzoate, malate, fumarate, and citrate;

with the proviso that when $R_1$–$R_4$, $R_6$–$R_9$ and $R_{11}$ are H, $R_5$ does not equal $CH_3$ or $CH_2CH_3$; and with the further proviso that the compound of Formula IV is not selected from the group consisting of:
5-methylquindolinium chloride;
5-methylquindolinium iodide;
5-methylquindolinium methosulfate;
5-ethylquindolinium chloride;
5-ethylquindolinium iodide;
5-ethylquindolinium methosulfate;
7-nitro-5-methylquindolinium chloride;
7-amino-5-methylquindolinium chloride;
11-amino-5-methylquindolinium iodide;
11-amino-5-methylquindolinium chloride;
11-carboxy-5-methylquindolinium chloride;
11-carboxy-5-methylquindolinium methosulfate;
5-methyl-10-benzyl-11-benzyloxycarbonylquindolinium iodide;
5,10-dimethyl-11-chloroquindolinium chloride; and
5,10-dimethyl-11-[N-[4-(diethylamino)-1-methyl-1-aminobutyl]quindolinium dichloride.

When $R_{10}$ is hydrogen, compounds of formula IV are salts of compounds of formula III. In such an instance, compounds of formula IV can exist in a tautomeric form given by formula V, or in an equilibrium mixture thereof, according to equation 1:

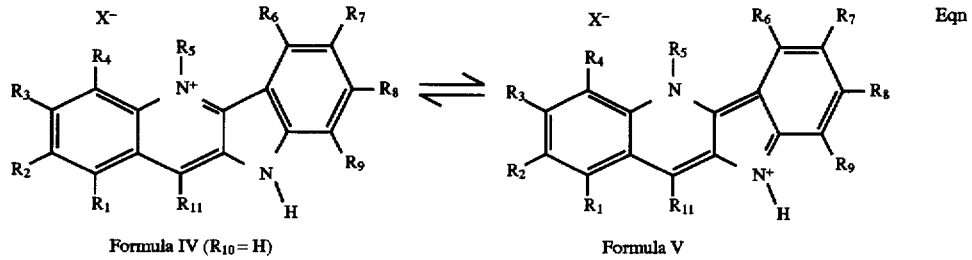

Formula IV ($R_{10}$=H)   Formula V   Eqn 1 where $R_1$, $R_2$, $R_3$, $R_4$, $R_5$, $R_6$, $R_7$, $R_8$, $R_9$, $R_{11}$ and $X^-$ are defined as defined for compounds of formula IV. It is to be understood that compounds of Formula IV and Formula V are equivalent in biological function and activity when $R_1$–$R_9$, $R_{11}$ and $X^-$ in compounds of Formula IV are the same as $R_1$–$R_9$, $R_{11}$ and $X^-$ in compounds of Formula V.

The cryptolepine analogs of Formula IV are useful as hypoglycemic agents.

The invention still further provides cryptolepine analogs having formula VI:

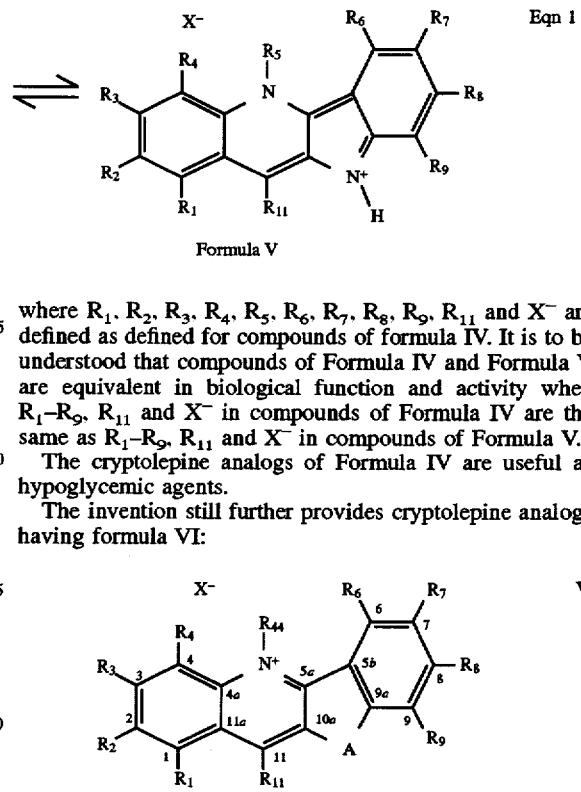

and pharmaceutically acceptable salts thereof, wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_6$, $R_7$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of $C_1$–$C_6$ alkyl and phenyl;

$R_{11}$ is selected from the group consisting of hydrogen, halogen, azide, cyano, $COOR_{12}$, $OR_{13}$, $NHR_{13}$, $SR_{13}$, phenyl, optionally substituted phenyl, a $C_1-C_{10}$ alkyl group, a $C_2-C_{10}$ alkenyl group and a $C_2-C_{10}$ alkynyl group; said phenyl being optionally substituted with one or more groups selected from the group consisting of halogen, amino, hydroxy, methoxy, ethoxy, $C_1-C_6$ alkyl, and phenyl; said $C_1-C_{10}$ alkyl group, $C_2-C_{10}$ alkenyl group and a $C_2-C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1-C_6$ alkyl and phenyl;

$R_{12}$ is selected from the group consisting of hydrogen and a $C_1-C_6$ alkyl group; said $C_1-C_6$ alkyl group being optionally substituted with one or more groups selected from the group consisting of phenyl and $C_1-C_3$ alkyl;

$R_{13}$ is selected from the group consisting of hydrogen, phenyl and a $C_1-C_6$ alkyl group; said $C_1-C_6$ alkyl group being optionally substituted with one or more groups selected from the group consisting of phenyl and $C_1-C_3$ alkyl; said phenyl being optionally substituted with one or more groups selected from the group consisting of halogen, methoxy, ethoxy, hydroxy, amino, and $C_1-C_6$ alkyl;

$X^-$ is selected from the group consisting of acetate, iodide, chloride, bromide, fluoride, hydroxide, sulfate, hydrogensulfate, methanesulfonate, trifluoromethanesulfonate, toluenesulfonate, benzenesulfonate, phosphate, hydrogenphosphate, dihydrogenphosphate, succinate, ascorbate, tartrate, gluconate, benzoate, malate, fumarate, and citrate;

$R_{44}$ is selected from the group consisting of oxygen, $C_1-C_{10}$ alkyl, $C_2-C_{10}$ alkenyl or $C_2-C_{10}$ alkynyl groups, $C_3-C_6$ cycloalkyl, and phenylmethyl; said $C_1-C_{10}$ alkyl, $C_2-C_{10}$ alkenyl and $C_2-C_{10}$ alkynyl groups being optionally substituted with one or more groups selected from the group consisting of halogen, amino, methylamino, dimethylamino, trimethylamino, hydroxy, methoxy, ethoxy, phenoxy, phenyl and $C_1-C_6$ alkyl; said $C_3-C_6$ cycloalkyl group being optionally substituted with one or more groups selected from the group consisting of halogen, phenyl, and $C_1-C_6$ alkyl; said phenylmethyl being optionally substituted with one or more groups selected from the group consisting of halogen, amino, dimethylamino, hydroxy, methoxy, ethoxy, $C_1-C_6$ alkyl, isopropyl, isobutyl, tert-butyl, and phenyl;

A is selected from the group consisting of O, S, $CH_2$, SO, or $SO_2$; and with the proviso that when $R_1$–$R_4$, $R_6$–$R_9$ and $R_{11}$ is H, $R_{44}$ is not oxygen.

The cryptolepine analogs of the Formula VI are useful as hypoglycemic agents.

The invention still further provides for a method of synthesizing novel cryptolepine analogs, comprising the step of alkylating a compound of Formula VII:

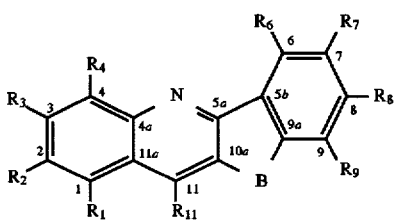

VII wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1-C_{10}$ alkyl group, a $C_2-C_{10}$ alkenyl group and a $C_2-C_{10}$ alkynyl group; said phenyl being optionally substituted with one or more groups selected from the group consisting of halogen, amino, hydroxy, methoxy, ethoxy, $C_1-C_6$ alkyl, and phenyl; said $C_1-C_{10}$ alkyl, $C_2-C_{10}$ alkenyl and $C_2-C_{10}$ alkynyl groups being optionally substituted with one or more groups selected from the group consisting of $C_1-C_6$ alkyl and phenyl;

$R_6$, $R_7$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, a $C_1-C_{10}$ alkyl group, a $C_2-C_{10}$ alkenyl group and a $C_2-C_{10}$ alkynyl group; said phenyl being optionally substituted with one or more groups selected from the group consisting of halogen, amino, hydroxy, methoxy, ethoxy, $C_1-C_6$ alkyl, and phenyl; said $C_1-C_{10}$ alkyl group, $C_2-C_{10}$ alkenyl group and $C_2-C_{10}$ alkynyl groups being optionally substituted with one or more groups selected from the group consisting of $C_1-C_6$ alkyl and phenyl;

$R_{11}$ is selected from the group consisting of hydrogen, halogen, azide, cyano, $COOR_{12}$, $OR_{13}$, $NHR_{13}$, $SR_{13}$, phenyl, a $C_1-C_{10}$ alkyl group, a $C_2-C_{10}$ alkenyl group and a $C_2-C_{10}$ alkynyl group; said phenyl being optionally substituted with one or more groups selected from the group consisting of halogen, amino, hydroxy, methoxy, ethoxy, $C_1-C_6$ alkyl, and phenyl; said $C_1-C_{10}$ alkyl group, $C_2-C_{10}$ alkenyl group and $C_2-C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1-C_6$ alkyl and phenyl;

$R_{12}$ is selected from the group consisting of hydrogen and a $C_1-C_6$ alkyl group; said $C_1-C_6$ alkyl group being optionally substituted with one or more groups selected from the group consisting of phenyl and $C_1-C_3$ alkyl;

$R_{13}$ is selected from the group consisting of hydrogen, phenyl and a $C_1-C_6$ alkyl group; said $C_1-C_6$ alkyl group being optionally substituted with one or more groups selected from the group consisting of phenyl and $C_1-C_3$ alkyl; said phenyl being optionally substituted with one or more groups selected from the group consisting of halogen, methoxy, ethoxy, hydroxy, amino, and $C_1-C_6$ alkyl;

B is selected from the group consisting of O, S, $CH_2$, SO, or $SO_2$, or $NR_{10}$; and $R_{10}$ is selected from the group consisting of methyl and hydrogen;

with methyl trifluoromethanesulfonate to afford a cryptolepine analog having hypoglycemic activity.

Preferred cryptolepine analogs of the present invention useful as hypoglycemic agents are:

5-Butylquindoline;
5-Benzylquindoline;
5,10-Dibenzylquindoline;
5-Methyl-11-(methoxycarbonyl)quindoline;
5-(4'-Fluorobenzyl)quindoline;
2-Fluoro-5-methyl-11-chloroquindoline;
2-Fluoro-5-methyl-11-chloroquindoline;
2-Fluoro-5-methyl-11-(phenoxy)quindoline;
2-Fluoro-5-methyl-11-(phenylamino)quindoline;
2-Fluoro-5-methyl-11-phenylquindolinium chloride;
2-Fluoro-5-methyl-11-[(4-chlorophenyl) thio]quindoline;
6-Methoxy-5-methylquindoline;
2-Chloro-5-methyl-11-chloroquindoline;
1-Chloro-5-methyl-11-chloroquindoline;
2-Fluoro-5-methylquindoline;
7-Bromo-8-chloro-5-methylquindoline;
7-Bromo-6-chloro-5-methylquindoline;
7-Fluoro-11-iodo-5-methylquindoline;
7-Fluoro-11-chloro-5-methylquindoline;

11-Chloro-6-fluoro-5-methylquindoline;
11-Chloro-8-fluoro-5-methylquindoline;
11-Chloro-9-fluoro-5-methylquindoline;
9-Fluoro-11-iodo-5-methylquindoline;
9-Fluoro-11-chloro-5-methylquindoline;
11-Chloro-7-phenyl-5-methylquindoline;
4,11-Dichloro-5-methylquindoline; and pharmaceutically acceptable salts thereof.

Especially preferred cryptolepine analogs of the present invention useful as hypoglycemic agents are:

2-Fluoro-5-methylquindolinium hydrochloride (Compound A);
7-Bromo-8-chloro-5-methylquindolinium hydrochloride (Compound B);
5-Ethylquindolinium hydrochloride (Compound C);
5-Butylquindolinium hydrochloride (Compound D);
7-Fluoro-11-iodo-5-methylquindolinium hydrochloride (Compound E);
9-Fluoro-11-iodo-5-methylquindolinium hydrochloride (Compound F);
5-(4'-Fluorobenzyl)quindolinium hydrochloride (Compound G);
2-Fluoro-5-methyl-11-(phenylamino)quindolinium hydrochloride (Compound H);
2-Fluoro-5-methyl-11-(phenoxy)quindolinium hydrochloride (Compound I);
5-Methylquindoline (Compound J);
5-Methylquindolinium hydrochloride (Compound K);
5-Benzylquindolinium hydrochloride (Compound L);
5,10-Dibenzylquindolinium chloride (Compound M);
5,10-Dimethyl-11-methoxycarbonylquindolinium iodide (Compound N);
5-Methyl-11-methoxycarbonyl quindolinium hydroiodide (Compound O);
6-Methoxy-5-methylquindolinium hydrochloride (Compound P);
5-methyl-11-chloroquindolinium hydrochloride (Compound Q);
2-Fluoro-5-methyl-11-chloroquindolinium hydrochloride (Compound R);
11-Chloro-5-methylbenzofuro[3,2-b]quinoline trifluoromethanesulfonate (Compound S);
2-Fluoro-5-methyl-11-phenylquindolinium hydrochloride (Compound T);
11-Chloro-5-methylbenzothieno[3,2-b]quinolinium trifluoromethanesulfonate (Compound U);
11-(4-Chlorophenylthio)-5-methylbenzofuro[3,2-b]quinolinium chloride (Compound V);
2-Fluoro-5-methyl-11-[(4-chlorophenyl)thio]quindolinium hydrochloride (Compound W);
11-Chloro-6-fluoro-5-methylquindolinium hydrochloride (Compound X);
2-Chloro-5-methyl-11-chloroquindolinium hydrochloride (Compound Y); 11-Chloro-5-methylindeno[1,2-b]quinolinium trifluoromethanesulfonate (Compound Z);
11-[(4-Chlorophenyl)thio]-5-methylindeno[1,2-b]quinolinium chloride (Compound AA);
1-Chloro-5-methyl-11-chloroquindolinium hydrochloride (Compound AB);
11-Chloro-8-fluoro-5-methylquindolinium hydrochloride (Compound AC);
11-Chloro-7-phenyl-5-methylquindolinium hydrochloride (Compound AD);
5-Methylquindolinium hydroiodide (Compound AE); and
4,11-Dichloroquindolinium hydrochloride (Compound AF).

The present invention may be understood more fully by reference to the following figures, detailed description and illustrative examples which are intended to exemplify non-limiting embodiments of the invention.

4. DESCRIPTION OF THE FIGURES

Figure 9:
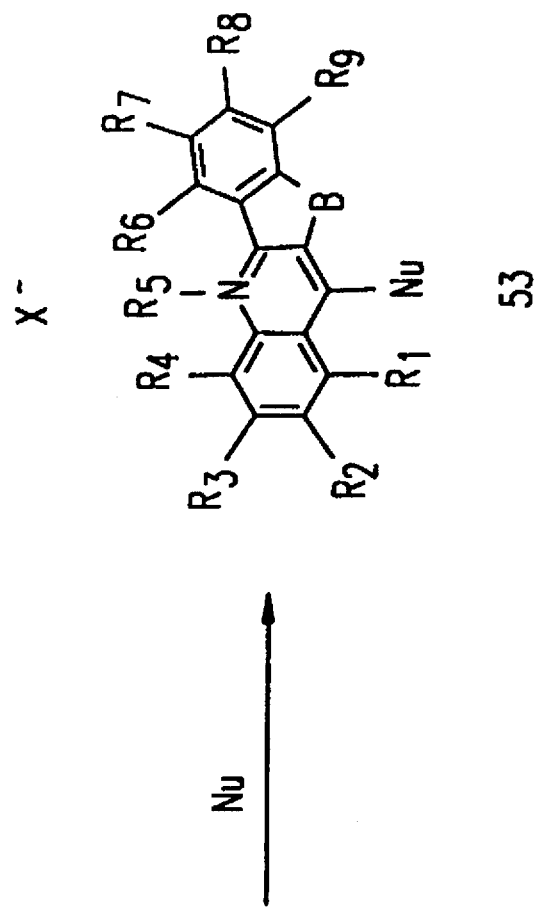
Figure 9:
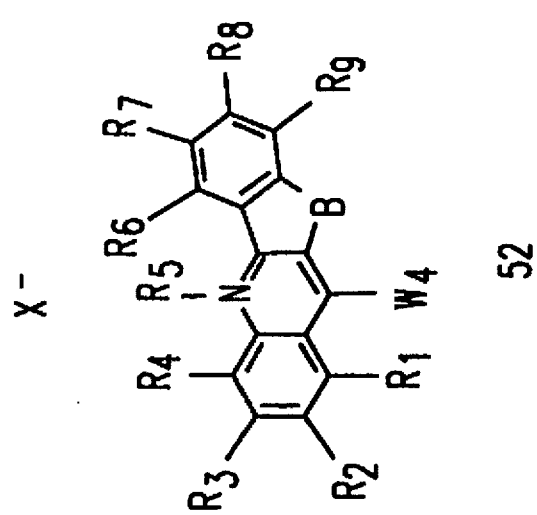

FIG. 9 is a flow chart describing a general preparation of 11-substituted cryptolepine analogs. $R_1$–$R_4$, $R_6$–$R_9$, $R_{11}$–$R_{13}$ and B are defined above in Section 3, except that $R_{11}$ is not $COOR_{12}$; $W_4$=Cl, Br and I; Nu is halogen, azide, cyano, $HOR_{13}$, $^-OR_{13}$, $NH_2R_{13}$, $^-NHR_{13}$, $HSR_{13}$, $^-SR_{13}$ or $R_{45}M^-$, wherein $R_{45}$ is phenyl, a $C_1$–$C_{10}$ alkyl group, a $C_2$–$C_{10}$ alkenyl group or a $C_2$–$C_{10}$ alkynyl group, wherein each member of said $R_{45}$ is optionally substituted with one or more groups selected from the group consisting of halogen, amino, methylamino, dimethylamino, trimethylamino, hydroxy, methoxy, ethoxy, phenoxy, phenyl and $C_1$–$C_6$ alkyl; said $C_3$–$C_6$ cycloalkyl group being optionally substituted with one or more groups selected from the group consisting of halogen, phenyl, and $C_1$–$C_6$ alkyl.

5. DETAILED DESCRIPTION OF THE INVENTION

5.1 SYNTHESIS OF THE CRYPTOLEPINE ANALOGS

The cryptolepine analogs of the present invention can be prepared by the synthetic methods outlined below.

Figure 1:
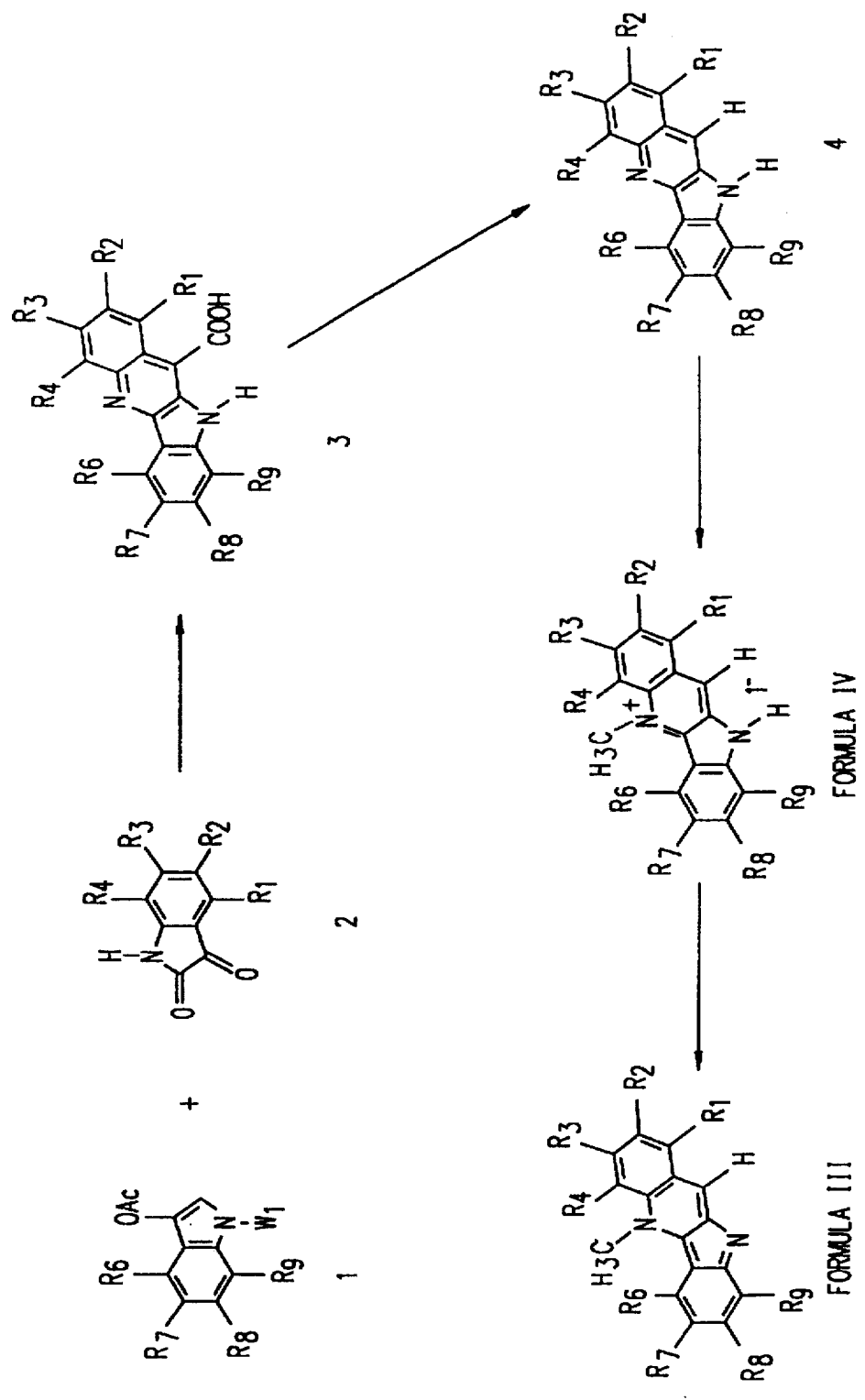
FIG. 1 is a flow chart describing a general preparation of cryptolepines of Formulae III and IV from isatins and indolines. $R_1$–$R_4$, $R_6$–$R_9$ and $R_{11}$ are defined above in Section 3; $W_1$=$CH_3CO$ and H.

As shown in FIG. 1 cryptolepines of Formulae III and IV can be prepared using suitably substituted indolines 1 and suitably substituted isatins 2. The general procedure described in FIG. 1 to prepare quindolines 4 and cryptolepines of Formula IV is novel. Previous reports used to prepare the parent quindoline 4 and parent cryptolepine of Formula IV ($R_1=R_2=R_3=R_4=R_6=R_7=R_8=R_9=H$) are as follows: [(1) Holt, J. S.; Petrow, V. *J. Chem. Soc.* 1947, 607; (2) Fichter, F.; Boehringer, R. *Chem. Ber.* 1906, 3932; (3) Degutis, Y. A.; Ezyarskaite, A. B. *Khim. Geterotsik. Soedin.* 1986, 1375]. A substituted isatin 1 is treated with a substituted indoline 2 in the presence of a base to give quindoline carboxylic acid 3. Preferable bases include potassium hydroxide and sodium hydroxide. Preferably, the reaction is conducted in an inert atmosphere. Decarboxylation of 3 in a high boiling solvent, preferably diphenyl ether, provides quindoline 4. Alkylation of quindolines 4 with conventional methylating agents such as dimethyl sulfate, methyl methanesulfonate, methyl trifluoromethanesulfonate and preferably methyl iodide provides the quindolinium salts which can be ion-exchanged by methods known to those skilled in the art to afford the quindolinium iodide of Formula IV. The methylation is performed in the presence of a polar organic solvent, preferably methanol. The methylation reaction may optionally be performed under pressure, preferably under high pressure in a teflon-lined Parr bomb. Other preferred methods of performing this alkylation step are described in the following FIGS. 2–9.

The free base of Formula IV can be prepared by treatment of the compound of Formula IV with base, preferably with an aqueous solution of $Na_2CO_3$, $K_2CO_3$, KOH, or NaOH, to provide cryptolepines of Formula III. The conversion of cryptolepines of Formula IV into cryptolepines of Formula III is most preferably achieved by adsorbing the quindolinium salt of Formula IV onto a solid basic support such as $Na_2CO_3$, pouring the adsorbate on a column of basic alumina or any other basic solid phase support column and eluting with a polar organic solvent system, preferably ethanol-free chloroform, to remove any quindoline 4 impurities; elution with methanol-chloroform (0.5–5% methanol-chloroform) provides cryptolepines of Formula III.

Quindoline precursors 4 necessary for the preparation of cryptolepine analogs of Formulae III and IV can also be prepared by other methods. For example, a suitably substituted anthranilic acid derivative may be condensed with an analogously substituted hydroxyindole in the presence of $Ba(OH)_2$, followed by decarboxylation in the presence of potassium hydroxide and zinc or sodium amalgam to give substituted quindolines 4 [(1) Giraud, E. *Compt. Rend.* 1879, 89, 104; (2) Giraud, E. *Compt. Rend.* 1880, 90, 1429; (3) Schutzenberger, P. *Compt. Rend.* 1877, 85, 147; (4)Fichter, F. Rohner, B. *Chem. Ber.* 1910, 43, 3489].

Alternatively, a substituted 1,2-(o-nitrophenyl)-1-cyanoethane can be heated in the presence of ammonium sulfide in alcohol to obtain substituted quindoline precursors 4 [Gabriel, P.; Eschenbach, H. *Chem. Ber.* 1897, 30, 3020].

Substituted quindolines 4 can also be obtained from substituted bis(o-nitrobenzyl)malonate which, after decarboxylation with alkali, can be heated in the presence of HI/P [Fichter, F.; Boehringer, R. *Chem. Ber.* 1906, 39, 3932].

Nitro and amino quindolines 4 can be prepared using literature methods [(1) Giraud, E. *Compt. Rend.* 1880, 90, 1429–1430; (2) Holt, J. S.; Petrow, V. *J. Chem. Soc.* 1947, 607; (3) Chang, M.-r.; Takeuchi, Y.; Hashigaki, K.; Yamato, M. *Heterocycles* 1992, 33, 147; (4) Holt, J. S.; Petrow, V. *J. Chem. Soc.* 1948, 919; (5) Holt, J. S.; Petrow, V. *J. Chem. Soc.* 1948, 922.

Other routes to quindolines 4 or cryptolepines of Formula III or IV may also be used [(1) Armit, J. W.; Robinson, R. J. *J. Chem. Soc.* 1922, 827; (2) Gellért, E.; Hamet, R.; Schlittler, E. *Helv. Chim. Acta* 1951, 34, 642; (3) Fichter, F.; Probst, H. *Chem. Ber.* 1907, 40, 3478; (4) Sevodin, V. P.; Velezheva, V. S.; Erofeev, Y. U.; Surorov, N. N. *Khim. Geterotsik. Soedin.* 1984, 1667; (5) Sevodin, V. P.; Velezheva, V. S.; Surorov, N. N. *Khim. Geterotsik. Soedin.* 1982, 1125; (6) Holt, J. S.; Petrow, V. *J. Chem. Soc.* 1948, 919; (7) Holt, J. S.; Petrow, V. *J. Chem. Soc.* 1948, 922; (8) Schulte, K. E.; Reisch, J.; Stoess, U. *Arch. Pharm.* 1972, 305, 523; (9) Ablordeppey, S. Y. S. In *The First International Seminar on Cryptolepine, Proceedings*; Boakye-Yiadom, E.; Bamgbose, O. A., Ed; Jul. 27–30, 1983; pp 30–36; (10) Görlitzer, K.; Weber, J. *Arch. Pharm.* (Weinheim) 1981, 314, 850].

Figure 2:
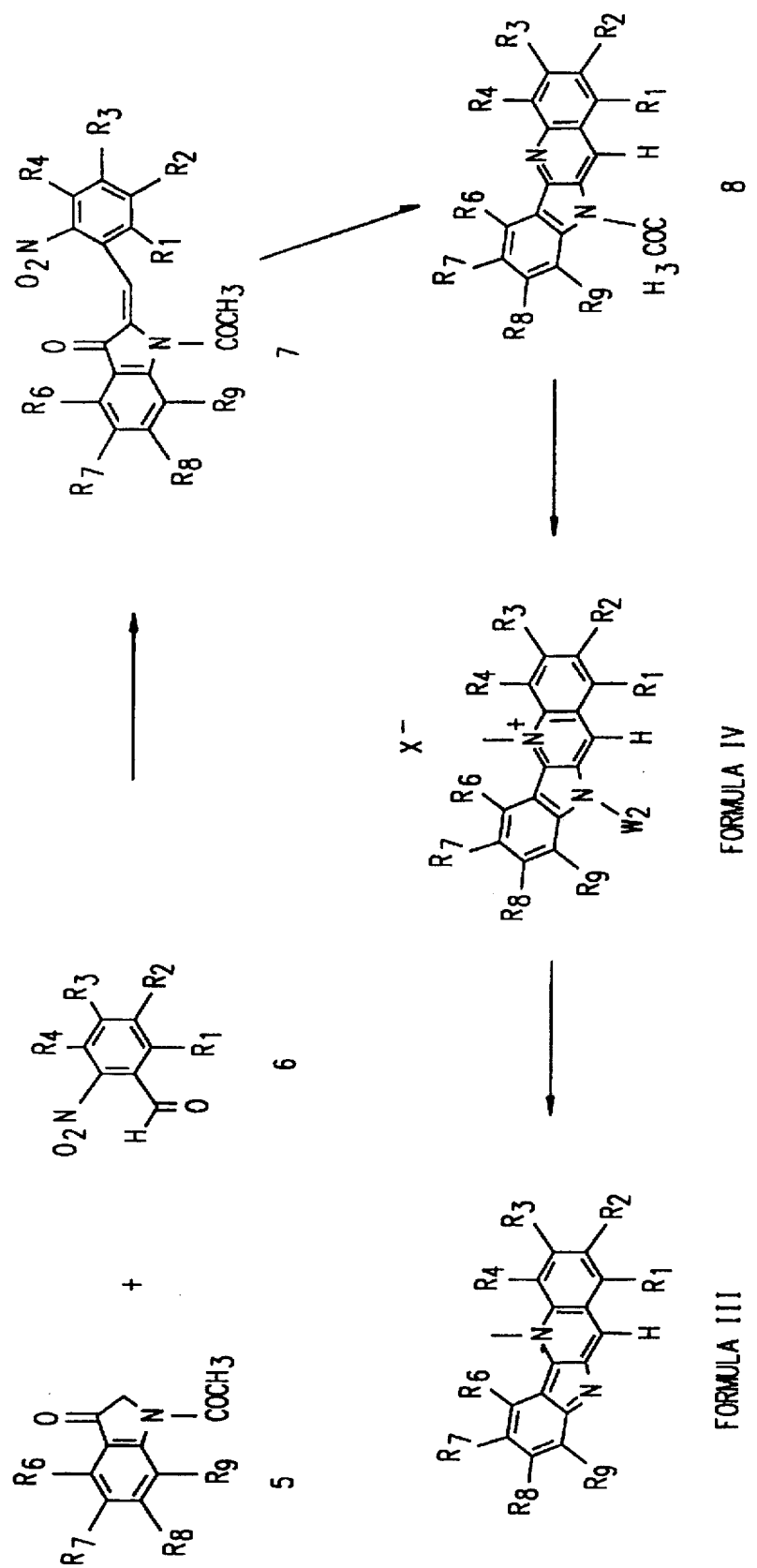
FIG. 2 is a flow chart describing a general preparation of cryptolepines of Formulae III and IV from nitrobenzaldehydes and indolines. $R_1$–$R_4$, $R_6$–$R_9$ and $R_{11}$ are defined above in Section 3; $W_2$=$CH_3CO$ and H; and $X^-$ is halogen, $CH_3SO_3^-$, $CH_3OSO_3^-$ and $CF_3SO_3^-$.

Cryptolepines of Formulae III and IV can also be prepared as described in FIG. 2 from suitably substituted nitrobenzaldehydes and suitably substituted indolines. The condensation of substituted indolines 5 with substituted nitrobenzaldehydes 6 is carried out in a nonpolar organic solvent, preferably benzene or toluene, in the presence of a catalytic amount of base, preferably an organic amine base and most preferably piperidine, providing quindoline precursor 7 [Merour, J. Y.; Coadou, J. Y.; Tatibouet, F. *Synthesis* 1982, 1053]. Preferably the conversion of 6 to 7 is performed in an inert atmosphere. Hydrogenation of 7 provides quindolines 8. Alkylation of quindolines 8, as described above for the alkylation of quindolines 4, provides the quindolinium iodides of Formula IV. The conversion of cryptolepines of Formula IV into cryptolepines of Formula III is performed as described above.

Figure 3:
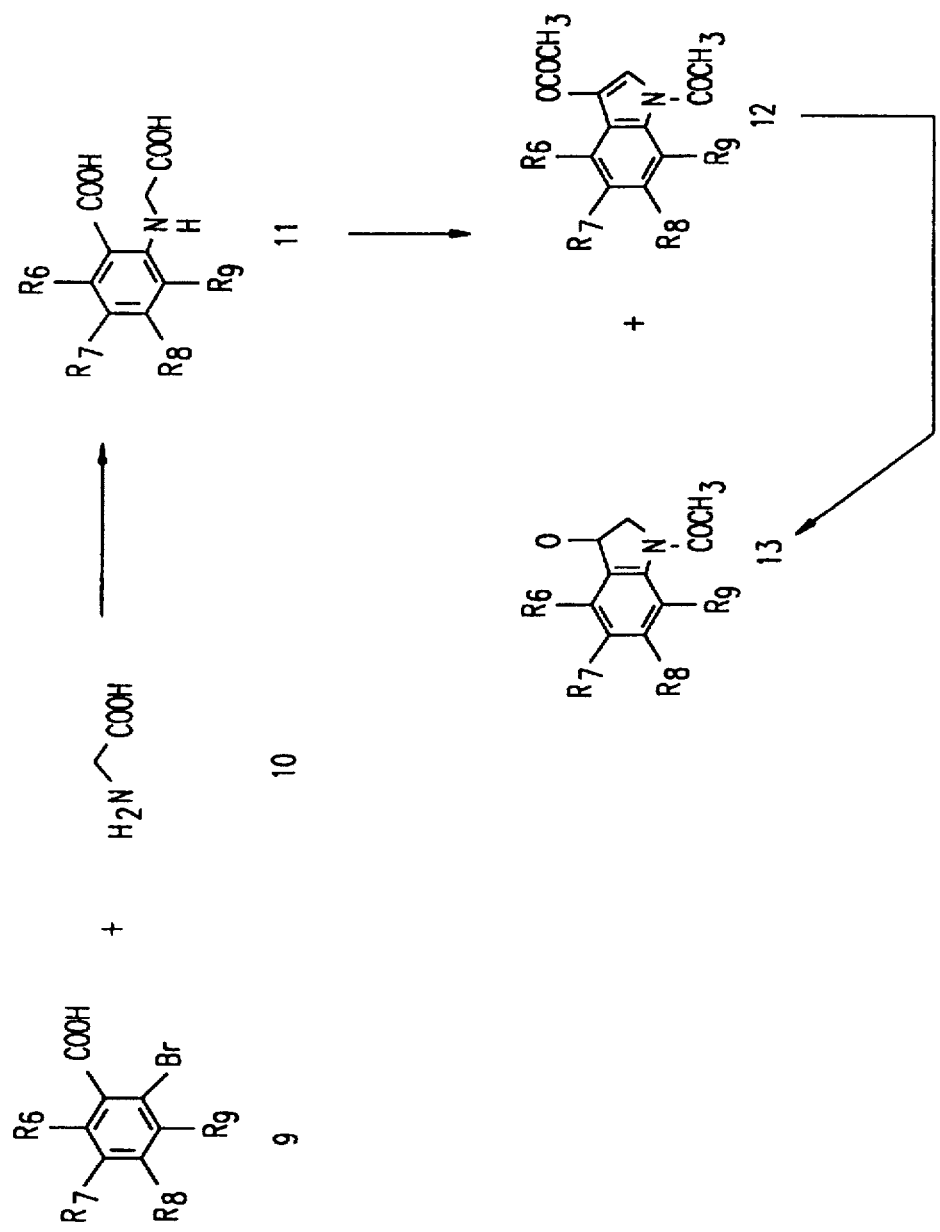
FIG. 3 is a flow chart describing a general preparation of indolines from benzoic acids. $R_6$–$R_9$ are defined above in Section 3.

The requisite indolines 1 and 5 used for the preparation of cryptolepines of Formulae III and IV described in FIGS. 1 and 2 can be obtained commercially or obtained by synthesis using the general description shown in FIG. 3 from modified literature procedures [(1) Merour, J. Y.; Coadou, J. Y.; Tatibouet, F. *Synthesis* 1982, 1053; (2) Nenitzescu, C. D.; Raileanu, D. *Chem. Ber.* 1958, 91, 1141]. Suitably substituted bromobenzoic acids 9 are condensed with glycine to provide anthranilic acids 11, preferably in the presence of CuBr catalyst. The conversion of 9 and 10 to 11, is preferably carried out in the presence of a base, preferably a member of the alkali metal or alkaline earth hydroxides, hydrogen carbonates or carbonates, and most preferably KOH or $K_2CO_3$ as base. Useful solvents include polar organic solvents and preferably, water. Preferably, the reaction is performed at reflux temperatures and/or under pressure in a pressure vessel. Cyclization of anthranilic acids 11 using conventional dehydration means, preferably a mixture of acetic anhydride and sodium acetate in refluxing DMF provides indole diacetates 12 (i.e., indoline 1, wherein $W_1=CH_3CO$). The cyclization reaction is performed in a polar organic solvent, preferably dimethylformamide, at a temperature exceeding room temperature, preferably at reflux. O-Deacetylation of indoles 12 to indoles 13 (i.e., indoline 5) is preferably accomplished using sodium sulfite in aqueous ethanol under reflux conditions [Galun, A.; Kampf, A.; Markus, A. *J. Heterocyclic Chem.* 1979, 15, 641].

The requisite isatins 2 (indole-2,3-diones) for the preparation of cryptolepines of Formula III and IV described in FIGS. 1 and 2 can be obtained commercially or obtained by synthesis using literature methods [(1) Yen, V. Q.; Buu-Hoi, N. P.; Xuong, N. D. *J. Org. Chem.* 1958, 23, 1858; (2) Sandmeyer, T. *Helv. Chim. Acta* 1919, 2, 237; (3) Sandmeyer, T. *Helv. Chim. Acta*, 1919, 2, 239; (4) Sumpter, W. C. *Chem Rev.* 1944, 34, 407; (5) Popp, F. D. *Adv. Heterocyclic Chem.* 1975, 18, 2–58].

Figure 4:
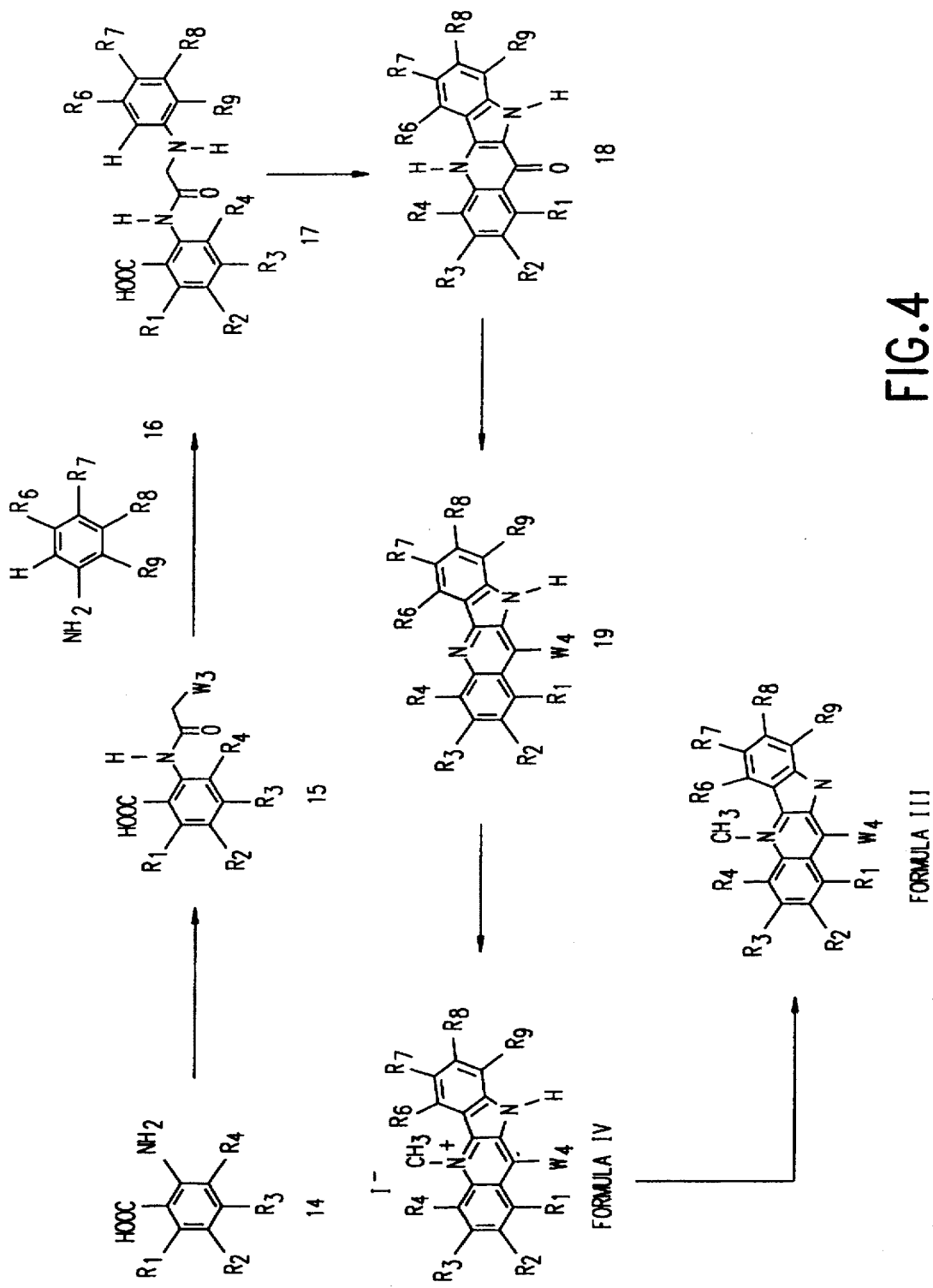
FIG. 4 is a flow chart describing a general preparation of cryptolepines of Formulae III and IV from anthranilic acids. $R_1$–$R_4$, $R_6$–$R_9$ and $R_{11}$ are defined above in Section 3; $W_3$=Br and Cl; $W_4$=Cl, Br and I.

Quindolines of Formulae III and IV can also be prepared as described in FIG. 4 from suitably substituted anthranilic acids 14. The general procedure outlined in FIG. 4 for the synthesis of quindolines 19 has been modified slightly from previously described procedures [(1) Yamato, M.; Takeuchi, Y.; Chang, M.-r.; Hashigaki, K. *Chem. Pharm. Bull.* 1992, 40, 528; (2) Yamato, M.; Takeuchi, Y.; Chang, M.-r.; Hashigaki, K.; Tsuruo, T.; Tashiro, T.; Tsukagoshi, S. *Chem. Pharm. Bull.* 1990, 38, 3048; (3) Takeuchi, Y.; Chang, M.-r.; Hashigaki, K.; Yamato, M. *Chem. Pharm. Bull.* 1991, 39, 1629; (4) Chang, M.-r.; Takeuchi, Y.; Hashigaki, K.; Yamato, M. *Heterocycles* 1992, 33, 147; (5) Takeuchi, Y.; Chang, M.-r.; Hashigaki, K.; Tashiro, T.; Tsuruo, T.; Tsukagoshi, S.; Yamato, M. *Chem. Pharm. Bull.* 1992, 40, 1481; (6) Görlitzer, K.; Stockmann, R.; Walter, W. D. *Pharmazie*, 1994, 49, 231]. Suitably substituted anthranilic acids 14 are acylated with chloroacetyl chloride or bromoacetyl bromide in a polar solvent such as DMF, dioxane, or DMF/dioxane mixtures to provide acylanthranilic acids 15 [(1) Ossman, A. E.; El-Zahabi, M. M.; El-Hakim, A. E.; Osman, A. N. *Egypt. J. Chem.* 1988, 31, 381; (2) Uskokovic, M. R.; Wenner, W. U.S. Pat. No. 3,374,264]. Amination of acylanthranilic acids 15 with suitably substituted anilines 16 provides anthranilic acid derivatives 17. Presumed Bischler-Napieralski reaction [(1) Görlitzer, K.; Weber, J. *Arch. Pharm.* (Weinheim) 1981, 314, 852; (2) Bischler, A.; Napieralski, B. *Chem. Ber.* 1893, 26, 1903; (3) Govindochari, T. R. *Org. React.* 1951, 6, 74] and subsequent cyclization using an acid such as polyphosphoric acid provides quindolines 18. Preferably, the ratio of polyphosphoric acid (PPA) to anthranilic acid derivates 17 is approximately 10:1 (ww), the reaction temperature is between 100°–120° C., and an aqueous triturative workup is used to remove phosphorous-derived impurities. Haloquindolines 19 are prepared by treatment of quindolones 18 with dehydrohalogenating agents such as $POCl_3$, $PCl_5$, mixtures of $POCl_3$ and $PCl_5$ or $PBr_3$. Preferably, mixtures of $POCl_3$ or $POCl_3/PCl_5$ mixtures are used. Alkylation of quindoline 19 with conventional methylating agents, such as those methods recited above, preferably under pressure in a pressure vessel, provides the quindolinium iodides of Formula IV. Preferably, the methylating agent is methyl iodide. The alkylation is performed in a polar organic solvent, preferably an alcoholic solvent and most preferably methanol. Most preferably, the pressure vessel is a teflon-lined Parr bomb. Under these conditions, trans-halogenation occurs, providing 11-iodocryptolepines of Formula IV. Other preferred methods for alkylating quindolines 19, some of which avoid trans-halogenation, are described in FIG. 5. The free base of Formula IV, represented by Formula III, can be prepared by those methods described above.

Figure 5:
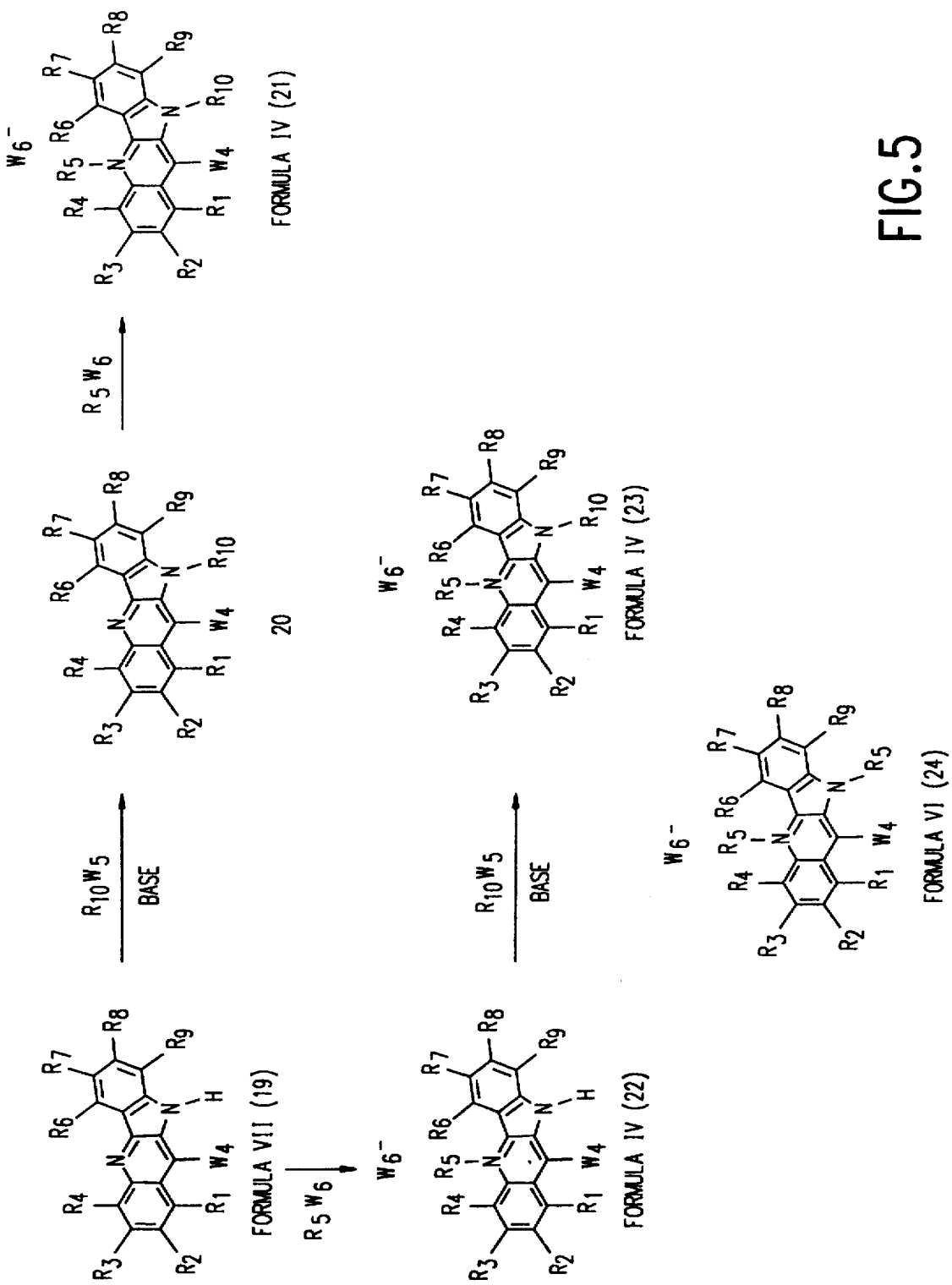
FIG. 5 is a flow chart describing a general preparation of cryptolepines of Formula IV from quindolines of Formula VII. $R_1$–$R_4$, $R_6$–$R_9$ and $R_{11}$ are defined above in Section 3; $W_4$=Cl, Br and I; $W_5$=Cl, Br, I, $OSO_2Me$ and $OSO_2CF_3$; $W_6$=Cl, Br, I, $OSO_2Me$ and $OSO_2CF_3$.

FIG. 5 outlines a general process for preparing cryptolepine analogs of Formula IV from quindolines 19. Alkylation of 19 with an alkylating agent ($R_{10}W_5$) such as an alkyl or aralkylhalide, a dialkyl or diaralkylsulfate, or an alkyl or aralkyltriflate in the presence of base provides 10-alkyl or aralkylquindolines 20. Preferably, the alkylating agents are aralkyl bromides, aralkyl iodides, alkyl iodides, and alkyl triflates. Preferred bases include NaOH, KOH, $Na_2CO_3$, and $K_2CO_3$. The 10-alkyl and 10-aralkyl quindolines 20 can be subsequently alkylated at the N-5 position using an alkylating agent ($R_5W_6$), preferably an alkyl halide or an aralkylhalide, in a pressure vessel to provide dialkylated cryptolepines 21. Alkylation of the quindolines 19 at the N-5 position can be effected by treatment with an alkyl halide or an aralkyl halide ($R_5W_6$), preferably in a pressure vessel, to provide quindolines of Formula IV (22). The preferred alkyl and aralkyl halides are the aralkyl bromides, aralkyl iodides, alkyl iodides. Preferred solvents used in the alkylation of 19 to 22 include chloroform, methylene chloride, toluene, and benzene.

Alternatively, as further illustrated in FIG. 5, cryptolepines 21 and 22 can be prepared from quindolines 20 and 19, respectively, using an alkylating agent, preferably a dialkylsulfate, in an inert solvent such as benzene or toluene at room temperature (rt) or reflux. N-5 cryptolepines 21 and 22 can also be prepared using an alkyl trifluoromethanesulfonate in an inert organic solvent, such as benzene or toluene. The use of a dialkyl sulfate or alkyl trifluoromethanesulfonate alkylating agent avoids trans-halogenation from occurring with quindolines 19 when $W_4$=halogen. Suitable solvents used in the alkyl trifluoromethanesulfonate alkylation at N-5 of 19 and 20 include dichloromethane, dichloroethane, chloroform, benzene, toluene, xylene, diethyl ether, diisopropyl ether, t-butyl methyl ether, t-butyl ethyl ether, ethylene glycol dimethyl ether, dimethylformamide, and mixtures thereof. Preferably, dichloromethane, dichloroethane, chloroform, benzene, or toluene is used. The reaction is run preferably between a temperature of 0° C. and rt. Preferably, 1 to 2 equivalents of alkyl trifluoromethanesulfonate is used.

Di-N-alkylated cryptolepine analogs 24 can be prepared from quindolines 19 under forcing conditions using excess alkyl trifluoromethanesulfonate reagent and elevated temperatures, typically reflux conditions. Alternatively, N-5 alkylated cryptolepine 22 can be alkylated with a different alkylating agent, such as $R_{10}W_5$ to form differentially dialkylated cryptolepine 23, wherein $R_{10}$ is defined above in Section 3 and $W_5$ is defined above in Section 4.

Figure 6:
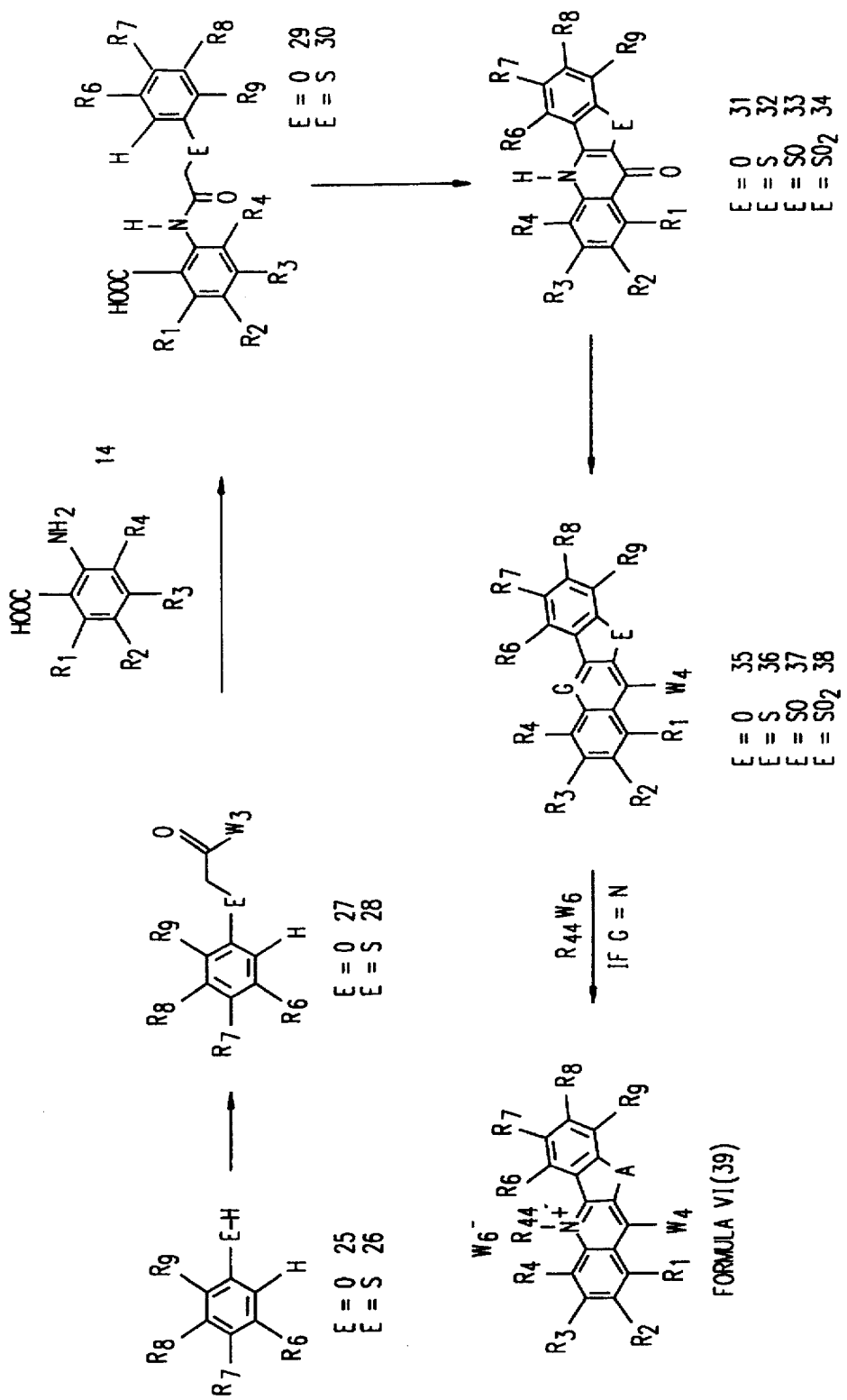
FIG. 6 is part 1 of a flow chart describing a general preparation of cryptolepine analogs of Formula VI. $R_1$–$R_4$, $R_6$–$R_9$, $R_{11}$ and A are defined above in Section 3, except that A≠$CH_2$; B=O, S, SO and $SO_2$; $W_3$=Br and Cl; $W_4$=Cl, Br and I; $W_6$=Cl, Br, I, $OSO_2Me$ and $OSO_2CF_3$; and G=N or $N^+$-$O^-$.

FIG. 6 outlines the preparation of cryptolepine analogs of Formula VI, wherein the N-$R_{10}$ substituent of 23 (FIG. 5) has been replaced with a heteroatom. For the preparation of Formula VI precursors 33 and 34, novel procedures are used. Previous literature methods used for the preparation of Formula VI precursors include: [(1) Yamato, M.; Hashigaki, K. EP 0376166; (2) Yamato, M. U.S. Pat. No. 4,826,850; (3) Sunder, S.; Peet, N. P. *J. Heterocyclic Chem.* 1978, 15, 1379; (4) Gorlitzer, K.; Weber, J. *Arch. Pharm* (Weinheim) 1980, 314, 76.]. Suitably substituted phenoxyacetyl chlorides 27 can be obtained commercially or synthetically from condensation with suitably substituted phenols 25 and halogenated acetic acids such as chloroacetic acid or bromoacetic acid, followed by conversion to the corresponding acid halides using thionyl chloride, thionyl bromide, or others methods used to prepare acid halides known to those skilled in the art. The phenoxyacetyl chlorides 27 are treated with suitably substituted anthranilic acids 14 under Schotten-Baumann conditions to provide anthranilic acids 29. Cyclization of the anthranilic acids 29 using an acid, preferably polyphosphoric acid, provides quinolones 31. Quinolones 31 are then treated with dehydrohalogenating agents such as $POCl_3$, $PCl_5$, mixtures of $POCl_3/PCl_5$ or $PBr_3$ to provide fused haloquinolines 35 (G=N). Haloquinolines 35 can optionally be oxidized by peroxide reagents such as peracetic acid, performic acid, m-chloroperbenzoic acid or other reagents commonly used by those skilled in the art to provide haloquinolines N-oxides 35 (G=$N^+$-$O^-$).

The synthesis of fused quinolines 36 (G=N) begins with the suitably substituted thiophenols 26. Reaction of the thiophenols 26 by those methods used to convert 25 to 27 discussed above, provides the thiophenylacetyl chlorides 28. Reaction of the thiophenylacetyl chlorides with anthranilic acids 14 under Schotten-Baumann conditions to provide anthranilic acids 30. Cyclization of the anthranilic acids 30 using acid, preferably polyphosphoric acid, provides quinolones 32. Quinolones 32 are then treated with dehydrohalogenating agents such as POCl$_3$, PCl$_5$, mixtures of POCl$_3$/PCl$_5$ or PBr$_3$ to provide fused haloquinolines 36 (G=N). Haloquinolines 36 can optionally be oxidized by peroxide reagents such as peracetic acid, performic acid, m-chloroperbenzoic acid or other reagents commonly used by those skilled in the art to provide haloquinoline sulfoxide N- oxides 37 (G=N$^+$-O$^-$) and haloquinoline sulfone N-oxides 38 (G=N$^+$-O$^-$). Optionally, the haloquinoline sulfoxide N-oxides 37 (G=N$^+$-O$^-$) and haloquinoline sulfone N-oxides 38 (G=N$^+$-O$^-$) can be treated with triphenylphosphine or with other reagents commonly used by those skilled in the art to reduce N-oxide functionality to provide sulfoxides 37 and sulfones 38, wherein G=N. Alternatively, sulfoxides 37 and sulfones 38 can be prepared from fused quinoline 36 without N-oxidation using potassium permanganate/acetic acid [Bierer, D. E.; O'Connell, J. F.; Parquette, J. R.; Thompson, C. M.; Rapoport, H. *J. Org. Chem.* 1992, 57, 1390]. Alternatively still, quinolone sulfoxide 33 and quinolone sulfone 34 can be prepared from quinolone 32 using those oxidizing agents useful for converting 36 to 37 or 38, described above. Subsequent treatment of 33 or 34 with POCl$_3$, PCl$_5$ mixtures of POCl$_3$/PCl$_5$, or PBr$_3$ provides fused quinolines 37 and 38, wherein G=N, respectively. Fused quinolines 35–38, wherein G=N, can be alkylated with R$_{44}$W$_6$, as described above in FIG. 5, wherein R$_{44}$ and W$_6$ are described above in Section 4, to provide quindolines of Formula VI (39) as described above.

Alternative literature methods can be used to synthesize fused quinolones 31, 32 and 34, and quinolines 35, 36, and 38 [(1) Görlitzer, K.; Weber, J. *Arch. Pharm* (Weinheim) 1980, 313, 27; (2) Görlitzer, K.; Weber, J. *Arch. Pharm* (Weinheim) 1980, 314, 76; (3) Görlitzer, K. *Arch. Pharm* 1976, 309, 18].

Figure 7:
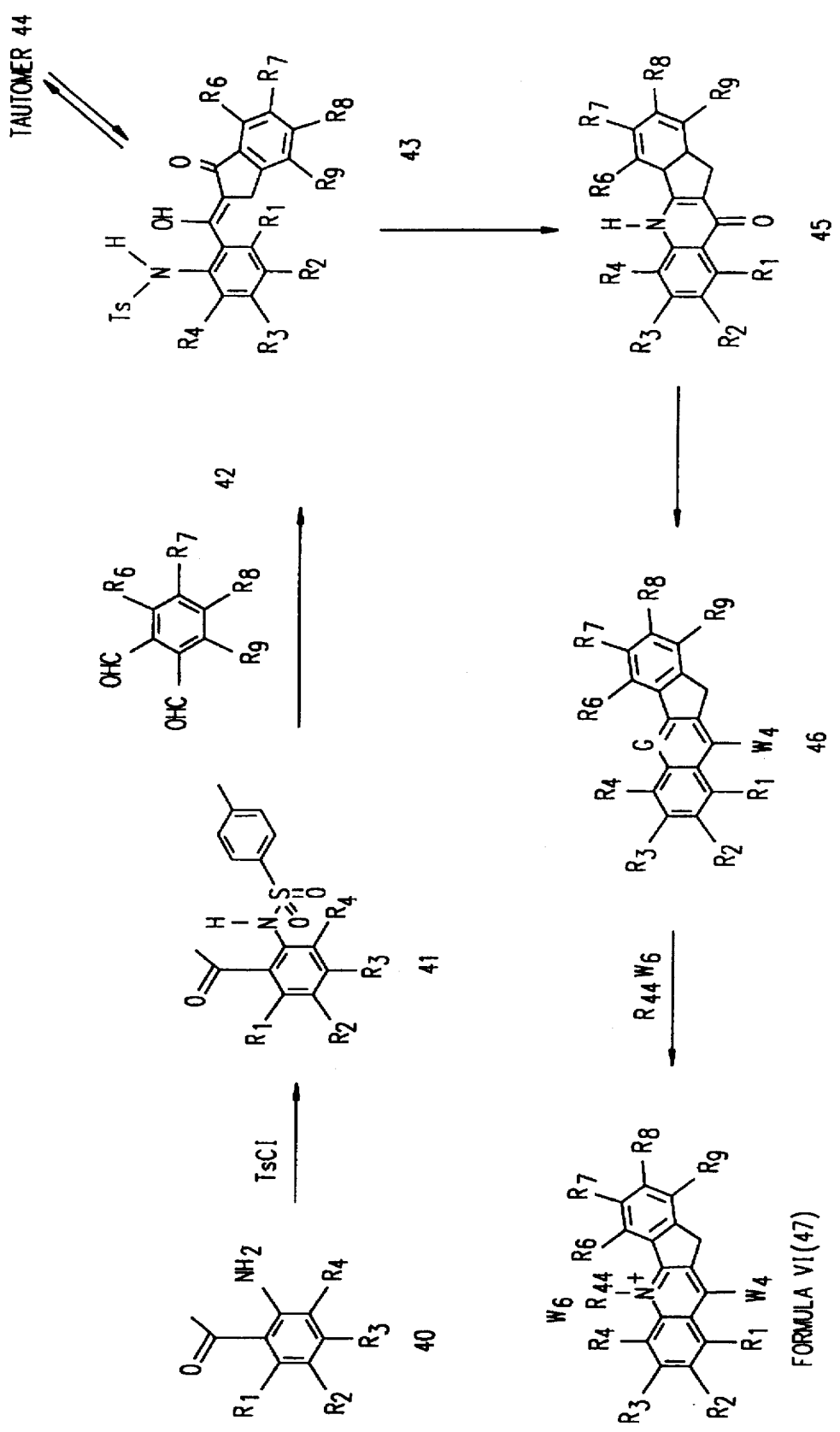
FIG. 7 is an additional flow chart describing a general preparation of cryptolepine analogs of Formula VI. $R_1$–$R_4$, $R_6$–$R_9$ and $R_{11}$ are defined above in Section 3; $W_3$=Br and Cl; $W_4$=Cl, Br and I; $W_6$=Cl, Br, I, $OSO_2Me$ and $OSO_2CF_3$; and G=N or $N^+$-$O^-$.

FIG. 7 outlines the preparation of cryptolepine analogs of Formula VI where A=CH$_2$, using a modified literature procedure [Görlitzer, K.; Weber, J. *Arch. Pharm* (Weinheim) 1979, 312, 254]. Suitably substituted amino acetophenones 40 are treated with tosyl chloride to provide N-tosylamino acetophenones 41. Thiele-Falk condensation reaction of N-tosylamino acetophenones 41 with suitably substituted dialdehyde 42 provides indanone 43 which can exist as its tautomer 44 or as a mixture of the two tautomeric forms. Acid promoted cyclization of 43, preferably using polyphosphoric acid, provides fused quinolones 45. Treatment of the fused quinolones 45 with dehydrohalogenating reagents such as POCl$_3$, PCl$_5$, mixtures of POCl$_3$/PCl$_5$ or PBr$_3$ provides haloquinolines 46, wherein G=N. Haloquinolines 46, wherein G=N, can optionally be oxidized by peroxide reagents such as peracetic acid, performic acid, m-chloroperbenzoic acid or other reagents commonly used by those skilled in the art to provide fused quinoline N-oxides 46 (G=N$^+$-O$^-$). Alternatively, fused quinolines 46, wherein G=N can be alkylated with R$_{44}$W$_6$ as described above in FIG. 5, wherein R$_{44}$ and W$_6$ are described above in Section 4, to provide cryptolepines analogs of Formula VI (47).

Alternative literature methods can be used to synthesize fused quinolones 46 [(1) Yamato, M.; Hashigaki, K. EP 0376166; (2) Görlitzer, K. *Arch. Pharm* 1976, 309, 18; (3) Schoen, J.; Bogdanowicz- Szwed, K. *Rocz. Chem.* 1964, 38, 425; C. A. 1964, 61, 1828b; (4) Blount, B. K.; Perkin, W. H.; Plant, S. G. P *J. Chem. Soc.* 1929, 1975].

Figure 8:
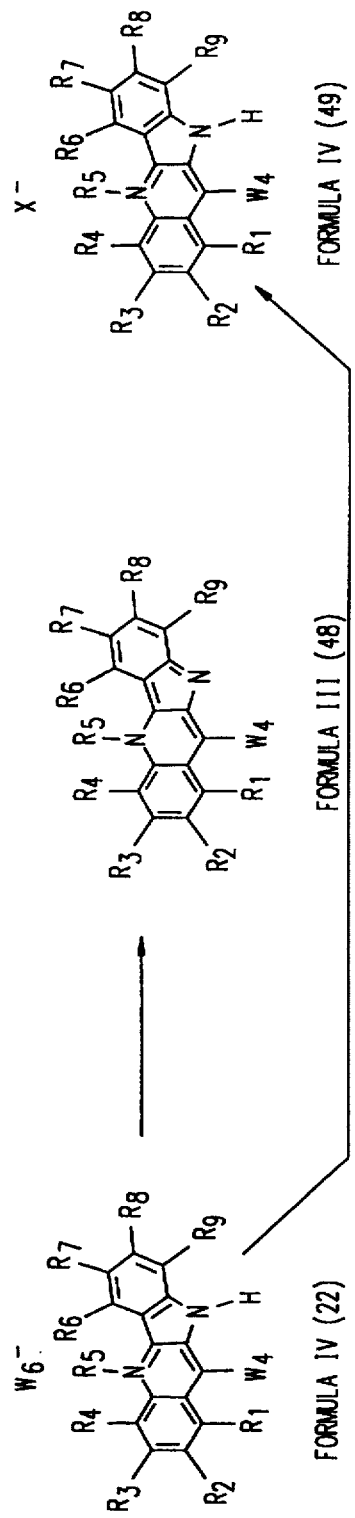
FIG. 8 is a flow chart describing a general preparation of cryptolepine analogs of Formulae III, IV and VI from cryptolepine analogs of Formulae IV and VI. $R_1$–$R_4$, $R_6$–$R_9$, $R_{11}$, $R_{44}$, A and $X^-$ are defined above in Section 3; $W_4$=Cl, Br and I; $W_6$=Cl, Br, I, $OSO_2Me$ and $OSO_2CF_3$.

FIG. 8 outlines a general procedure for preparing the free base of Formula IV cryptolepine analogs and for effecting counterion exchange for cryptolepine analogs of Formulae IV and VI. Formula IV cryptolepines 22 can be converted to their free base forms (48) by treatment with an aqueous basic solution, wherein the base is preferably Na$_2$CO$_3$, K$_2$CO$_3$, KOH, or NaOH, to provide cryptolepines of Formula III. Other aqueous solutions of bases commonly employed in the art may also apply. The conversion of cryptolepines 22 into cryptolepines 48 is most preferably achieved by adsorbing the quindolinium salts 22 onto a solid basic support, pouring the adsorbate on a basic alumina column and eluting with a polar organic solvent system, preferably ethanol-free chloroform, to remove any unalkylated quindoline impurities. Elution, preferably with methanol-chloroform and most preferably with 0.5–5% methanol-chloroform, provides cryptolepines of Formula III. Preferably, the solid basic support is Na$_2$CO$_3$.

Cryptolepines 48 can optionally be treated with an acid to provide cryptolepine salts 49. Alternatively, cryptolepines 22 can be converted to alternative salt forms using ion exchange technology commonly employed in the art to provide cryptolepine salts 49. Dialkylated cryptolepines 23 and Formula VI alkylated quinolines 39 can be converted to alternative salt forms using ion exchange technology commonly employed in the art to provide cryptolepine salts 50 and cryptolepine salts 51, respectively.

FIG. 9 outlines a general procedure for the preparation of 11-substituted cryptolepine analogs from cryptolepines 52. The procedures described are modifications of literature methods [(1) Görlitzer, K.; Weber, J. *Arch. Pharm.* (Weinheim) 1982, 315, 532; (2) Yamato, M.; Takeuchi, Y.; Chang, M.-r.; Hashigaki, K.; Tsuruo, T.; Tashiro, T.; Tsukagoshi, S. *Chem. Pharm. Bull.* 1990, 38, 3048; (3) Yamato, M; Takeuchi, Y.; Hashigaki, K.; Ikeda, Y.; Chang, M.-r.; Takeuchi, K.; Matsushima, M.; Tsuruo, T.; Tashiro, T.; Tsukagoshi, S.; Yamashita, Y.; Nakano, H. *J. Med. Chem.* 1989, 32, 1295; (4) Takeuchi, Y.; Chang, M.-r.; Hashigaki, K.; Yamato, M. *Chem. Pharm. Bull.* 1991, 39, 1629; (5) Chang, M.-r.; Takeuchi, Y.; Hashigaki, K.; Yamato, M. *Heterocycles* 1992, 33, 147; (6) Takeuchi, Y.; Chang, M.-r.; Hashigaki, K.; Tashiro, T.; Tsuruo, T.; Tsukagoshi, S.; Yamato, M. *Chem. Pharm. Bull.* 1992, 40, 1481; (7) Görlitzer, K.; Stockmann, R.; Walter, R. D. *Pharmazie* 1995, 50, 105]. Treatment of quindolines 52 with halide nucleophiles such as iodide, chloride, or bromide provides trans-halogenated cryptolepine analogs 53. Treatment with nucleophiles such as azide or cyanide ion provides the corresponding 11-substituted azido and cyano cryptolepine analogs 53. Treatment with phenols or phenolate anions provides the 11-substituted phenoxide cryptolepine analogs 53. Treatment with anilines or deprotonated anilines provides 11-substituted aminophenyl cryptolepine analogs 53. Treatment with thiophenols or thiophenolates provides the corresponding thiophenyl cryptolepine analogs 53. Treatment with organometallic reagents such as alkyl lithiums, alkyl potassiums, alkyl sodiums, or alkyl Grignard reagents provides the corresponding 11-alkylated cryptolepine analogs 53. Treatment with organometallic reagents such as aryl lithiums, aryl potassiums, aryl sodiums, or aryl Grignard reagents provides the corresponding 11-aryl cryptolepine analogs 53.

In an alternate embodiment of the invention, cryptolepine analogs having hypoglycemic activity are obtained by a novel method of synthesis which comprises alkylating a compound of Formula VII with methyl trifluoromethanesulfonate. The alkylation reaction is performed by dissolving or suspending a compound of Formula VII in an organic solvent and adding to the resulting solution or suspension 1–10 equivalents, preferably 2–5 equivalents, of methyl trifluoromethanesulfonate. Reaction temperatures can vary from −78° C. to reflux temperatures, preferably from −78° C. to room temperature and most preferably from −78° C. to 0° C. Suitable organic solvents useful include, but are not limited to diethyl ether, methylene chloride, chloroform, benzene, toluene and xylene. The alkylation reaction is optionally performed in the presence of an organic base such as triethylamine, pyridine, dimethylaminopyridine, Hünig's base, lutidine and the like. Optionally, the alkylation reaction can be performed using biphasic conditions, preferably using mixtures of chlorinated hydrocarbon solvents and water. When biphasic conditions are used, it is preferable to use as a base an alkali metal or alkaline earth hydroxide, hydrogen carbonate or carbonate.

The progress of the alkylation reaction of the compounds of Formula VII with methyl trifluoromethanesulfonate can be monitored by chromatography, such as thin-layer chromatography, or any other such techniques known to those skilled in the art.

5.2 METHODS FOR USE OF CRYPTOLEPINE ANALOGS

Due to the potent activity of the cryptolepine analogs of the present invention, cryptolepine analogs are advantageously useful in veterinary and human medicine for therapeutic treatment of diabetes mellitus. Additionally, the cryptolepine analogs can be advantageously be used as hypoglycemic agents to reduce the blood glucose level in situations of acute stress such as experienced by animals or patients with hyperthermia, trauma, sepsis, and burns and undergoing general anesthesia. Hyperglycemia sometimes associated with severe head injury, cerebral thrombosis, encephalitis and heat stroke can also be therapeutically treated with these cryptolepine analogs. Additionally, the cryptolepine analogs are useful as hypoglycemic agents for rare congenital metabolic glycogen storage disease associated with hyperglycemia.

Although the present inventors do not wish to be limited to any particular mechanism of action to explain the hypoglycemic activity of the cryptolepine analogs of the present invention, it is envisaged that they may advantageously be useful for treatment of both insulin-dependent or type I diabetes (formerly termed juvenile-onset or ketosis-prone diabetes) and non-insulin-dependent or type II diabetes (formerly termed adult-onset, maturity-onset or nonketotic diabetes).

When administered to a mammal for veterinary use or to a human for clinical use, the cryptolepine analogs can be used alone, or may be combined with any physiologically acceptable carrier such as water, an aqueous solution, normal saline, or other physiologically acceptable excipient. In general, the dosage would range from about 10–1000 mg/kg/day, preferably about 10–250 mg/kg/day.

The cryptolepine analogs can be administered by a number of routes, including, but not limited to: orally, injection including, but not limited to intravenously, intraperitoneally, subcutaneously, intramuscularly, etc. The preferred route of administration is oral. Additionally, the cryptolepine analogs can be administered in conjunction with another hypoglycemic including such as insulin; a biguanide such as metformin or buformin; a sulfonylurea such as acetohexamide, chlorpropamide, tolazamide, tolbutamide, glyburide, glypizide or glyclazide; a thiazolidinedione such as troglitazone; an α-glycosidase inhibitor such as acarbose or miglatol; or a $\beta_3$-adrenoceptor agonist such as CL-316, 243, etc.

The cryptolepine analogs of the present invention can be administered in an effective amount either as free bases or pharmaceutically acceptable salts using counter ions such as acetate, iodide, chloride, bromide, fluoride, hydroxide, sulfate, hydrogensulfate, methanesulfonate, trifluoromethanesulfonate, toluenesulfonate, benzenesulfonate, phosphate, hydrogenphosphate, dihydrogenphosphate, succinate, ascorbate, tartrate, gluconate, benzoate, malate, fumarate, and citrate.

In addition, the cryptolepine analogs or pharmaceutically acceptable salts thereof can be used for research purposes, for example, to investigate the mechanism and activity of hypoglycemic agents.

The following series of Examples are presented by way of illustration and not by way of limitation on the scope of the invention.

The following Examples are set forth to assist in understanding the invention and should not, of course, be construed as specifically limiting the invention described and claimed herein. Such variations of the inventions which would be within the purview of those in the art, including the substitution of all equivalents now known or later developed, including changes in formulation or minor changes in experimental design, are to be considered to fall within the scope of the invention as hereinafter claimed.

6. EXAMPLE: SYNTHESIS OF CRYPTOLEPINE ANALOGS

6.1 MATERIALS AND METHODS

Tetrahydrofuran (THF) was distilled from potassium/benzophenone; benzene, toluene, and methylene chloride were distilled from calcium hydride. Anhydrous dimethylformamide (DMF) and anhydrous chloroform were obtained from Aldrich. Methyl triflate was distilled prior to use and stored in a Schlenk flask under nitrogen. All other reagents were used as received. All moisture sensitive reactions were done under a nitrogen atmosphere, using dry solvents; air sensitive reactions were done under a nitrogen atmosphere. Evaporation of solvents was done at room temperature unless otherwise noted. Low pressure liquid chromatography (LPLC) for cryptolepine intermediates was performed on E. Merck 230–400 mesh silica gel using nitrogen pressure unless otherwise noted. Chromatography on the cryptolepine analogs was performed on Fisher Activity I basic alumina using ethanol-free chloroform. Preparative High-Performance Liquid Chromatography (HPLC) on cryptolepine analogs was performed using a Rainin HPLC equipped with two SD-1 pumps and UV-1 detector, with detection at 254 nm, and using a Hamilton PRP-1 reverse-phase column with an acetonitrile-water solvent gradient with 0.5% HCl. Analytical HPLC on cryptolepine analogs was performed on a Rainin HPLC equipped with two SD-1 pumps, a PDA-1 diode array detector, and a Sedex 55 light scattering detector, using a Hamilton PRP-1 reverse-phase column using an acetonitrile-water solvent gradient with 0.5% HCl. $^1$H and $^{13}$C NMR were provided by the Shaman Pharmaceutical Physical Chemistry Department using a Varian 400 MHz spectrometer with chloroform as an internal reference unless otherwise noted. NMR shifts were expressed in ppm downfield from internal tetramethylsilane. NMR assignments were determined on the basis of COSY, NOESY, HMQC, HMBC and DEPT experiments performed on selected intermediates. NMR coupling constants are reported in Hertz. Mass spectrometry was performed by the Physical Chemistry Department at Shaman Pharmaceuticals. Melting points were determined using a Buchi model 535 melting point apparatus and are uncorrected.

6.2 CRYPTOLEPINE ANALOGS SYNTHESIZED

Example 1

Quindoline-11-carboxylic acid

In a 3-necked flask containing O-acetylindoxyl (25 g, 0.143 mol) was added under nitrogen with shaking a cooled solution of isatin 2 (21.25 g, 0.144 mol) in aqueous KOH (125.5 g KOH in 575 mL of water). The reaction mixture was stirred vigorously under nitrogen at room temperature for 3 days. The reaction mixture was diluted with water (250 mL) and then oxygen was bubbled through the mixture while it was heated for 20 min at 75°–80° C. The reaction mixture was filtered hot, the filtrate was diluted with ethanol (750 mL) to dissolve the formed precipitate, and then concentrated HCl was added to adjust the pH of the solution to 4. The precipitate was filtered, washed with hot water, ethanol and then dried, yielding 28.2 g (75.2%) of the title compound; $^1$H NMR (DMSO-$d_6$) δ 11.39 (s, 1H, NH), 9.14 (d, J=7.6, 1H), 8.35 (d, J=8.0, 1H), 8.25 (d, J=7.2, 1H), 7.77 (d, J=8.4, 1H), 7.67 (m, 4H), 7.32 (t, J=8.0, 1H); $^{13}$C NMR (DMSO-$d_6$) δ 167.94, 147.15, 144.43, 143.42, 132.12, 130.20, 129.41, 126.37, 125.77, 125.27, 123.82, 121.22, 120.60, 120.09, 112.47; MS (EI, m/z) 262.1 (M$^+$).

Example 2

Quindoline

A mixture of quindoline-11-carboxylic acid prepared in Example 1 (29.2 g, 0.111 mol) and diphenylether (300 mL) was refluxed for 6 hours, cooled to 30° C. and diluted with petroleum ether (250 mL). The precipitate which formed was filtered and washed with petroleum ether thoroughly, yielding 22.1 g (90.9%) of the title compound. A portion of this material was further purified by LPLC (ethyl acetate-hexane 1:3), mp 249°–251° C. [lit 251°–252° C. (Degutis, Y. A.; Ezyarskaite, A. B. *Khim. Geterotsik. Soedin.* 1986, 1375)]; $^1$H NMR (DMSO-$d_6$) δ 11.43 (s, 1H, NH), 8.36 (d, J=7.8, 1H), 8.29 (s, 1H), 8.19 (d, J=8.4, 1H), 8.10 (d, J=8.2, 1H), 7.67-7.53 (m, 4H), 7.27 (t, J=7.4, 1H); $^{13}$C NMR (DMSO-$d_6$) δ 145.72, 144.03, 143.39, 132.44, 129.68, 128.68, 127.48, 126.71, 126.01, 124.84, 121.34, 120.97, 119.33, 112.99, 111.49; MS (EI, m/z) 218.1 (M$^+$).

Example 3

5-Methylquindolinium Hydroiodide (Cryptolepine Hydroiodide)

A mixture of quindoline (2.0 g, 9.2 mmol) from Example 2, methanol (5 mL) and methyl iodide (880 mL, 14.1 mmol) was heated in a bomb at 120° C. for 4 hours. After cooling, the resulting brown precipitate (2.5 g, 75.5%) was filtered and washed with ether. Recrystallization from water gave the title compound as bright yellow crystals, yield 50%, mp 283.5°–284° C. [lit 284°–286° C. (Gellert, E.; Raymond-Hamet; Schlittler, E. *Helv. Chim. Acta* 1951, 34, 642–651)]; $^1$H NMR (DMSO-$d_6$) δ 12.87 (s, 1H, NH), 9.28 (s, 1H, H$_{11}$), 8.79 (d, J=8.4, 1H, H$_6$), 8.75 (d, J=9.2, 1H, H$_4$), 8.57 (d, J=8.3, 1H, H$_1$), 8.16 (t, J=7.6, 1H, H$_3$), 7.94-7.92 (dd, J=7.2, J=7.0, 2H, H$_2$ and H$_8$), 7.82 (d, J=8.4, 1H, H$_9$), 7.51 (t, J=7.0, 1H, H$_7$), 5.02 (s, 3H, NCH$_3$); $^{13}$C NMR (DMSO-$d_6$) δ 145.62, 137.97, 135.25, 133.87, 133.16, 132.34, 129.76, 126.99, 126.21, 126.13, 124.72, 121.31, 117.78, 113.76, 113.10, 40.19; MS (EI, m/z) 232.1 (M$^+$).

Example 4

5-Methylquindoline (Cryptolepine)

5-Methylquindolinium hydroiodide (1.5 g, 4.2 mmol) from Example 3 was shaken with a 5% solution of Na$_2$CO$_3$ (100 mL) and extracted with chloroform (2×200 mL). The extract of the free base was purified on a basic alumina column using chloroform to elute the quindoline impurity; elution with 1–2% methanol in chloroform gave 0.5 g of the title compound as a purple solid, mp 178°–180° C. [lit 166°–169° C. (Gellert, E.; Raymond-Hamet; Schlittler, E. *Helv. Chim. Acta* 1951, 34, 642–651)]; $^1$H NMR (DMSO-$d_6$) δ 8.92 (s, H$_{11}$), 8.50 (d, J=9.2, 1H, H$_4$), 8.47 (d, J=8.4, 1H, H$_6$), 8.38 (d, J=8.4, 1H, H$_1$), 7.89 (t, J=7.6, 1H, H$_3$), 7.69-7.64 (m, 2H, H$_2$ and H$_9$), 7.52 (t, J=8.4, 1H, H$_8$), 7.02 (t, J=8.4, 1H, H$_7$), 4.90 (s, 3H, NCH$_3$); $^{13}$C NMR (DMSO-$d_6$) δ 160.46, 144.76, 138.96, 132.56, 130.13, 129.47, 128.66, 126.15, 124.97, 124.26, 123.60, 119.30, 116.36, 116.23, 113.64, 38.73.

Example 5

5-Methylquindolinium Hydrochloride (Cryptolepine Hydrochloride)

5-Methylquindolinium hydroiodide (1.6 g, 4.4 mmol) from Example 3 was adsorbed onto sodium carbonate and loaded onto a basic alumina column. The column was eluted with chloroform to remove the quindoline impurities. Elution with 1–2% methanol in chloroform provided purple fractions which were concentrated to a small volume, and then acidified with a 1M solution of HCl in ether to afford a yellow-orange precipitate. The solid was filtered, washed with ether and dried to yield 0.72 g of the title compound, mp 268° C. [lit 263°–265° C. (Gellert, E.; Raymond-Hamet; Schlittler, E. *Helv. Chim. Acta* 1951, 34, 642–651)].

Example 6

5-Ethylquindolinium Hydroiodide and 5-Ethylquindolinium Hydrochloride

A suspension of quindoline (1 g, 4.6 mmol) from Example 2 and ethyl iodide (3 mL, 37.7 mmol) was heated in a bomb at 135° C. for 15 hours. The excess ethyl iodide was removed and the resulting brown precipitate was collected, washed with ether and dried, yielding 1.5 g (87.7%) of 5-ethylquindolinium hydroiodide. Recrystallization from water afforded bright yellow crystals of 5-ethylquindolinium hydroiodide, mp 256° C. [lit 222°–223° C. (Fichter, F.; Boehringer, R. *Ber* 1906, 3941)]; $^1$H NMR (DMSO-$d_6$) δ 12.93 (s, 1H, NH), 9.32 (s, 1H, H$_{11}$), 8.78 (d, J=9.2, 1H, H$_4$), 8.66 (d, J=8.4, 1H, H$_6$), 8.60 (d, J=8.0, 1H, H$_1$), 8.18 (t, J=7.6, 1H, H$_3$), 7.95 (dd, J=8.0, J=7.2, 2H, H$_2$ and H$_8$), 7.87 (d, J=8.4, 1H, H$_9$), 7.55 (t, J=7.6, 1H, H$_7$), 5.55 (q, J=6.8, 2H, NCH$_2$), 1.76 (t, J=7.2, 3H, CH$_3$); $^{13}$C NMR (DMSO-$d_6$) δ 145.78, 136.92, 134.34, 133.94, 133.52, 132.71, 130.06, 127.09, 126.42, 125.50, 125.14, 121.81, 117.31, 113.35, 112.80, 47.33, 13.30; MS (EI, m/z) 246 (M$^+$-1)

5-Ethylquindolinium hydroiodide (0.75 g, 2.0 mmol) obtained above was shaken in an aqueous 5% solution of sodium carbonate (100 mL), extracted with chloroform (2×250 ml) and concentrated to a small volume. Purification of the concentrate was accomplished on a basic alumina column, first eluting with chloroform to remove impurities and then eluting with 1–2% ethyl alcohol in chloroform to elute the free base. The resulting purple extract was evaporated to a small volume and acidified with a 1.0M HCl solution in ethyl ether to afford after filtration and drying, 300 mg (52.8%) of 5-ethylquindolinium hydrochloride as yellow crystals, mp 268.5°–269° C. (decomp.); $^1$H NMR (DMSO-$d_6$) δ 13.29 (s, 1H, NH), 9.34 (s, 1H, H$_{11}$), 8.79 (d, J=9.2, 1H, H$_4$), 8.66 (d, J=8.4, 1H, H$_6$), 8.61 (dd, J=1.6, J=8.4, 1H, H$_1$), 8.19 (t, J=7.6, 1H, H$_3$), 7.96 (t, J=7.2, J=8.0, 2H, H$_2$ and H$_8$), 7.90 (d, J=8.0, 1H, H$_9$), 7.56 (t, J=7.6, 1H, H$_7$), 5.56 (q, J=7.2, 2H, NCH$_2$), 1.76 (t, J=7.6, 3H, CH$_3$);

$^{13}$C NMR (DMSO-d$_6$) δ 145.88, 136.93, 134.34, 133.92, 133.60, 132.68, 130.11, 127.07, 126.44, 125.50, 125.18, 121.75, 117.30, 113.43, 112.79, 47.32, 13.29.

Example 7

5-Butylquindolinium Hydroiodide and 5-Butylquindolinium Hydrochloride

A suspension of quindoline (1 g, 4.6 mmol) from Example 2 and butyl iodide (3 ml, 26.4 mmol) was heated in a bomb at 140° C. for 16 hours and then cooled. The solid was filtered, washed thoroughly with ether, washed with 10% EtOH in ethyl ether and then dried to afford 5-butylquindolinium hydroiodide, 1.82 g (100%) as a brown solid. Recrystallization from water gave bright yellow crystals of 5-butylquindolinium hydroiodide, mp 252°–253° C.; $^1$H NMR (DMSO-d$_6$) δ 12.96 (s, 1H, NH), 9.34 (s, 1H, H$_{11}$), 8.77 (d, J=9.2, 1H, H$_4$), 8.61 (d, J=8.4, 1H, H$_6$), 8.54 (d, J=8.4, 1H, H$_1$), 8.19 (t, J=8.4, 1H, H$_3$), 7.96 (t, J=8.4, J=7.2, 2H, H$_2$ and H$_8$), 7.88 (d, J=8.4, 1H, H$_9$), 7.58 (t, J=7.2, 1H, H$_7$), 5.51 (t, J=7.2, 2H, N-CH$_2$), 2.09 (m, 2H), 1.69 (m, 2H), 1.00 (t, J=7.2, 3H, CH$_3$); $^{13}$C NMR (DMSO-d$_6$) δ 145.78, 137.07, 134.64, 133.93, 133.52, 132.71, 130.07, 127.11, 126.40, 125.38, 125.29, 121.88, 117.55, 113.47, 112.89, 51.29, 30.11, 19.22, 13.83; MS (EI, m/z) 275 (M$^+$).

5-Butylquindolinium hydroiodide (0.8 g, 2.0 mmol) obtained above was shaken with an aqueous 5% solution sodium carbonate solution, extracted with chloroform (2×250 ml), evaporated to a small volume and purified on alumina basic column, eluting first with chloroform to remove impurities and then eluting with 1–2% ethyl alcohol in chloroform to elute the free base. The resulting purple extract was evaporated to a small volume and acidified with a solution of 1.0M HCl in ethyl ether to afford 400 mg (63.5%) of 5-butylquindolinium chloride as yellow crystals, mp 253°–254° C.; $^1$H NMR (DMSO-d$_6$) δ 13.55 (s, 1H, NH), 9.35 (s, 1H, H$_{11}$), 8.76 (d, J=9.2, 1H, H$_4$), 8.61 (d, J=8.4, 1H, H$_6$), 8.52 (d, J=8.4, 1H, H$_1$), 8.17 (t, J=8.4, 1H, H$_3$), 7.94 (t, J=8.0, J=8.4, 2H, H$_2$ and H$_8$), 7.88 (d, J=8.4, 1H, H$_9$), 7.55 (t, J=8.0, 1H, H$_7$), 5.50 (t, J=7.6, 2H, N-CH$_2$), 2.08 (m, 2H), 1.69 (m, 2H), 1.00 (t, J=7.2, 3H, CH$_3$); $^{13}$C NMR (DMSO-d$_6$) δ 145.85, 136.94, 134.58, 133.81, 133.53, 132.63, 130.09, 127.02, 126.36, 125.34, 125.22, 121.76, 117.51, 113.48, 112.75, 51.27, 30.11, 19.22, 13.83.

Example 8

5-Benzylquindolinium Hydrobromide and 5-Benzylquindolinium Hydrochloride

A suspension of quindoline (1.0 g, 4.6 mmol) from Example 2, benzyl bromide (3 mL, 8.5 mmol) and chloroform (5 mL) was heated in a bomb at 140° C. for 48 hours. After cooling, the reaction mixture was dissolved in a small amount chloroform. Ether (100 mL) was added, and the resulting precipitate was filtered and washed with ether to give 1.78 g (100%) of 5-benzylquindolinium hydrobromide as a greenish-yellow solid. A portion of the 5-benzyl quindolinium hydrobromide (0.9 g) obtained above was purified by LPLC on neutral alumina (Fisher) eluting with 1–2% MeOH in CHCl$_3$. The product containing fractions were combined, redissolved in a small amount of chloroform, and acidified with a solution of 1.0M HCl in ether to give, after filtration and drying, 0.20 g (25%) of 5-benzylquindolinium hydrochloride as yellow crystals, mp 241°–242° C.; $^1$H NMR (DMSO-d$_6$) δ 13.40 (s, 1H, NH), 9.49 (s, 1H, H$_{11}$), 8.68 (d, J=8.2, 1H, H$_6$), 8.53 (d, J=8.8, 1H, H$_4$), 8.31 (d, J=8.4, 1H, H$_1$), 8.12 (t, J=6.4, 1H, H$_3$), 7.96 (t, J=7.6, 1H, H$_8$), 7.90 (d, J=5.2, 2H, H$_2$ and H$_9$), 7.42-7.32 (m, 4H, H$_7$ and arom), 7.22 (d, J=6.4, 2H), 6.84 (s, 2H, NCH$_2$); $^{13}$C NMR (DMSO-d$_6$) δ 146.14, 138.11, 135.21, 134.16, 133.84, 133.28, 133.00, 130.23, 129.19, 128.14, 127.21, 126.41, 126.10, 126.02, 125.24, 121.65, 117.59, 113.53, 112.86; MS (EI, m/z) 308.1 (M$^+$-1).

Example 9

10-Methylquindolinium Hydrochloride and 10-Methylquindoline

A mixture of powdered KOH (1.0 g, 17.8 mmol), BaO (2.8 g, 17.8 mmol), acetone (50 mL) and quindoline (1 g, 4.58 mmol) from Example 2 was refluxed for 1 hour, cooled to room temperature, and to it was added CH$_3$I (1.42 ml, 3.25 g, 22.9 mmol). The mixture was refluxed for 4 hours, cooled, filtered and the filtrate evaporated to dryness. The residue was extracted with ether (2×50 mL) and the ether solution was washed with water, dried over magnesium sulfate and then filtered. A stream of HCl gas passed through the solution and the solid product was collected to give after drying, 0.9 g (73.2%) of 10- methylquindolinium hydrochloride as a yellow solid.

The 10-methylquindolinium hydrochloride obtained above (250 mg, 0.9 mmol) was shaken with an aqueous 5% Na$_2$CO$_3$ solution (50 mL), extracted with ethyl ether (2×50 mL) and purified by HPLC (ethyl acetate-hexane 1:6) to give 100 mg (45.5%) of 10-methylquindoline; $^1$H NMR (CDCl$_3$) δ 8.56 (d, J=7.6, H, H$_8$), 8.34 (d, J=8.4, 1H, H$_4$), 7.94 (d, J=8.0, 1H, H$_1$), 7.85 (s, 1H, H$_{11}$), 7.69–7.61 (m, 2H, H$_3$ and H$_6$), 7.56 (t, J=7.2, 1H, H$_2$), 7.37 (d, J=8.4, 1H, H$_9$), 7.33 (t, J=7.6, 1H, H$_7$), 3.82 (s, 3H, CH$_3$); $^{13}$C NMR (CDCl$_3$) δ 145.89, 144.84, 143.92, 133.98, 129.60, 129.12, 127.08, 126.75, 126.12, 125.14, 121.96, 121.47, 119.58, 110.58, 108.34, 28.98; MS (EI, m/z) 232.1 (M$^+$).

Example 10

10-Butyloxycarbonylquindoline

To a suspension of quindoline (360 mg, 1.65 mmol) from Example 2 in acetonitrile (100 mL) was sequentially added a solution of NaOH (66 mg, 1.65 mmol) in water (2 mL) and di-tert-butyl dicarbonate (720 mg, 3.30 mmol). The reaction mixture was stirred at room temperature for 3 days, filtered, and the resulting filtrate was evaporated to dryness. Purification by LPLC (ethyl acetate-hexane 1:6) afforded 400 mg (76.3%) of the title compound as white crystals, mp 168° C.; $^1$H NMR (CDCl$_3$) δ 8.95 (s, 1H, H$_{11}$), 8.49 (d, J=7.6, 1H, H$_8$), 8.32 (d, J=8.6, 1H, H$_4$), 8.28 (d, J=8.6, 1H, H$_1$), 7.98 (d, J=8.0, 1H, H$_3$), 7.43 (t, J=6.8, 1H, H$_6$), 7.65 (t, J=7.4, 1H, H$_2$), 7.58 (t, J=8.2, 1H, H$_9$), 7.48 (t, J=7.2, 1H, H$_7$), 1.82 (s, 9H); $^{13}$C NMR (CDCl$_3$) δ 150.87, 147.23, 145.86, 141.52, 131.17, 130.50, 128.95, 128.39, 128.14, 127.35, 125.82, 124.90, 123.76, 121.54, 120.78, 116.23, 84.58, 28.40; MS (EI, m/z) 318.1 (M$^+$).

Example 11

Methylation of 10-Butyloxycarbonylquindoline

A mixture of 10-butyloxycarbonylquindoline (100 mg, 0.31 mmol) from Example 10, methyl alcohol (5 mL) and methyl iodide (45 mL, 0.70 mmol) was heated in a bomb at 120° C. for 4 hours. After cooling, the resulting yellow precipitate (93 mg, 82.3%) was filtered, washed with ethanol, then washed with ether and hexane to afford 5-methylquindolinium hydroiodide identical to that obtained above in Example 3.

Example 12

5,10-Dibenzylquindolinium Chloride

A suspension of quindoline (1 g, 4.58 mmol) from Example 2, benzyl bromide (3 mL, 25.1 mmol) and dry chloroform (5 mL) was heated in a bomb at 140° C. for 48 hours. A solution of aqueous 5% $Na_2CO_3$ (100 mL) was added and the reaction mixture was extracted with chloroform (2×250 mL). The extract was evaporated to dryness. The residue was purified on a basic alumina column eluting with 1–2% MeOH in $CHCl_3$, and the combined fractions were acidified with a solution of 1.0M HCl in ether and concentrated to afford 0.65 g (32.7%) of the title compound as an orange solid, mp 244.4°–244.7° C.; $^1H$ NMR (DMSO-$d_6$) δ 9.87 (s, 1H), 8.59 (d, J=8.0, 1H), 8.55 (d, J=9.2, 1H), 8.37 (d, J=8.4, 1H), 8.04–7.93 (m, 3H), 7.45 (t, J=7.2, 1H), 7.40-7.28 (m, 10 H), 6.87 (s, 2H), 6.06 (s, 2H); $^{13}C$ NMR (DMSO-$d_6$) δ 145.84, 138.05, 136.03, 135.36, 134.74, 134.46, 133.29, 133.14, 130.13, 129.19, 128.81, 128.18, 127.84, 127.65, 126.95, 126.49, 126.08, 125.63, 125.13, 122.13, 117.78, 113.11, 111.99, 55.17, 46.28; MS (LSIMS, m/z) 399 ($MH^+$).

Example 13

Methyl 10-Methylquindoline-11-carboxylate

A mixture of quindoline-11-carboxylic acid (2.6 g, 10 mmol) from Example 1, DMF (25 mL), KOH (2.24 g, 40 mmol), BaO (6.27 g, 40 mmol) and methyl iodide (9.7 mL, 130 mmol) was stirred at room temperature for 48 hours, then partitioned between benzene (60 mL) and water (100 mL). The benzene layer was washed with water (2×60 mL), dried and concentrated. The residue was recrystallized from hexane to afford 1.14 g (39.3%) of the title compound as light yellow crystals, mp 127° C.; $^1H$ NMR ($CDCl_3$) δ 8.49 (d, J=8.0, 1H), 8.31(d, J=8.0, 1H), 7.95 (d, J=8.4, 1H), 7.68-7.55 (m, 3H), 7.42 (d,J=8.0, 1H), 7.37 (t, J=7.2, 1H), 4.14 (s, 3H), 3.79 (s, 3H); $^{13}C$ NMR ($CDCl_3$) δ 167.98, 146.93, 145.64, 143.25, 130.27, 129.66, 126.52, 123.55, 122.92, 122.02, 121.28, 120.42, 115.77, 108.70, 52.71, 30.75; MS (EI, m/z) 290.1 ($M^+$).

Example 14

5,10-Dimethyl-11-(methoxycarbonyl)quindolinium Iodide

A solution of methyl 10-methylquindoline-11-carboxylate (0.5 g, 1.72 mmol) from Example 13 in methyl iodide (5 mL, 50.3 mmol) was stirred at room temperature for 48 hours. The excess of $CH_3I$ was removed in vacuo and the residue was dissolved in MeOH (10 mL). Diethyl ether (30 mL) was added and the precipitate was filtered and washed thoroughly with diethyl ether to afford, after drying, 0.33 g (44.6%) of the title compound as an orange solid, mp 257.0°–257.5° C. (decomp.); $^1H$ NMR (DMSO-$d_6$) δ 8.90 (dd, J=2.8, J=9.2, 2H), 8.33 (d, J=8.0, 1H), 8.24 (t, J=6.8, 1H), 8.10 (t, J=5.2, 2H), 8.04 (t, J=8.4, 1H), 7.62 (t, J=8.0, 1H), 5.08 (s, 3H), 4.31 (s, 3H), 3.99 (s, 3H); $^{13}C$ NMR (DMSO-$d_6$) δ 164.95, 148.00, 140.47, 135.11, 134.96, 132.61, 129.99, 128.74, 126.96, 125.76, 124.86, 122.31, 122.27, 118.72, 113.60, 111.71, 54.67, 41.20, 30.98; MS (LSIMS, m/z) 305 ($M^+$).

Example 15

Methyl Quindoline-11-carboxylate

To a suspension of quindoline-11-carboxylic acid (2.3 g, 8.77 mmol) from Example 1 in MeOH (50 mL) was added concentrated $H_2SO_4$ (1.5 ml, 28 mmol). The resulting solution was refluxed for 8 hours, cooled, and partitioned between benzene (100 mL) and water (50 mL). After adjusting the pH to 9 with a saturated solution of $K_2CO_3$, the benzene layer was separated, washed with water, dried and concentrated. Purification by LPLC (EtOAc-hexane 1:3) gave 0.28 g of the title compound as greenish-yellow crystals (from hexane), mp 152°–153.5° C. [lit 152.5°–154° C. (Degutis, Y. A.; Ezyarskaite, A. B. *Khim. Geterotsik. Soedin.* 1986, 1375)]; $^1H$ NMR ($CDCl_3$) δ 9.75 (s, 1H), 9.09 (d, J=6.4, 1H), 8.51 (d, J=8.0, 1H), 8.38 (d, J=7.2, 1H), 7.72-7.62 (m, 3H), 7.49 (d, J=8.0, 1H), 7.38 (t, J=8.0, 1H); $^{13}C$ NMR ($CDCl_3$) δ 168.19, 147.81, 144.43, 143.56, 133.91, 130.50, 130.27, 127.40, 126.18, 125.05, 123.66, 122.23, 121.65, 121.06, 111.19, 109.21, 52.54; MS (EI, m/z) 276 ($M^+$). Acidification of the water layer with HCl gave 1.8 g (78.3%) of recovered starting material.

Example 16

5-Methyl-11-(methoxycarbonyl)quindolinium Hydroiodide

A solution of methyl quindoline-11-carboxylate (0.16 g, 0.58 mmol) from Example 15 in methyl iodide (3 mL, 30.2 mmol) was stirred at rt for 48 hours. The excess of $CH_3I$ was removed in vacuo and the residue was washed thoroughly with diethyl ether to afford the 0.06 g (25.0%) of the title compound as a red solid, mp 246.5°–247.0° C.; $^1H$ NMR (DMSO-$d_6$) δ 12.70 (s, 1H, NH), 8.92-8.80 (m, 3H), 8.22 (t, J=8.0, 1H), 8.09-7.95 (m, 2H), 7.94 (d, J=8.0, 1H), 7.58 (t, J=7.6, 1H); $^{13}C$ NMR (DMSO-$d_6$) δ 164.01, 146.47, 141.01, 135.35, 135.14, 132.10, 131.94, 128.40, 126.89, 126.37, 122.88, 122.09, 118.60, 113.86, 113.54, 95.02, 54.20, 41.29; MS (LSIMS, m/z) 291 ($M^+$).

Example 17

5-(4'-Fluorobenzyl)quindolinium Hydrobromide and 5-(4'-Fluorobenzyl)quindolinium Hydrochloride A suspension of quindoline (0.7 g, 3.21 mmol) from Example 2, 4-fluorobenzyl bromide (2 mL, 16.0 mmol), and dry chloroform (4 mL) was heated in a bomb at 140° C. for 48 hours. The resulting solution was treated with diethyl ether, and the formed precipitate was filtered and washed thoroughly with diethyl ether to afford, after drying, 1.30 g (100%) of 5-(4'-fluorobenzyl) quindolinium hydrobromide. A portion of this material (0.83 g) was purified by LPLC on neutral alumina, eluting with 1–2% MeOH in $CHCl_3$. The product-containing fractions were combined, concentrated to a small volume and acidified with a solution of 1.0N HCl in diethyl ether to afford, following concentration and drying, 0.19 g (22.8%) of 5-(4'-fluorobenzyl) quindolinium hydrochloride as yellow crystals, mp 246.2°–246.5° C.; $^1H$ NMR (DMSO-$d_6$) δ 13.50 (s, 1H, NH), 9.50 (s, 1H), 8.67 (d, J=7.6, 1H), 8.52 (d, J=9.2, 1H), 8.32 (d, J=8.4, 1H), 8.12 (t, J=7.6, 1H), 7.95 (t J=7.6, 1H), 7.90 (d, J=3.6, 2H), 7.41 (m, 1H), 7.29 (dd, J=5.6, J=8.4, 2H), 7.19 (t, J=8.8, 2H), 6.82 (s, 2H, $NCH_2$); $^{13}C$ NMR (DMSO-$d_6$) δ 161.74 (d, J=244.1), 146.15, 138.07, 135.11, 134.14, 133.87, 132.99, 130.24, 129.45 (d, J=2.8), 128.34 (d, J=8.5) , 127.18, 126.50, 126.47, 125.14, 121.65, 117.50, 116.00 (d, J=22.1), 113.53, 112.78, 54.30; MS (EI, m/z) 326 ($M^+$-H).

Example 18

6-Nitroquindoline and 8-Nitroquindoline

To a suspension of quindolinium hydrochloride [(3.2 g, 1.25 mmol; obtained by acidification of quindoline (example 2) with HCl)], in glacial acetic acid (100 mL) was added dropwise at 0° C. HNO₃ (d 1.54, 50 mL). The reaction mixture was stirred at room temperature for 24 hours and poured into ice. The resulting precipitate was collected and washed with a saturated solution of NaHSO₄, water and dried to afford 2.4 g 72.5%) of an orange solid. TLC (silica gel, EtOAc-hexane, 1:1) showed two major spots with $R_f$ 0.56 and $R_f$ 0.30. Separation of 1 g of this mixture by LPLC, eluting with EtOAc-hexane (1:3), afforded 290 mg of 6-nitroquindoline (Rf 0.56) and 600 mg of 8-nitroquindoline. The structures of the two compounds were determined by COSY, HMQC, and HMBC 2D-NMR.

Data for 6-nitroquindoline: mp 273.9°–274.2° C.; $^1$H NMR (DMSO-d₆) δ 12.31 (s, 1H, NH), 8.78 (d, J=7.2, 1H), 8.49 (d, J=8.0, 1H), 8.47 (s, 1H), 8.21 (d, J=8.8, 1H), 8.18 (d, J=7.6, 1H), 7.73 (t, J=6.8, 1H), 7.62 (t, J=8.0, 1H), 7.45 (t, J=8.0, 1H); $^{13}$C NMR (DMSO-d₆) δ 144.40, 144.18, 136.83, 132.93, 131.95, 128.88, 128.74, 128.01, 127.27, 127.08, 125.82, 125.69 125.33, 119.15, 115.79; MS (EI, m/z) 263 (M⁺).

Data for 8-nitroquindoline: mp >300° C.; $^1$H NMR (DMSO-d₆) δ 12.22 (s, 1H, NH), 9.09 (d, J=2.4, 1H), 8.46 (dd, J=2.4, J=8.8, 1H), 8.44 (s, 1H), 8.22, (d, J=8.8, 1H), 8.15 (d, J=8.0, 1H), 7.73 (t, J=7.6, 1H), 7.70 (d, J=8.8, 1H), 7.62 (t, J=8.8, 1H); $^{13}$C NMR (DMSO-d₆) δ 147.10, 144.83, 144.08, 140.11, 133.36, 128.90, 127.84, 127.16, 127.10, 125.77, 124.92, 120.77, 117.50, 115.16, 111.84; MS (EI, m/z) 263 (M⁺).

Example 19

2-(Bromoacetamido)-5-fluorobenzoic Acid

A solution of 2-amino-5-fluorobenzoic acid (15 g, 96.6 mmol) in dry DMF (35 mL) and dioxane (35 mL) was cooled to 0° C. Bromoacetylbromide (8.43 mL, 96.6 mmol) was added dropwise at 0° C. over a 40 min period, and the reaction mixture was left overnight at room temperature. The reaction mixture was cooled to 0° C., and diluted slowly with water (300 mL). The precipitate which formed was collected washed with 5% HBr (50 mL) and water, and dried, to afford 25.43 g (95.1%) of the title compound as a white solid, mp 191.2°–191.8° C.; $^1$H NMR (acetone-d₆) δ 11.60 (s, 1H), 8.71 (dd, J=5.2, J=9.2, 1H), 7.80 (dd, J=3.2, J=9.6, 1H), 7.48-7.43 (m, 1H), 4.18 (s, 2H); $^{13}$C NMR (acetone-d₆) δ 168.80, 165.71, 158.37 (d, J=241.9), 138.56, 122.78 (d, J=7.8), 122.70, 122.06 (d, J=21.9), 117.98 (d, J=24.0), 30.45; MS (EI, m/z) 277 (M⁺).

Example 20

5-Fluoro-2-[(N-phenylamino)acetamido]benzoic acid

A solution of 2-(bromoacetamido)-5-fluorobenzoic acid from Example 19 (22.36 g, 91 mmol) and aniline (21 mL, 230 mmol) in dry DMF (150 mL) was heated at 85° C. for 5 hours. TLC showed indicated the presence of unreacted starting. Additional aniline (5 mL, 52 mmol) was added, and the solution was heated at 120° C. for 30 hours. After cooling, the reaction mixture was poured into ice-water (800 mL) and aqueous 5% KOH (100 mL) was added to adjust the pH to 10–11. The excess aniline was removed by extraction with $CH_2Cl_2$ (3×400 mL) and the aqueous layer was separated and acidified with aqueous 20% HBr. The resulting precipitate was collected, washed with water and dried, yielding 19.64 g (74.6%) of the title compound as white crystals, mp 194°–195° C.; $^1$H NMR (acetone-d₆) δ 11.87 (s, 1H), 8.88 (dd, J=5.2, J=9.6, 1H), 7.71 (dd, J=3.2, J=9.2, 1H), 7.45-7.39 (m, 1H), 7.14-7.10 (m, 2H), 6.68-6.64 (m, 3H), 3.92 (s, 2H); $^{13}$C NMR (acetone-d₆) δ 171.30, 168.14, 163.22, 157.97 (d, J=241.3), 148.97, 138.66, 129.82, 122.60 (d, J=7.1), 121.90 (d, J=21.9), 118.63, 117.78 (d, J=24.0), 113.67, 50.07; MS (EI, m/z) 288.1 (M⁺).

Example 21

2-Fluoro-11-quindolone

A mixture of 5-fluoro-2-[(N-phenylamino)acetamido] benzoic acid from Example 20 (4.5 g, 15.8 mmol) and polyphosphoric acid (PPA, 150 g) was heated with mechanical stirring at 130° C. for 2 hours. The reaction mixture was poured into ice-water (1.2 L), neutralized with saturated KOH solution and extracted with EtOAc (2×750 mL). The ethyl acetate layer was washed with water and brine, dried and concentrated to afford 2.25 g (56.3%) of the title compound as a yellow solid, mp >270° C. A portion of this material was purified by LPLC, eluting with EtOAc-MeOH (5:1); $^1$H NMR (DMSO-d₆) δ 12.65 (s, NH), 11.75 (s, NH), 8.18 (d, J=8.0, 1H), 7.99 (dd, J=2.4, J=9.6, 1H), 7.79 (dd, J=4.4, J=8.8, 1H), 7.60 (t, J=8.0, 1H), 7.53-7.45 (m, 2H), 7.21 (t, J=7.6, 1H); $^{13}$C NMR (DMSO-d₆) δ 166.37, 156.77 (d, J=251.3), 138.85, 135.75, 129.34, 127.71, 123.45 (d, J=6.0), 122.67, 120.91, 120.26 (d, J=7.7), 119.65 (d, J=26.5), 118.99, 115.74, 112.66, 108.75 (d, J=23.1); MS (EI, m/z), 252 (M⁺-H).

Example 22

2-Fluoro-11-chloroquindoline

A solution of 2-fluoro-11-quindolone from Example 21 (6.0 g, 23.8 mmol) in POCl₃ (60 mL) was refluxed for 2 hours, allowed to cool, poured into ice, neutralized with saturated KOH solution, and extracted with EtOAc (3×500 mL). The extract was washed with water and brine, dried, concentrated and purified by LPLC, eluting with EtOAc-hexane (1:6) to afford 3.5 g (54.5%) of the title compound as a yellow solid, mp 208.5°–210.0° C.; $^1$H NMR (DMSO-d₆) δ 11.89 (s, NH), 8.32 (s, J=8.0, 1H), 8.29 (d, J=5.2, 1H), 7.90 (dd, J=2.8, J=10.4, 1H), 7.69-7.60 (m, 3H), 7.33 (t, J=8.0, 1H); $^{13}$C NMR (DMSO-d₆) δ 170.3, 159.98 (d, J=258.1), 145.83, 144.00, 140.83, 132.25 (d, J=10.5), 130.46, 130.41, 124.43 (d, J=11.2), 121.62, 121.10, 120.39, 116.92 (d, J =27.6), 112.06, 105.52 (d, J=26.2); MS (EI, m/z) 270 (M⁺).

Example 23

2-Fluoro-5-methyl-11-chloroquindolinium Hydrotrifluoromethanesulfonate

To a suspension of 2-fluoro-11-chloroquindoline from Example 22 (1.56 g, 5.76 mmol) in anhydrous toluene (50 mL) was added methyl triflate (1.89 g, 1.30 mL, 11.52 mmol) at room temperature and the reaction mixture was stirred for 1 day. The reaction mixture was diluted with diethyl ether (100 mL) and the solid was filtered and washed with ether. After drying, 2.40 g (96%) of the 2-fluoro-5-methyl-11-chloroquindolinium hydrotrifluoromethanesulfonate product was obtained as an orange solid, mp 297.5°–299.5° C.; $^1$H NMR (DMSO-d₆) δ 13.29 (s, 1H), 8.97 (dd, J=10.0, J=4.4, 1H), 8.82 (d, J=8.4, 1H), 8.41 (dd, J=9.6, J=3.2, 1H), 8.26-8.18 (m, 1H), 7.99 (dt, J=8.4, J=0.8, 1H), 7.84 (d, J=8.4, 1H), 7.57 (dt, J=8.4, J=0.8, 1H), 5.04 (s, 3H); 13C NMR (DMSO-d₆) δ 160.50 (d, J=250.5), 145.92, 138.99, 134.85, 132.88, 132.54, 127.60 (d, J=5.0), 126.74, 124.96 (d, J=9.9), 122.48 (d, J=10.0), 122.39 (d, J=26.9), 122.26, 114.47, 113.49, 108.46 (d, J=25.4), 40.99; MS (EI, m/z) 285 (M⁺), 287 (M+2⁺).

Example 24

2-Fluoro-5-methyl-11-chloroquindoline

To a suspension of the triflate salt obtained in Example 23 (2.34 g, 5.38 mmol) in chloroform (500 mL) was added aqueous 5% KOH. The chloroform layer was separated and the aqueous layer was extracted with chloroform (5×350 mL). The ensuing emulsion was separated from the aqueous layer. Anhydrous $Na_2CO_3$ was added to the emulsion until it obtained a paste-like consistency. The aqueous layer was repeatedly extracted with chloroform until the aqueous layer was no longer purple. The $Na_2CO_3$ paste was ground with a mortar and pestle and exhaustively extracted with chloroform. All chloroform extracts were combined, dried over anhydrous $Na_2CO_3$, filtered and concentrated. The resulting solid was resuspended in chloroform (800 mL), solid anhydrous $Na_2CO_3$ was added to the suspension (100 g), and the mixture was sonicated and then concentrated. The resulting solid was poured onto a basic alumina column, eluted sequentially with chloroform (1000 mL), EtOAc-chloroform (1:9, 1000 mL), EtOAc-chloroform (1.5:8.5, 1000 mL), EtOAc-chloroform (2.5:7.5, 1000 mL), and EtOAc-chloroform (3.5:6.5, 1000 mL) to remove the impurities. Elution with 4% methanol in chloroform afforded 1.48 g (96.7%) of the title compound as a purple solid.

Example 25

2-Fluoro5-methyl-11-chloroquindolinium Hydrochloride

A solution of 2-fluoro-5-methylquindoline from Example 24 (100 mg) in chloroform (50 mL) was treated at room temperature with a 1M solution of HCl in ether until a yellow solution/precipitate formed. Methanol was added to homogenize the mixture and then the solution was concentrated. The resulting solid was recrystallized from hot $CHCl_3$ (50 mL)/EtOH (5 mL), with a minimum amount of ether being added to facilitate the crystallization process. Filtration, followed by washing the product with diethyl ether and drying afforded 101 mg (90.2%) of the title compound as yellow crystals, mp 211.8°–212.5° C.; ¹H NMR (DMSO-d₆) δ 13.55 (s, 1H), 8.99 (dd, J=10.0, J=4.4, 1H), 8.82 (d, J=8.4, 1H), 8.40 (dd, J=9.2, J=2.8, 1H), 8.25-8.18 (m, 1H), 7.99 (dt, J=8.4, J=0.8, 1H), 7.88 (d, J=8.0, 1H), 7.56 (dt, J=8.4, J=0.8, 1H), 5.04 (s, 3H); 13C NMR (DMSO-d₆) 160.48 (d, J=250.5), 146.01, 138.95, 134.75, 132.85, 132.53, 127.58 (d, J=5.6), 126.71, 124.94 (d, J=10.6), 122.51 (d, J=9.3), 122.33 (d, J=27.5), 122.20, 114.42, 113.56, 108.44 (d, J=25.4), 40.02; MS (EI, m/z) 285 (M⁺), 287 (M+2⁺).

Example 26

2-Fluoro -5-methyl-11-(phenoxy)quindolinium Hydrochloride

A solution of 2-fluoro-5-methyl-11-chloroquindoline from Example 24 (510 mg, 1.79 mmol) and phenol (1.5 g, 15.96 mmol) in $EtOCH_2CH_2OH$ (50 mL) was heated at 100° C. for 10 min. During this time the color of the reaction mixture changed from purple to yellow, and a yellow precipitate formed. After cooling, the reaction mixture was diluted with diethyl ether (150 mL) and the precipitate was collected, washed thoroughly with diethyl ether and dried, providing 410 mg (60.5%) of the title compound, mp 249.5°–249.8° C.; ¹H NMR (DMSO-d₆) δ 12.94 (s, 1H), 8.98 (dd, J=4.4, J=10.00, 1H), 8.84 (d, J=8.4, 1H), 8.19-8.13 (m, 1H), 8.01 (dd, J=2.8, J=8.8, 1H), 7.94 (t, J=8.4, 1H), 7.77 (d, J=8.4, 1H), 7.55 (t, J=8.4, 1H), 7.44-7.40 (m, 2H), 7.22 (t, J=8.4, 1H), 7.15-7.12 (m, 2H), 5.06 (s, 3H); ¹³C NMR (DMSO-d₆) δ 160.90, 157.69 (d, J=152.9), 145.58, 144.49 (d, J=5.2), 141.74, 134.57, 134.30, 130.29, 127.14, 126.18, 124.21, 122.41 (d, J=8.2), 122.23 (d, J=9.6), 122.02 (d, J=10.4), 121.85, 116.10, 114.57, 113.51, 106.46 (d, J=26.2), 40.60; MS (EI, m/z) 341 (M⁺-H) .

Example 27

2-Fluoro-5-methyl-11-(phenylamino)quindolinium Hydrochloride

A solution of 2-fluoro-5-methyl-11-chloroquindoline from Example 24 (530 mg, 1.79 mmol) and aniline (0.75 g, 8.06 mmol) in $EtOCH_2CH_2OH$ (50 mL) was heated at 120° C. for 10 min. During this time the color of the reaction mixture changed from purple to yellow, and a yellow precipitate formed. After cooling, the reaction mixtureced was diluted with diethyl ether (100 mL) and the precipitate was collected, washed thoroughly with diethyl ether and dried, providing 555 mg (79.4%) of the title compound, mp 280° C. (sublimed); ¹H NMR (DMSO-d₆) δ 11.26 (s, NH), 10.62 (s, NH), 8.64 (d, J=8.0, 2H), 8.46 (d, J=9.2, 1H), 8.04 (t, J=8.0, 1H), 7.77-7.68 (m, 2H), 7.47-7.39 (m, 3H), 7.29-7.22 (m, 3H), 4.81 (s, 3H); ¹³C NMR (acetone-d₆) δ 152.50 (d, J=259.5), 136.01, 132.03 (d, J=2.96), 130.95, 130.52, 127.76, 125.68, 123.12, 119.52, 117.72, 115.57, 115.32, 115.08, 113.86 (d, J=9.6), 113.37, 112.07 (d, J=9.7), 107.81, 106.57, 101.60 (d, J=26.2), 32.13; MS (EI, m/z) 340 (M⁺).

Example 28

2-Fluoro-5-methyl-11-phenylquindolinium Hydrochloride

A suspension of 2-fluoro-5-methyl-11-chloroquindoline from Example 24 (300 mg, 0.35 mmol) in dry dioxane (30 mL) was added to a 1.0M solution of $C_6H_5MgBr$ in ether (6 mL, 6.0 mmol, obtained from Aldrich Chemical Co.) at room temperature. The reaction mixture was stirred for 1 hour at room temperature, then heated for 1 hour at 50° C. The reaction mixture was cooled, poured into ice-water (300 mL), allowed to stand overnight to effect hydrolysis (pH ~7), and then extracted with EtOAc (4×50 mL) and chloroform (4×50 mL). The combined chloroform and ethyl acetate extracts were washed with water, dried, concentrated, and then purified by chromatography on a basic alumina column, eluting 0.5–1.5% MeOH in $CHCl_3$. The product containing fractions were combined, acidified with 1.0M HCl solution in ether and concentrated to afford 175 mg (45.8%) of the title compound as a yellow solid, mp 251.4°–251.8° C.; ¹H NMR (DMSO-d₆) δ 12.44 (s, NH), 9.00 (dd, J=4.4, J=9.2, 1H), 8.85 (d, J=8.4, 1M), 8.17 (t, J=7.6, 1H), 7.93 (t, J=7.8, 1H), 7.81-7.79 (m, 4H), 7.74-7.70 (m, 2H), 7.62 (d, J=9.2, 1H), 7.54 (t, J=7.2, 1H), 5.12 (s, 3H); ¹³C NMR (DMSO-d₆) δ 159.66 (J=249.1), 146.35, 138.27, 136.45, 134.13, 132.80 (J=4.2), 131.15, 130.34, 129.94, 129.60, 129.39, 126.20 (J=9.9), 121.88 (J=9.1), 121.72, 121.66, 121.46, 114.01, 113.49, 109.94 (J=24.1), 49.94; (LSIMS, m/z) 327 (MH⁺).

Example 29

2-Fluoro-5-methyl-11-](4-chlorophenyl)thio] quindolinium Hydrochloride

To a solution of 2-fluoro-5-methyl-11-chloroquindoline from Example 24 (56 mg, 0.209 mmol) in 2-ethoxyethanol (5 mL) was added 4-chlorothiophenol (36 mg, 120 mol %). The reaction mixture was refluxed for 10 min, during which time the reaction mixture became orange and an orange precipitate formed. The reaction mixture was cooled to room temperature, filtered, and the solid was washed with ether and dried, affording 60 mg (73%) of the title compound, mp 254°–256° C.; $^1$H NMR (DMSO-$d_6$) δ 13.18 (s, 1H, NH), 9.00 (dd, 1H, J=4.4, J=5.2), 8.85 (d, 1H, J=8.4), 8.36 (d, 1H, J=8.0), 8.15 (t, 1H, J=7.2), 7.98 (d, 1H, J=8.0), 7.57 (t, 1H, J=7.2), 7.38-7.33 (m, 4H), 5.10 (s, 3H); $^{13}$C NMR (DMSO-$d_6$) δ 161.64, 159.15, 146.27, 138.88, 138.15, 134.90, 132.65, 132.35, 132.07, 130.45, 129.66, 128.60, 126.98, 122.77, 122.67, 121.67, 121.41, 114.55, 113.64, 109.83, 109.58, 41.29; MS (FAB, m/z) 393 (M$^+$).

Example 30

Phenylglycine-o-carboxylic Acid

To a solution of KOH (25 g, 440 mmol) and $K_2CO_3$ (25 g, 180 mmol) in $H_2O$ (400 mL) was added 2-bromobenzoic acid, (38.2 g, 190 mmol), followed by glycine (25 g, 330 mmol) and CuBr (540 mg, 3.76 mmol). This mixture was heated at reflux for 4 h. After cooling to room temperature, the mixture was filtered over a fritted funnel to remove traces of Cu and the filtrate was acidified to pH 3 with concentrated HCl. The precipitate was collected and dried to obtain 32.44 g (88%) of the title compound, mp 225.9°–226.2° C. (decomp., white foam); 1H NMR (DMSO-$d_6$) δ 12.4 (br, 1H), 8.06 (br, 1H), 7.80 (m, 1H), 7.35 (m, 1H), 6.60 (m, 2H), 3.99 (s, 2H); $^{13}$C NMR (DMSO-$d_6$) δ 171.8, 169.7, 150.0, 134.4, 131.7, 114.7, 111.5, 110.6, 44.4; MS (EI, m/z) 195 (M$^+$).

Example 31

1-Acetyl-3-acetoxyindole

To a mixture of phenylglycine-o-carboxylic acid obtained in Example 30 (2.30 g, 11.8 mmol) and NaOAc (3.75 g, 47.1 mmol) in DMF (29 mL) was slowly added $Ac_2O$ (11.7 mL, 118 mmol) and the mixture was refluxed for 2 hours. After cooling, the mixture was concentrated to 10 mL, partitioned between $H_2O$ (60 mL) and $CHCl_3$ (120 mL), and the aqueous layer was extracted with $CHCl_3$ (3x). The combined organics were washed with $Na_2CO_3$ (1M), $H_2O$, brine and dried (MgSO$_4$). Purification of the crude oil by LPLC, eluting with hexane-EtOAc (2:1), afforded 1.89 g (74%) of the title compound as a light yellow powder, $R_f$ 0.34 (hexane-EtOAc 2:1), mp 79.6°–80.5° C.; $^1$H NMR (CDCl$_3$) δ 8.47 (d, J=8.0, 1H), 7.72 (s, 1H), 7.55 (d, J=8.0, 1H), 7.40 (t, J=8.0, 1H), 7.31 (t, J=8.0, 1H), 2.62 (s, 3H), 2.40 (s, 3H), $^{13}$C NMR (CDCl$_3$) δ 168.7, 167.8, 134.6, 132.8, 126.2, 123.7, 123.6, 117.4, 116.7, 113.3, 23.9, 21.0; MS (EI, m/z) 217 (M$^+$).

Example 32

1-Acetylindoxyl

With some modification, the procedure of Galen was used to obtain the title compound [Galun, A.; Kampf, A.; Markus, A. *J. Heterocyclic Chem.*, 1979, 16, 221]. To a refluxing solution of 1-acetyl-3-acetoxyindole obtained in Example 31 (1.88 g, 8.66 mmol) in EtOH (46 mL) was added a hot solution (ca 90° C.) of $Na_2SO_3$ (1.244 g, 9.87 mmol) in $H_2O$ (46 mL). The mixture was refluxed for 10 min., then cooled to room temperature. The EtOH was removed in vacuo and the aqueous layer extracted with $CHCl_3$ (3x). The combined organic extracts were washed with $H_2O$, brine, dried (MgSO$_4$) and concentrated to afford 1.46 g (96%) of the title compound as a slightly greenish powder, $R_f$ 0.11 (hexane-EtOAc 2:1), mp 137.6°–138.1° C. (decomp); $^1$H NMR (CDCl$_3$) δ 8.57 (d, J=8.8, 1H), 7.76 (d, J=7.6, 1H), 7.68 (t, J=7.6, 1H), 7.24 (m, 1H), 4.31 (s, 2H), 2.33 (s, 3H); $^{13}$C NMR (CDCl$_3$) δ 194.7, 168.1, 153.8, 137.4, 124.8, 124.2, 123.7, 118.6, 56.1, 24.3; MS (EI, m/z) 175 (M$^+$).

Example 33

1-Acetyl-2-(2-nitrophenylmethylene)-3-oxo-2,3-dihydroindole

A solution of 1-acetylindoxyl obtained in Example 32 (1.92 g, 10.96 mmol), 2-nitrobenzaldehyde (2.03 g, 13.16 mmol) and piperidine (5 drops) in benzene (100 mL) was refluxed in a Dean-Stark apparatus for 5 hours, turning the solution red. After cooling, the solvent was evaporated and the residue triturated was with ether. The precipitate was filtered and purified by LPLC, eluting with $CH_2Cl_2$, to afford 1.34 g (40%) of the title compound as yellow crystals, $R_f$ 0.38 ($CH_2Cl_2$), mp 199.0°–199.6° C. (decomp) [lit 200° C. (Buzas, A.; Merour, J. Y. *Synthesis* 1989, 458)]; $^1$H NMR (CDCl$_3$) δ 8.24 (d, J=7.2, 1H), 8.09 (s, 1H), 8.04 (d, J=8.4, 1H), 7.65–7.71 (m, 3H), 7.59 (d, J=8.8, 2H), 7.26 (d, J=7.2, 1H), 2.75 (s, 3H); $^{13}$C NMR (CDCl$_3$; one quaternary carbon missing or obscured) δ 183.6; 169.1, 148.6, 136.5, 133.9, 133.1, 132.2, 130.0, 129.3, 124.8, 124.7, 124.5, 124.4, 124.0, 117.2, 26.9; MS (EI, m/z) 266 (M-COCH$_3$+).

Example 34

10-Acetylquindoline

A suspension of 1-acetyl-2-(2-nitrophenyl methylene)-3-oxo-2,3-dihydroindole from Example 33 (220 mg, 0.71 mmol), 10% Pd/C (33 mg) and absolute EtOH (25 mL) was shaken on a Parr Shaker at 50 psi of $H_2$ for 3 hours. The Pd catalyst was filtered off over a celite pad and the solvent was evaporated. The crude yellow product (209 mg, >100%) was purified by LPLC, eluting with hexane-EtOAc (2:1), to afford 92 mg (50%) of the title compound as a light yellow solid (90% pure by NMR), $R_f$ 0.38 (hexane-EtOAc 1:1), mp 163.2°–164.6° C. [(lit 177°–178° C. (Fichter, F.; Boehringer, R. *Chem. Ber.* 1906, 39, 3932)]; $^1$H NMR (CDCl$_3$) δ 9.04 (s, 1H), 8.52 (d, J=8.0, 1H), 8.28 (d, J=8.8, 1H), 8.16 (d, J=8.4, 1H), 8.02 (d, J=8.4, 1H), 7.77 (m, 1H), 7.68 (m, 1H), 7.61 (m, 1H), 7.52 (m, 1H), 2.99 (s, 3H); $^{13}$C NMR (CDCl$_3$) 169.7, 147.3, 145.9, 141.5, 137.5, 131.4, 130.6, 128.8, 128.6, 128.5, 127.3, 126.1, 124.4, 122.0, 121.6, 115.8, 27.6; MS (EI, m/z) 260 (M$^+$).

Example 35

1-Acetyl-2-(3-methoxy-2-nitrophenylmethylene)-3-oxo-2,3-dihydroindole

A solution of 2-acetylindoxyl from Example 32 (1.58 g, 9.0 mmol), 2-nitro-3-methoxybenzaldehyde (2.02 g, 10.8 mmol) and piperidine (5 drops) in benzene (150 mL) was refluxed in a Dean-Stark apparatus for 5 hours, turning the solution red. During the first three hours, the solvent from the Dean-Stark apparatus was removed 4 times and replaced with freshly distilled benzene. After cooling, the solvent was removed and concentrated to afford a residue. The residue was purified by LPLC, eluting with $CH_2Cl_2$, to afford 1.82 g (60%) of the title compound as shiny, yellow crystals. The product is an 85/5 E/Z mixture as determined by NMR, $R_f$ 0.19 (CH$_2$Cl$_2$), mp 161.3°–161.9° C.; $^1$H NMR (CDCl$_3$) (major stereoisomer) δ 8.00 (d, J=8.4, 1H), 7.72 (m, 1H), 7.65 (m, 2H), 7.47 (t, J=8.0, 1H), 7.26 (d, J=7.6, 1H), 7.19 (d, J=8.0, 1H), 7.09 (d, J=9.2, 1H), 3.94 (s, 3H), 2.65 (s, 3H); $^{13}$C NMR (CDCl$_3$; one quaternary carbon missing or obscured) (major stereoisomer) 183.0, 169.0, 151.2, 148.6, 136.6, 131.7, 130.9, 128.2, 124.8, 124.6, 122.1, 119.9, 117.1, 112.8, 56.5, 26.8; MS (EI, m/z) 296 (M-COCH$_3$+).

Example 36

6-Methoxy-10-acetylquindoline

A suspension of 1-acetyl-2-(3-methoxy-2-nitrophenylmethylene)-3-oxo-2,3-dihydroindole from Example 35 (460 mg, 1.36 mmol), 10% Pd/C (70 mg) and MeOH (17 mL) was stirred under H$_2$ at atmospheric pressure (balloon) for 3 hours. Additional Pd/C (70 mg) was added, a fresh balloon of H$_2$ was attached and the mixture was stirred at room temperature overnight. The Pd/C catalyst was filtered over celite and the filtrate was evaporated. The resulting crude yellow product (209 mg, >100%) was purified by LPLC, eluting with CH$_2$Cl$_2$, then CH$_2$Cl$_2$/EtOAc (3:97), to obtain 208 mg (53%) of the title compound as a colorless solid, R$_f$ 0.47 (hexane-EtOAc 1:1), mp 125.1°–125.8° C.; $^1$H NMR (CDCl$_3$) δ 9.02 (s, 1H), 8.62 (dd, J=7.6; J=0.8 1H), 8.13 (d, J=8.4, 1H), 7.65 (dt, J=8.0; J=0.8, 1H), 7.59 (d, J=8.4, 1H), 7.53 (m, 2H), 7.11 (d, J=7.6, 1H), 4.18 (s, 3H), 2.97 (s, 3H); $^{13}$C NMR (CDCl$_3$) δ 169.8, 155.2, 146.5, 141.4, 138.1, 131.9, 130.5, 128.6, 126.3, 124.3, 124.2, 122.7, 121.6, 120.5, 115.6, 106.7, 56.2, 27.7; MS (EI, m/z) 290 (M$^+$).

Example 37

6-Methoxy-5-methyl-10-acetylquindolinium Iodide

6-Methoxy-10-acetylquindoline from Example 36 (194 mg, 0.668 mmol) was suspended in CH$_3$I (1.25 mL, 200 mmol) and heated in a pressure vessel at 150° C. with stirring for 24 h. After cooling, the resulting precipitate was filtered and dried to obtain 77 mg (27%) of the title compound as brown crystals, mp >250° C. (sublimes); $^1$H NMR (DMSO-d$_6$) 9.84 (s, 1H), 8.83 (d, J=8.0, 1H), 8.56 (d, J=8.8, 1H), 8.22 (m, 1H), 8.09 (m, 1H), 7.94 (t, J=8.0, 1H), 7.79 (m, 2H), 5.07 (s, 3H), 4.17 (s, 3H), 3.06 (s, 3H); $^{13}$C NMR (DMSO-d$_6$) δ 170.5, 150.8, 143.7, 143.1, 135.5, 132.5, 130.1, 129.3, 129.12, 129.09, 127.5, 125.1, 122.3, 117.5, 116.8, 115.2, 57.3, 47.7, 27.7; MS (LSIMS, m/z) 305 (M$^+$).

Example 38

6-Methoxy-5-methylquindoline

A solution of 6-methoxy-5-methyl-10-acetylquindolinium iodide obtained in Example 37 dissolved in approximately 50 mL of ethanol-free chloroform was adsorbed onto anhydrous Na$_2$CO$_3$ (1 g/100 mg iodide salt) and applied to a column filled with basic alumina. The mixture was eluted with CHCl$_3$ until the UV active impurities eluted. Elution with CHCl$_3$-MeOH (97:3) provided the title compound as a purple solid; $^1$H NMR (CDCl$_3$) δ 8.74 (s, 1H), 8.22 (d, J=8.4, 1H), 7.85 (d, J=8.4, 1H), 7.73 (d, J=8.4, 1H), 7.57 (m, 1H), 7.48 (m, 1H), 7.18 (d, J=7.6, 1H), 7.08 (m, 1H), 5.07 (s, 3H), 4.12 (s, 3H); $^{13}$C NMR (CDCl$_3$) δ 159.8, 150.5 (2 carbons), 144.1, 141.5, 131.2, 127.2, 126.3, 124.4, 124.1, 122.2, 119.5, 117.6, 114.1, 109.4, 56.5, 45.3; MS (LSIMS, m/z) 263 (M$^+$).

Example 39

3-Chloro-2-(bromoacetamido)benzoic Acid

A solution of 2-amino-3-chlorobenzoic acid (7 g, 0.041 mol), anhydrous DMF (20 mL) and anhydrous dioxane (20 mL) was cooled to 0° C. in a 250 mL 3-necked flask, fitted with a magnetic stirrer and constant additional funnel. Bromoacetyl bromide was added dropwise over a 27 min period, keeping the internal temperature between 0° to 2° C. After the addition was complete, the solution was allowed to warm to room temperature and stirring was continued for 4 hours. The reaction mixture was cooled in an ice-bath and diluted with water (100 mL). The resulting yellow precipitate was filtered, washed with water and dried in vacuum oven for 2 days, affording 7.7 g (65%) of the title compound as a light yellow crystals, mp 173°–175° C.; $^1$H NMR (CD$_3$OD) 7.88 (dd, 1H, J=1.6, J=6), 7.68 (dd, 1H, J=1.2, J=6.8), 7.39 (t, 1H, J=8); $^{13}$C NMR (CD$_3$OD) δ 176.37, 168.38, 134.84, 134.40, 131.95, 130.53, 129.15, 129.05, 28.66; MS (EI, m/z) 293 (M$^+$).

Example 40

4-Chloro-2-(bromoacetamido)benzoic Acid

A solution of 2-amino-4-chlorobenzoic acid (10 g, 0.06 mmol), anhydrous DMF (30 mL) and anhydrous dioxane was cooled to 0° C. in 300 mL 3-necked flask fitted with magnetic stirrer and constant additional funnel. Bromoacetyl bromide was added dropwise over a 2 h period, keeping the internal temperature between 0°–2° C. After the addition was completed, the solution was allowed to warm to room temperature and the reaction mixture was stirred 20 h. The reaction mixture was cooled in an ice-bath and slowly diluted with water (300 mL). The resulting white crystalline product was filtered. Recrystallization from EtOAc/Hex afforded 9.2 g (54%) of the title compound, mp 156.4°–158° C.; $^1$H NMR (DMSO-d$_6$) δ 13.99 (s, 1H, NH), 11.72 (s, 1H, COOH), 8.54 (d, 1H, J=2.0), 8.00 (d, 1H, J=8.8), 7.27 (dd, 1H, J=2.4, J=6.4), 4.28 (s, 2H); $^{13}$C NMR (DMSO-d$_6$) δ 168.60, 165.54, 141.12, 138.51, 133.88, 123.36, 119.23, 115.58, 30.54; MS (EI, m/z) 293 (M$^+$).

Example 41

5-Chloro-2-(bromoacetamido)benzoic Acid

A solution of 2-amino-5-chlorobenzoic acid (10 g, 0.06 mol), anhydrous DMF (30 mL) and dioxane (30 mL) was cooled to 0° C. in a 250 mL 3- necked flask, fitted with a magnetic stirrer, thermometer and additional funnel. Bromoacetyl bromide (11.8 g, 5 mL, 100 mol %) was added dropwise over a 20 min period, keeping the internal temperature between 0° C. to 1° C. After the addition was completed, the solution was allowed to warm to room temperature and stirring was continued overnight at rt. The reaction mixture was cooled in an ice-bath, stirred for 30 min and diluted with water (80 mL). The resulting light yellow precipitate was filtered, washed with water, and dried in vacuum oven (20 h, 40°–45° C.), to afford 11.4 g (67%) of the title compound, mp 210°–212° C. (decomp.); $^1$H NMR (CD$_3$OD) δ 8.58 (d, 1H, J=9.2), 8.03 (d, 1H, J=2.8), 7.55 (dd, 1H, J=2.4, J=6.4), 4.11 (s, 2H); $^{13}$C NMR (CD$_3$OD) δ 196.94, 169.69, 140.49, 134.86, 131.94, 129.49, 122.87, 119.47, 30.04; MS (EI, m/z) 293 (M$^+$).

Example 42

6-Chloro-2-(bromoacetamido)benzoic Acid

A solution of 2-amino-6-chlorobenzoic acid (10 g, 0.06 mol), anhydrous DMF (30 mL) and anhydrous dioxane (30 mL) was cooled to 0° C. in 300 mL 3-necked flask fitted with a magnetic stirrer and constant additional funnel. Bromoacetyl bromide was added dropwise over a 20–25 min period keeping the internal temperature between 0° to 1° C. After the addition was completed, the solution was allowed to warm to room temperature and stirring was continued for 20 h. The reaction mixture was cooled in an ice-bath and diluted with water (150 mL). The resulting yellow crystalline product was filtered, washed sequentially with 5% HBr solution (50 mL), water (50 mL), and then dried in vacuum oven (20 h, 40°–45° C.) to afford 5 g (30%) of the title compound, mp 133°–135° C. (decomp.); $^1$H NMR (CD$_3$OD) 7.70 (d, 1H, J=8), 7.43 (t, 1H, J=8.4), 7.35 (d, 1H, J=8), 4.05 (s, 2H); $^{13}$C NMR (CD$_3$OD) δ 168.19, 167.84, 137.24, 133.31, 132.85, 132.08, 128.78, 128.21, 124.20, 29.21; MS (EI, m/z) 293 (M$^+$).

Example 43

3-Chloro-2-[(N-phenylamino)acetamido]benzoic Acid

A solution of 3-chloro-2-(bromoacetamido)benzoic acid from Example 39 (7.5 g, 0.026 mol), aniline (5.8 mL, 250 mol %) and anhydrous DMF (60 mL) was heated at 95°–100° C. for 20h, cooled and stirred at rt for 4h. The reaction mixture was poured into ice-water (400 mL) and the precipitated product was solubilized by adding aqueous 5% KOH (60 mL). The resulting milky homogenous solution was extracted with CH$_2$Cl$_2$ (3×70 mL). The combined CH$_2$Cl$_2$ extracts were set aside and the aqueous layer was acidified to pH=3 with aqueous 5% HBr. The resulting oil was extracted into EtOAc (3×100 mL) and the combined extract was washed with brine, dried, filtered and concentrated. Recrystallization of the resulting solid from diethyl ether afforded 3 g (38%) of the title compound as a white crystals, mp 184°–185° C.; $^1$H NMR (CD$_3$OD) δ 7.85 (dd, 1H, J=1.6, J=6), 7.66 (dd, 1H, J=1.6, J=6.4), 7.33 (t, 1H, J=8), 7.16 (t, 2H, J=7.2), 6.72 (dd, 3H, J=2, J=5.6), 3.91 (s, 2H); $^{13}$C NMR (CD$_3$OD): 203.86, 196.95, 173.19, 173.17, 168.69, 149.44, 134.30, 130.41, 130.09, 128.42, 119.31, 114.44; MS (EI, m/z) 304 (M$^+$).

Example 44

4-Chloro-2-[(N-phenylamino)acetamido]benzoic Acid

A solution of 4-chloro-2-(bromoacetamido)benzoic acid from Example 40 (6.5 g, 0.02 mol), aniline (5.2 mL, 250 mol %) and anhydrous DMF (50 mL) was heated to 100°–105° C. for 4h, and stirred at rt for 20h. The reaction mixture was poured into ice-water (400 mL) and the precipitated product was solubilized by adding aqueous 5% KOH (60 mL). The resulting milky homogenous solution was extracted with CH$_2$Cl$_2$ (3×100 mL). The combined CH$_2$Cl$_2$ extracts were set aside and the aqueous layer was acidified with aqueous 5% HBr to pH=3. The resulting oil was extracted into EtOAc (3×100 mL) and the combined extract was washed with brine, dried, filtered and concentrated. Trituration of the resulting solid with diethyl ether afforded 4.5 g (66%) of the crude title compound as light-beige crystals, mp 177.8°–180° C. The crude compound (4.5 g) was stirred with EtOAc (~100 mL) and the resulting insoluble portion was filtered off. The filtrate was concentrated to a light-beige solid which was refluxed with benzene (80 mL) for 40 min. The bnenzene mixture was filtered while hot and the filtered solid was dried for 4 h under high vacuum, yielding 2.75 g (40%) of the title compound as light crystals, mp 229°–230° C. (became "wet" at 227° C.); $^1$H NMR (DMSO-d$_6$) δ 13.6 (bs, 1H), 12.11 (s, 1H), 8.82 (d, J=1.6, 1H), 7.93 (d, J=8.8, 1H), 7.20 (dd, J=6.0, J=2.6, 1H), 7.10 (t, J=7.6, 2H) 6.63-6.58 (m, 4H), 3.85 (s, 2H); $^{13}$C NMR (DMSO-d$_6$)δ 171.48, 168.31, 148.01, 141.53, 138.58, 132.86, 128.97, 128.30, 122.61, 118.72, 118.67, 117.16, 114.68, 112.45, 48.89.

Example 45

5-Chloro-2-[(N-phenylamino)acetamido]benzoic Acid

A solution of 5-chloro-2-(bromoacetamido)benzoic acid from Example 41 (10 g, 0.03 mol), aniline (8 g, 7.8 mL, 250 mol %) and DMF (60 mL) was heated at 100°–110° C. for 4 h. The reaction mixture was poured into ice-water (200 mL) and the resulting solid product was solubilized by adding 5% KOH (40 mL). The mixture was extracted with CH$_2$Cl$_2$ (3×100 mL) and the aqueous layer was acidified with 5% HBr to pH=3 and extracted with EtOAc (3×200 mL). The EtOAc washings were dried (Na$_2$SO$_4$), filtered and concentrated to afford, after drying under vacuum, 7.8 g (75%) of the title compound as a white solid, mp 210°–212° C.; $^1$H NMR (DMSO-d$_6$) δ 13.99 (s, 1H, NH), 11.96 (s, 1H, COOH), 8.75 (d, 1H, J=8), 7.87 (d, 1H, J=2.8), 7.68 (d, 1H, J=2.4), 7.65 (d, 1H, J=2.8), 7.10 (t, 2H, J=7.6), 6.61 (m, 4H), 3.84 (s, 2H); $^{13}$C NMR (DMSO-d$_6$) δ 171.08, 167.81, 148.05, 139.36, 133.81, 130.25, 128.97, 126.20, 121.25, 117.77, 117.14, 112.45, 48.90; MS (EI, m/z) 304 (M$^+$).

Example 46

6-Chloro-2-[(N-phenylamino)acetamido]benzoic Acid

A solution of 6-chloro-2-(bromoacetamido)benzoic acid from Example 42 (7 g, 0.024 mol), aniline (5.6 g, 6 mL, 250 mol %) and DMF (40 mL) was heated at 100° C. for 5 h. The reaction mixture was cooled to rt, poured onto ice and the resulting crystalline product was solubilized by adding 5% KOH (70 mL, pH=9). The resulting milky homogenous solution was extracted with CH$_2$Cl$_2$ (3×100 mL), and the aqueous layer was acidified to pH=3 with 5% HBr and extracted with EtOAc (4×100 mL). Combined EtOAc washings were dried and concentrated. Recrystallization of the resulting solid from EtOAc/Hex. afforded 6 g (82%) of the title compound as white crystals, 176°–178.2° C.; $^1$H NMR (DMSO-d$_6$) δ 9.93 (s, 1H , COOH), 7.97 (d, 1H, J=8), 7.42 (t, 1H, J=8), 7.30 (d, 1H, J=7.6), 7.12 (t, 2H, J=7.2), 6.65 (t, 3H, J=7.2), 3.82 (s, 2H); $^{13}$C NMR (DMSO-d$_6$) 170.19, 166.30, 148.15, 136.56, 131.12, 130.53, 128.98, 125.51, 121.39, 117.23, 112.71, 48.13; MS (EI, m/z) 304 (M$^+$).

Example 47

2-Chloro-11-quindolone

A mixture of 5-chloro-2-[(N-phenylamino)acetamido] benzoic acid from Example 45 (2 g, 6.6 mmol) and polyphosphoric acid (PPA) (30 g) was heated to 100° C. with mechanical stirring. The internal temperature was increased to 125°–135° C. and stirring continued for 35 min. The reaction mixture was cooled to 70° C. and ice-water (20 mL) was carefully added. The resulting mixture was stirred for 10 min, poured in ice-water (~150–200 mL), very slowly quenched with solid NaHCO$_3$ over a 45 min period and diluted with aqueous 15% NaOH to adjust the pH to 7–8. The reaction mixture was allowed to stand for 20 min, and then it was filtered through a filter funnel (size "M"). The product was washed with hot water (70° C., 200 mL) and dried overnight in a vacuum oven (45°–50° C.) to afford the crude title compound as a brown solid (80% yield). This product was dissolved in a small amount of DMSO (~20 mL–30 mL) and diluted with water (~70 mL) to precipitate the pure product and afford, after drying, 1.1 g (63%) of the title compound as a brown solid, mp >300° C.; $^1$H NMR (DMSO-d$_6$) δ 12.66 (s, 1H, NH), 11.81 (s, 1H, NH), 8.28 (d, 1H, J=2), 8.17 (d, 1H, J=8), 7.69 (m, 2H) 7.50 (m, 3H); $^{13}$C NMR (DMSO-d$_6$) δ 166.09, 138.81, 137.47, 130.67, 129.18, 127.75, 125.06, 123.96, 123.71, 120.84, 120.14, 119.13, 115.72, 112.69; MS (EI, m/z) 268 (M$^+$).

Example 48

1-Chloro-11-quindolone

To 6-chloro-2-[(N-phenylamino) acetamido]benzoic acid from Example 46 (0.94 g, 3.0 mmol) was added to 10 g of polyphosphoric acid (PPA) and the mixture was heated at 115°–120° C. After 45 min, TLC analysis showed the disappearance of the starting material. The reaction mixture was stirred for 15 min, cooled to 60° C. and treated with crushed ice. The solution was neutralized with solid NaHCO$_3$, and the resulting solid was filtered (filter funnel, size "M"), washed sequentially with hot (60°–70° C.) water (200 mL), cold water (50 mL) and then dried in a vacuum oven (20 h, 40°–45° C.), yielding 0.63 (76%) of the crude title compound. The compound was dissolved in a minimal amount of DMSO and the resulting solution was diluted with water. The resulting solid product was stirred, filtered, washed with water and dried, affording 0.5 g (61%) of the title compound, mp >300° C.; $^1$H NMR (DMSO-d$_6$) δ 12.52 (s, 1H, NH), 11.65 (s, 1H, NH), 8.14 (d, 1H, J=8), 7.66 (d, 1H, J=8.4), 7.53 (m, 3H), 7.22 (m, 2H); $^{13}$C NMR (DMSO-d$_6$) δ 167.12, 141.61, 138.60, 132.47, 130.17, 127.42, 127.24, 124.51, 123.30, 120.87, 119.06, 118.65, 117.49, 115.63, 112.68; MS (EI, m/z) 268 (M$^+$).

Example 49

2-Chloro-11-chloroquindoline

A mixture of 2-chloro-11-quindolone from Example 47 (0.7 g, 2.6 mmol), PCl$_5$ (0.54 g) and POCl$_3$ (8 mL) was heated at reflux for 30 min. The solution was cooled to rt, concentrated, and then carefully diluted with ice-water. The pH of the resulting mixture was adjusted to 8–9 with 10% NaOH solution, and the resulting crystalline product was filtered, dried for 30 min under vacuum, extracted with hot CHCl$_3$ (~100 mL, 40°–50° C.) with stirring for 30 min, and then filtered from small amount of remaining solid compound while hot. The filtrate was cooled to rt, dried (Na$_2$SO$_4$), and concentrated to afford 0.4 g (53%) of the title compound, mp 281°–281.9° C.; $^1$H NMR (DMSO-d$_6$) δ 11.93 (s, 1H, NH), 8.33 (d, 1H, J=8), 8.24 (t, 2H, J=9.2), 7.73-7.60 (m, 3H), 7.34 (t, 1H, J=8); $^{13}$C NMR (DMSO-d$_6$) δ 146.48, 144.27, 142.04, 131.42, 131.01, 130.70, 130.48, 127.24, 124.36, 121.81, 120.99, 120.73, 120.49, 116.85, 112.13; MS (EI, m/z) 286 (M$^+$).

Example 50

1-Chloro-11-chloroquindoline

A mixture of 1-chloro-11-quindolone from Example 48 (0.6 g, 2.2 mmol), PCl$_5$ (0.5 g) and POCl$_3$ (10 mL) was heated at reflux for 45 min. The resulting solution was cooled to rt, concentrated, and then carefully diluted with ice-water. The pH of the mixture was adjusted to 8–9 with 10% NaOH solution, and the resulting crystalline product was filtered, dried for 30 min under vacuum, extracted with hot CHCl$_3$ (~100 mL, 40°–50° C.) with stirring for 30 min, and then filtered from the small amount of remaining solid compound while hot. The filtrate was cooled to rt, dried, and concentrated to afford 0.28 g (44%) of the title compound, mp 275°–277° C. (became "wet" at 264° C.); $^1$H NMR (DMSO-d$_6$) δ 8.29 (s, 1H, J=7.2), 8.20 (dd, 1H, J=1.2, J=8.8, 7.72-7.57 (m, 4H), 7.32 (dd, 1H, J=1.2, J=14.8); $^{13}$C NMR (DMSO-d$_6$) δ 145.56, 145.53, 132.28, 130.77, 129.90, 129.39, 127.09, 126.02, 121.88, 120.77, 120.46, 120.30, 116.90, 112.18, 79.18; MS (EI, m/z) 286 (M$^+$).

Example 51

2-Chloro-5-methyl-11-chloroquindolinium Hydrochloride

To a suspension of 2-chloro-11-chloroquindoline from Example 49 (0.3 g, 1.0 mmol) in anhydrous toluene (12 mL) was added methyltriflate (0.25 mL, 200 mol %). The reaction mixture was stirred for 20 h at rt after which TLC analysis still showed starting material. Additional methyl triflate (100 mol %) and toluene (5 mL) were added. The reaction mixture was stirred overnight, filtered, washed with ether and dried to afford the crude title compound; MS (-FAB, m/z) 149.

The crude triflate salt obtained above was suspended in CHCl$_3$ (100 mL) and 5% K$_2$CO$_3$ in water (70 mL) was added. The CHCl$_3$ layer was separated and the aqueous layer was extracted with CHCl$_3$ (3×100 mL). Combined CHCl$_3$ extracts were dried over K$_2$CO$_3$ (anhydrous), filtered and concentrated. The resulting solid product was dissolved in CHCl$_3$ and anhydrous K$_2$CO$_3$ was added (100 g). The mixture was sonicated, the solvent was evaporated therefrom, and the resulting adsorbate was loaded onto a basic alumina column. The column was eluted with CHCl$_3$ to remove impurities, eluted with 0.5% MeOH in CHCl$_3$, and then eluted with 1% MeOH in CHCl$_3$. The resulting purple fractions were combined and concentrated to afford a purple solid. The purple solid was dissolved in small amount of CHCl$_3$ and treated with a 1M solution of HCl in ether to afford a yellow product which was filtered, washed with ether and dried to afford the title compound, mp 239°–241° C. (decomp.); $^1$H NMR (DMSO-d$_6$) δ 3.72 (s, 1H, NH), 8.90 (d, 1H, J=8.4), 8.81 (d, 1H, J=7.2), 8.62 (s, 1H), 8.26 (d, 1H, J=8.4), 7.99 (s, 1H), 7.88 (d, 1H, J=7.6), 7.56 (s, 1H), 5.02 (s, 3H); $^{13}$C NMR (DMSO-d$_6$) δ 146.09, 139.06, 134.84, 134.23, 133.18, 132.46, 128.19, 126.65, 124.21, 122.87, 122.18, 121.25, 114.28, 113.49, 112.01, 40.80.

Example 52

1-Chloro-5-methyl-11-chloroquindolinium Hydrochloride

To a suspension of 1-chloro-11-chloroquindoline from Example 50 (0.3 g, 1.0 mmol) in anhydrous toluene (12 mL) was added methyltriflate (0.25 mL, 200 mol %). The reaction mixture was stirred for 20 h at rt after which TLC analysis still showed starting material. Additional methyl triflate (100 mol %) and toluene (5 mL) were added. The reaction mixture was stirred overnight, filtered, washed with ether and dried to afford the crude title compound; MS (-FAB, m/z) 149.

The crude trillate salt obtained above was suspended in CHCl$_3$ (100 mL) and 5% K$_2$CO$_3$ in water (70 mL) was added. The CHCl$_3$ layer was separated and the aqueous layer was extracted with CHCl₃ (3×100 mL). Combined CHCl₃ extracts were dried over K₂CO₃ (anhydrous), filtered and concentrated. The resulting solid product was dissolved in CHCl₃ and anhydrous K₂CO₃ was added (100 g). The mixture was sonicated, the solvent was evaporated therefrom, and the adsorbate was loaded onto a basic alumina column. The column was eluted with CHCl₃ to remove impurities, eluted with 0.5% MeOH in CHCl₃, and then eluted with 1% MeOH in CHCl₃. The resulting purple fractions were combined and concentrated to afford a purple solid. The purple solid was dissolved in small amount of CHCl₃ and treated with a 1M solution of HCl in ether to afford a yellow product which was filtered, washed with ether and dried to afford the title compound, mp 229°–230.8° C. (became "wet" at 225° C.); $^1$H NMR (DMSO-d₆) δ 13.39 (s, 1H, NH, 8.81 (dd, 1H, J=8, J=5.2), 8.33 (s, 1H), 8.16 (d, 1H, J=7.2), 8.12 (d, 1H, J=8.4), 7.97 (d, 1H, J=7.2), 7.88 (d, 1H, J=8.8), 7.55 (d, 1H, J=7.6); $^{13}$C NMR (DMSO-d₆) δ 146.26, 138.35, 137.88, 135.01, 134.09, 131.64, 131.54, 129.94, 128.27, 126.80, 122.29, 120.25, 118.92, 114.17, 113.63, 41.89.

Example 53

2-(Phenoxyacetamido)benzoic Acid

To a solution of anthranilic acid (5 g, 0.036 mol) in NaOH (3 g, 30 mL) was added phenoxyacetyl chloride (6.2 g, 5.2 mL) dropwise at 0° C. The reaction mixture was stirred at 0° C. for 30 min, acidified with dilute hydrochloric acid and filtered. The filtered solid was dissolved in EtOAc and filtered. The filtrate was dried, filtered, concentrated and dried for 4 h under vacuum, affording 8 g (81%) of the title compound, mp 201°–203° C. A small amount (100 mg) of the title compound was recrystallized from EtOH, affording 75 mg of the title compound, mp 202°–203° C.; $^1$H NMR (DMSO-d₆) δ 13.70 (s, 1H, COOH), 12.20 (s, 1H, NH), 8.71 (d, 1H, J=8.4), 8.02 (dd, 1H, J=7.6), 7.65-7.60 (m, 1H), 7.35-6.89 (m, 6H), 4.73 (s, 2H) ; $^{13}$C NMR (DMSO-d₆) δ 169.44, 167.23, 157.11, 140.22, 134.34, 131.32, 129.65, 129.45, 123.06, 121.65, 120.96, 119.45, 116.14, 114.81, 114.38, 67.22; MS (EI, m/z) 271 (M⁺).

Example 54

Benzofuro[3, 2-b]quinolin-6(11H)one

A mixture of 2-(phenoxyacetamido)benzoic acid (2 g, 7.8 mmol) and polyphosphoric acid (10 g) were heated to 120°–125° C. for 1 h. TLC analysis showed the disappearance of starting material and the appearance of one new spot. The solution was treated with crushed ice, neutralized with solid sodium carbonate, and the resulting precipitate was filtered, washed carefully with hot water (70°–80° C., 200 mL), and dried in vacuum oven overnight, affording 1.3 g (76%) of the title compound as pale yellow solid, mp >300° C.; $^1$H NMR (DMSO-d₆) δ 8.33 (d, 1H, J=8), 8.20 (d, 1H, J=7.6), 7.80-7.65 (m, 5H), 7.48 (t, 1H, J=8), 7.36 (m, 1H); $^{13}$C NMR (DMSO-d₆) δ 165.54, 155.64, 139.96, 138.11, 133.79, 131.91, 130.52, 126.06, 125.71, 123.94, 122.38, 122.26, 119.14, 118.89, 113.29; MS (EI, m/z) 235 (M⁺).

Example 55

11-Chlorobenzofuro[3, 2-b]quinoline

A mixture of benzofuro[3, 2-b]quinolin-6(11H) one from Example 54 (1.3 g, 5.5 mmol) and PCl₅ (1.15 g 100 mol %) in of POCl₃ (6 mL) was heated at reflux for 1h. The solution was cooled and concentrated, the residue was partitioned between methylene chloride and 10% sodium hydroxide. The organic layer was separated, dried and concentrated to afford, after drying under high vacuum for 4h, 0.9 g (64%) of the title compound, mp 158°–159° C. [lit 159°–160° C. (Sunder, S.; Peet, N. P. *J. Heterocyclic Chem.* 1978, 15, 1379)]; $^1$H NMR (DMSO-d₆) δ 8.32-8.25 (m, 3H), 7.91-7.77 (m, 4H), 7.57 (t, 1H, J=8); $^{13}$C NMR (DMSO-d₆) δ 158.75, 146.63, 146.02, 143.63, 132.02, 129.37, 129.00, 127.55, 124.63, 124.40, 123.10, 122.29, 122.20, 119.80, 112.75; MS (EI, m/z): 253 (M⁺).

Example 56

11-Chloro-5-methylbenzofuro[3, 2-b]quinoline Trifluoromethanesulfonate

To a suspension of 11-chlorobenzofuro[3, 2-b]quinoline from Example 55 (0.4 g, 1.6. mol) in anhydrous toluene (15 mL) was added methyltriflate (0.52 g, 0.36 mL, 200 mol %). The reaction mixture was stirred for 20 h at rt, diluted with ether, and stirred for 1 h. The solid product was filtered to afford after drying, 0.41 g (62%) of the title compound, mp 221°–223° C. (became "wet" at 200°–202° C.); $^1$H NMR (DMSO-d₆) δ 8.90 (q, 2H, J=8), 8.73 (dd, 1H, J=1.2, J=8), 8.40-8.36 (m, 1H), 8.24-8.14 (m, 3H), 7.83 (m, 1H); $^{13}$C NMR (DMSO-d₆) δ 159.53, 145.04, 142.89, 137.44, 136.69, 134.57, 130.32, 129.93, 127.05, 126.02, 125.43, 125.38, 124.73, 119.23, 116.62, 113.80, 106.93, 40.00; MS (FAB, m/z) 268 (M⁺).

Example 57

Phenylmercaptoacetyl Chloride

To thiophenoxyacetic acid (8 g, 0.05 mol) was added SOCl₂ (8 mL) and the reaction mixture was heated to reflux for 1 h. TLC showed disappearance of the starting material. The excess SOCl₂ was removed in vacuo under a fume hood and the product was distilled to afford 8.6 g (98%) of the title compound, bp 85°–86° C., 4–5 Torr [lit 117°–119° C., 6 Torr (Mooradian, A.; Cavallito, C. J.; Bergman, A. J.; Lawson, E. J.; Suter, C. M. *J. Am. Chem. Soc.* 1949, 3372)]; $^1$H NMR (CDCl₃) δ 7.48-7.34 (m, 5H), 4.06 (m, 2H); $^{13}$C NMR (CDCl₃) 169.75, 132.83, 131.44, 129.35, 128.22, 48.48; MS (EI, m/z) 186 (M⁺).

Example 58

2-(Phenylthioacetamido)benzoic Acid

To a solution of 6.3 g of anthranilic acid in NaOH (4 g of NaOH in 40 mL of water) cooled in an ice-bath was added 8.6 g (0.046 mol) of phenylmercaptoacetylchloride from Example 57. The reaction mixture was stirred for 1 h. The reaction mixture was neutralized with 5% HCl, diluted with water (50 mL), and extracted with EtOAc (3×100 mL). The EtOAc solution was dried, filtered and concentrated to afford after drying under high vacuum, 7.0 g (53%) of the title compound, mp 166°–167° C. [lit 164°–166° C. (Gorlitzer, K.; Weber, J. *Arch. Pharm* (Weinheim) 1980, 314, 76)]; $^1$H NMR (DMSO-d₆) δ 11.82 (s, 1H, COOH), 8.51 (s, 1H, J=8.4), 7.96 (dd, 1H, J=1.2, J=8), 7.58 (t, 1H, J=8), 7.38 (d, 1H, J=7.2), 7.13 (m, 5H), 4.01 (s, 2H); $^{13}$C NMR (DMSO-d₆) δ 169.17, 167.42, 140.31, 135.00, 134.07, 133.72, 131.12, 129.18, 128.07, 126.33, 123.01, 119.77, 116.58, 116.31, 114.54; MS (EI, m/z) 287 (M⁺).

Example 59

Benzothieno[3, 2-b]quinoline-6(11H) one

A mixture of 2-(phenylthioacetamido)benzoic acid from Example 58 (3.0 g, 0.01 mol) and polyphosphoric acid (PPA) (20 g) was heated with mechanical stirring for 90 min at 125°–130° C. The reaction mixture was poured into ice-water (~100 mL) and the pH of this mixture was adjusted carefully with solid $Na_2CO_3$ to pH=7 over a 40 min period. The reaction mixture was filtered to afford a product which was washed with hot water (~70° C.) and dried for 48 h, to afford 2 g (77%) of the title compound, mp >300° C.; $^1$H NMR (DMSO-$d_6$) δ 12.78 (s, 1H, NH), 8.53 (d, 1H, J=7.6), 8.24 (d, 1H, J=8), 8.10 (d, 1H, J=7.6), 7.80-7.64 (m, 4H), 7.40 (t, 1H, J=6.8); $^{13}$C NMR (DMSO-$d_6$) δ 172.37, 140.67, 140.09, 140.08, 132.22, 130.12, 129.08, 124.96, 124.77, 124.14, 123.17, 122.68, 122.13, 118.23; MS (EI, m/z) 251 ($M^+$); IR (KBr) 1623 (C=O), 1522 (C=C), 3098 (NH), 753, 694 (C-S) $cm^{-1}$.

Example 60

11-Chlorobenzothieno[3, 2-b]quinoline

To a solution of benzothieno [3, 2-b]quinoline-6(11H) one from Example 59 (1.0 g, 4.0 mmol) in 5 mL of $POCl_3$ was added $PCl_5$ (0.83 g, 100 mol %). The reaction mixture was refluxed for 20 min. The reaction mixture was concentrated, poured in ice-water, and then the pH was adjusted to 8–9 with 10% NaOH. The resulting solid product was filtered and to it was added $CHCl_3$ (100 mL). The mixture was heated to 30°–40° C. for 30 min. and filtered while hot. The filtrate was dried ($Na_2SO_4$), filtered and concentrated, to afford 0.51 g of the title compound, mp 158°–159° C. [lit 157°–158° C. (Gorlitzer, K.; Weber, J. Arch. Pharm (Weinheim) 1980, 314, 76)]; $^{13}$C NMR (DMSO-$d_6$) δ 8.51 (d, 1H, J=7.6), 8.29 (dd, 1H, J=1.2, J=8), 8.17 (d, 1H, J=8.8), 7.96-7.65 (m, 5H); $^{13}$C NMR (DMSO-$d_6$) δ 153.12, 146.68, 139.82, 133.99, 132.19, 130.96, 130.14, 129.51, 127.90, 126.04, 123.94, 123.79, 123.62, 122.43; MS (EI, m/z) 269 ($M^+$).

Example 61

11-Chloro-5-methylbenzothieno[3, 2-b]quinolinium Trifluoromethanesulfonate

To a solution of 11-chlorobenzothieno[3, 2-b]quinoline from Example 60 (0.16 g; 0.06 mmol) in 12 mL of toluene was added MeOTf (0.081 mL, 120 mol %) and the reaction mixture was stirred at rt for 20 h. The resulting crystalline yellow product was filtered, triturated with EtOAc for 24 h, filtered and dried, providing the title compound (38%), mp 187°–189° C.; $^1$H NMR (DMSO-$d_6$) δ 9.00 (d, 1H, J=8.4), 8.97 (d, 1H, J=8.2), 8.67 (d, 1H, J=8.4), 8.51 (d, 1H, J=8.4), 8.21-7.89 (m, 4H); $^{13}$C NMR (DMSO-$d_6$) δ 148.34, 143.68, 143.11, 139.34, 135.72, 133.95, 130.59, 130.08, 128.35, 127.10, 125.12, 124.89, 119.88, 42.79; MS (+FAB, m/z) 284 ($M^+$) MS (-FAB, m/z) 149.

Example 62

2-(p-Toluenesulfonamido) Acetophenone

To a solution of 2-aminoacetophenone (7.0 g, 0.05 mol) in 30 mL of pyridine was added p-toluenesulfonyl chloride (11.8 g, 120 mol %). The reaction mixture was refluxed with stirring for 2 h, cooled to 40°–50° C. and poured in the cold water (150 mL). The mixture was stirred at rt for 1 h, filtered, washed with warm (~40° C.) water and then dried. Recrystallization from EtOH afforded 7.6 g (51%) of the title compound, mp 148.2°–149.3° C. [lit 147°–148° C. (Kemter, G.; Noack, H.; Russ. G. Z. Chem. 1963, 3, 352)]; $^1$H NMR (CDCl$_3$) δ 11.48 (s, 1H, NH), 7.79 (dd, 1H, J=1.2, J=6.8), 7.72 (d, 1H, J=8.4), 7.67 (d, 1H, J=8.4), 7.44 (t, 1H, J=8), 7.21 (d, 1H, J=8), 7.02 (t, 1H, J=6), 2.55 (s, 3H), 2.36 (s, 3H); $^{13}$C NMR (CDCl$_3$) δ 202.37, 143.83, 139.94, 136.47, 134.82, 131.87, 129.57, 127.16, 122.55, 122.18, 118.92, 28.04, 21.42; MS (EI, m/z) 289 ($M^+$).

Example 63

2-(2-Toluenesulfonamidobenzoyl)-1-indanone

Sodium metal (0.62 g) was carefully dissolved in 27 mL of MeOH to obtain a solution of MeONa. To a solution of phthalaldehyde (1.8 g 0.013 mol) and 2-(p-toluenesulfonamido) acetophenone from Example 63 (3.91 g 100 mol %) in MeOH (54 mL) was added dropwise the solution of MeONa obtained above over a 20 min period. The reaction mixture was refluxed for 7 h by stirring and was allowed to stir at rt overnight. The pH of the reaction mixture was adjusted with conc. HCl to pH=5 and the resulting crystalline compound was filtered. Recrystallization from EtOH/CHCl$_3$ afforded 2.5 g (46%) of the title compound as a light-pink solid, mp 176°–177° C. [lit 176°–177° C. (G örlitzer, K.; Weber, J. Arch. Pharm (Weinheim) 1979, 312, 254)]; $^1$H NMR (CDCl$_3$) δ 8.53 (s, 1H, NH), 7.72 (d, 1H, J=7.2), 7.59 (d, 1H, J=8), 7.46-7.25 (m, 7H), 7.13 (t, 1H, J=7.6), 6.66 (d, 2H, J=8.4), 3.06 (s, 2H), 1.40 (s, 3H); $^{13}$C NMR (CDCl$_3$) δ 189.45, 176.75, 147.25, 143.33, 136.53, 135.55, 135.47, 135.45, 132.84, 131.56, 128.78, 128.26, 128.22, 127.40, 126.99, 126.89, 126.59, 125.38, 125.03, 122.91, 111.25, 32.04, 20.02; MS (EI, m/z) 250 ($M^+$).

Example 64

11-Oxo-5,11-dihydro-indeno[1, 2-b]quinoline

A mixture of 2-(2-toluenesulfonamidobenzoyl)-1-indanone from Example 63 (2.2 g, 5.5 mmol) and polyphosphoric acid (PPA) (20 g) was heated to 120°–122° for 1 h. The reaction mixture was poured into ice-water and the resulting crystalline product was filtered, washed with hot water and dried for several days in a vacuum oven, affording 1.15 g (88%) of the title compound which was refluxed with 80 mL of benzene for 30 min, affording 0.95 g (73%) of the title compound, mp >300° C. with prior discoloring at 174°–179° C. [lit >360° C. Blount, B. K.; Perkin, W. H.; Plant, S. G. P. J. Chem. Soc. 1929, 1975; lit 363–364 (Schoen, J.; Bogdanowicz- Szwed, K. Rocz. Chem. 1964, 38, 425)]; $^1$H NMR (DMSO-$d_6$) δ 8.24 (d, 1H, J=8), 8.18 (dd, 1H, J=3.2, J=2), 7.80-7.55 (m, 3H), 7.56 (d, 1H, J=3.2), 7.55 (d, 1H, J=3.48), 7.43 (t, 2H, J=7.6), 3.84 (s, 2H); $^{13}$C NMR (DMSO-$d_6$) δ 144.91, 139.96, 135.57, 131.69, 130.10, 129.93, 128.30, 127.23, 125.75, 124.78, 124.55, 123.48, 121.51, 119.25, 118.52, 32.84; MS (+LSIMS, m/z) 234 (M+H$^+$); MS (EI, m/z) 233 ($M^+$).

Example 65

Benzothieno[3,2-b]quinoline-6-(11H) one-S,S-dioxide

A solution of benzothieno[3,2-b]quinoline-6-(11H) one from Example 59 (0.25 g, 0.99 mmol) in AcOH (5 mL) was heated to 40° C. and then 30% $H_2O_2$ (1 mL) was added dropwise. The reaction mixture was stirred at 40° C. for 2 h, upon which TLC analysis showed the disappearance of the starting material. The reaction mixture was cooled to 10° C., $H_2O$ was added, and the mixture was stirred and filtered. The filtered solid was washed with water and air-dried for 20 h, and then dried under high vacuum, yielding 0.21 g (74%) of the title compound, mp >300° C. The final product contains a small amount of an N-oxide impurity. The presence of the N-oxide was established by the presence of N-O stretching frequency at 1335 cm$^{-1}$ [Cromwell, N. H.; Mitsch, R. A. *J. Org. Chem.* 1961, 26, 3812]; $^1$H NMR (DMSO-d$_6$) δ 13.2 (br. signal NH), 8.40 (d, 1H, J=7.6), 8.21 (d, 1H, J=8), 8.05 (d, 1H, J=7.2), 7.96-7.82 (m, 4H), 7.53 (m, 1H). $^{13}$C NMR (DMSO-d$_6$) δ 140.61, 133.91, 133.86, 133.34, 133.33, 133.08, 132.82, 132.43, 127.49, 125.52, 125.15, 123.90, 123.82, 121.48. MS (+LSIMS): 284. MS (+EI):284. IR (KBr): 1626 (C=O), 1533 (C=C), 1302 (SO$_2$), 1335 (NO), 3250 (NH), 760, 695 (C-S).

Example 66

11-Chloro-indeno[1, 2-b]quinoline

A solution of 11-oxo-5,11-dihydro-indeno[1, 2-b] quinoline from Example 64 (0.30 g, 1.3 mmol) in POCl$_3$ (10 mL) was refluxed for 3 h. The POCl$_3$ was evaporated off and the oily product was poured over ice-water. The mixture was neutralized to pH=8 with 10% aqueous KOH and extracted with CH$_2$Cl$_2$. The combined organic fractions were dried (Na$_2$SO$_4$), filtered, and concentrated to afford 0.21 g (66%) of the title compound, mp 148°–149° C. [lit 162°–163° C. (Schoen, J.; Bogdanowicz-Szwed, K. *Rocz. Chem.* 1964, 38, 425)]; $^1$H NMR (CDCl$_3$) δ 8.27 (d, 2H, J=6.4), 8.21 (d, 1H, J=8.4), 7.78-7.74 (m, 1H), 7.64-7.60 (m, 2H), 7.54-7.51 (m, 2H), 4.08 (s, 2H); $^{13}$C NMR (CDCl$_3$) δ 161.35, 149.12, 144.26, 140.13, 137.74, 132.99, 130.42, 129.57, 129.42, 127.71, 126.52, 125.46, 125.25, 123.63, 122.33, 34.18; MS (FAB, m/z) 252 (M$^+$).

Example 67

11-Chloro-5-methylindeno[1, 2-b]quinolinium Trifluoromethanesulfonate

To a solution of 11-chloro-indeno[1, 2-b]quinoline from Example 66 (0.089 g, 0.35 mmol) in toluene (8 mL) was added methyl triflate (0.048 mL, 0.42 mmol). The reaction mixture was stirred for 20 h at room temperature during which time a crystalline product precipitated from the reaction mixture. The reaction mixture was diluted with diethyl ether and was allowed to stir for 1 h at room temperature. The mixture was filtered and the crystalline solid was dried under high vacuum for several hours. The crystalline solid compound was refluxed for 1 h with benzene and dried to afford 0.113 g (77%) of the title compound, mp 193°–194° C.; $^1$H NMR (DMSO-d$_6$) δ 8.82 (d, 1H, J=8), 8.73 (d, 1H, J=8.4), 860 (d, 1H, J=8.4), 8.32 (m, 1H), 8.13 (t, 1H, J=7.6), 8.02-7.93 (m, 2H), 7.79 (t, 1H, J=7.2) 4.88 (s, 3H), 4.51 (s, 2H); $^{13}$C NMR (DMSO-d$_6$) δ 157.70, 148.30, 144.16, 139.51, 136.34, 134.85, 134.71, 133.09, 130.04, 128.83, 126.80, 125.39, 124.86, 119.81, 40.97, 34.97; MS (FAB, m/z) 266 (M$^+$).

Example 68

11-Chlorobenzothieno[3,2-b]quinoline-S,S-dioxide

A solution of benzothieno[3,2-b]quinoline-6-(11H) one-S,S-dioxide from Example 65 (0.1 g, 0.35 mmol) and PCl$_5$ (74 mg) in POCl$_3$ (6 mL) was refluxed for 3.5 h. The reaction mixture was poured over ice-water, and neutralizated to pH=8 with 10% aqueous KOH. The precipitated solution was extracted with CHCl$_3$ and combined organic extracts were dried (Na$_2$SO$_4$), filtered and concentrated to afford 30 mg (27%) of the title compound, mp 266°–269° C. [lit 283°–285° C. [Gorlitzer, K.; Weber, J. *Arch. Pharm* (Weinheim) 1980, 314, 76)]; $^1$H NMR (CDCl$_3$) δ 8.62 (d, 1H, J=6.4), 8.36 (s, 1H), 8.20 (d, 1H, J=7.2), 7.96-7.59 (m, 5H); $^{13}$C NMR (CDCl$_3$) d 134.46, 133.19, 132.91, 130.32, 129.83, 129.44, 129.00, 127.09, 125.47, 125.01, 124.31, 123.27, 123.15, 122.79, 121.87; MS (EI, m/z) 301 (M$^+$).

Example 69

11-(4-Chlorophenylthio)-5-methylbenzofuro [3, 2-b]quinolinium Chloride

To a solution 11-chloro-5-methylbenzofuro[3, 2-b] quinoline trifluoromethanesulfonate from Example 56 (65 mg, 0.156 mmol) in 2-ethoxyethanol (5 ml) was added 4-chlorothiophenol (23 mg, 0.156 mmol) causing the reaction mixture to became a bright yellow. After 5–7 min, TLC showed the disappearance of the starting material. The reaction mixture was cooled to room temperature, diluted with hexane (100 mL), cooled below room temperature, filtered and dried to afford 50 mg (63%) of the title compound, mp 150°–151° C.; $^1$H NMR (CDCl$_3$) δ 8.71 (d, 1H, J=7.6), 8.60 (s, 2H), 8.23 (s, 1H), 7.96 (s, 1H), 7.86 (t, 1H, J=6.8), 7.64 (m, 2H), 7.44-7.37 (m, 4H), 5.06 (s, 3H); $^{13}$C NMR (CDCl$_3$) δ 159.65, 146.54, 140.91, 139.53, 137.16, 136.95, 136.13, 135.33, 135.10, 130.24, 129.26, 127.46, 126.74, 126.65, 126.48, 126.08, 119.23, 116.29, 113.54, 41.25; MS (FAB, m/z) 376 (M$^+$).

Example 70

11-[(4-Chlorophenyl)thio]-5-methylindeno [1, 2- b] quinolinium Chloride

To a solution of 11-chloro-5-methylindeno[1, 2-b] quinolinium trifluoromethanesulfonate from Example 67 (50 mg, 0.12 mmol) in 2-ethoxyethanol (4 mL) was added 4-chlorothiophenol (17.5 mg, 0.12 mmol) causing the reaction mixture to become yellow color. After refluxing for 12–15 min a small amount of precipitate formed and TLC showed the disappearance of the starting material. The mixture was cooled to room temperature, diluted with hexane (25 mL), cooled below room temperature, filtered, and dried to afford 30 mg (51%) of the title compound, mp 174°–175° C. (dec.); $^1$H NMR (CD$_3$OD) δ 8.74 (dd, 1H, J=1.2, J=7.2), 8.64 (t, 2H, J=9.6), 8.24-8.20 (m, 1H), 7.95 (t, 1H, J=8.4), 7.85 (m, 2H), 7.79-7.77 (m, 1H), 7.50-7.40 (m, 4H), 5.05 (s, 3H), 3.98 (s, 2H).

Example 71

2-Fluoroquindoline-11-carboxylic Acid

A 5° C. solution of 3-fluoroisatin (4.71 g, 28.5 mmol) in 4N KOH (135 mL, 456 mmol) was added to a nitrogen-purged flask containing indolyl acetate (5.00 g, 28.5 mmol). The mixture was mechanically stirred for 5 days at room temperature. Water (80 mL) was added and the solution was heated at 70° C. for 20 minutes with air being drawn through the solution. The solution was hot filtered through a bed of celite and the celite bed was rinsed with warm water (75 mL). The yellow filtrate was combined with an equal volume of ethanol (300 mL). The mixture was acidified to pH 2 with dilute HCl, cooled below room temperature, and filtered. The filter cake was washed with water and ethanol and dried under high vacuum for two days which afforded 4.91 g (61%) of the title compound as a bright yellow solid, mp >243° C.; $^1$H NMR (DMSO-d$_6$) δ 14.3 (broad s, 1H), 11.49 (s, 1H), 8.88 (dd, J=12.8, J=2.8, 1H), 8.34 (broad d, J=8.8, 1H), 8.32 (d, J=9.2, 1H), 7.79 (d, J=8.4, 1H), 7.59–7.68 (m, 2H), 7.34 (td, J=7.4, J=0.8, 1H); $^{13}$C NMR (DMSO-d$_6$) δ 167.66, 160.45 (J=245), 147.27 (J=2), 144.44, 140.48, 132.87, 132.22 (J=10), 130.51, 124.70 (J=11), 121.22, 120.57, 120.48, 115.85 (J=27), 112.70, 112.66, 109.80 (J=9), 108.53 (J=26); MS (EI, m/z) 280.1 (M$^+$).

Example 72

2-Fluoroquindoline

2-Fluoroquindoline-11-carboxylic acid from Example 71 (4.50 g, 16.1 mmol) was refluxed at 250° C. in diphenyl ether (40 mL) for 4 hours. The mixture was cooled, diluted with petroleum ether (40 mL), and filtered. The filter cake was washed with petroleum ether (100 mL) and dried. The crude material was added to methanol (250 mL) and filtered, washing with additional methanol (2×75 mL). Concentration of the filtrate afforded 2.47 g (65%) of the title compound as a brown solid, mp >246° C.; $^1$H NMR (DMSO-d$_6$) δ 11.52 (s, 1H), 8.34 (d, J=8, 1H), 8.28 (s, 1H), 8.24 (dd, J=9.2, J=5.6, 1H), 7.90 (dd, J=10, J=2.8, 1H), 7.50–7.65 (m, 3H), 7.29 (t, J=8, 1H); $^{13}$C NMR (DMSO-d$_6$) δ 158.96 (J=244), 145.53, 143.97, 140.42, 132.86, 131.22 (J=10), 129.83, 127.25, 121.31, 120.84, 119.54, 116.23 (J=27), 112.47 (J=5.3), 111.58, 110.01 (J=22); MS (EI, m/z) 236.1 (M$^+$).

Example 73

2-Fluoro-5-methylquindolinium Hydrochloride

In a large teflon lined steel bomb fitted with a stir bar was placed 2-fluoroquindoline from Example 72 (0.500 g, 2.12 mmol) and methyl iodide (3.95 mL, 63.5 mmol). The bomb was flushed with nitrogen, sealed, and heated to 150° C. for 24 h. The bomb was cooled, opened and the contents were transferred to a flask using chloroform to wash the inside of the bomb. The chloroform suspension was concentrated to a dry orange residue. The orange residue was suspended in chloroform, adsorbed onto Na$_2$CO$_3$ and chromatographed over basic alumina using 100% chloroform eluent until starting material could not be detected by TLC. The column was eluted with 2% methanol in chloroform and the violet fractions were collected and concentrated to a small volume (~50 mL). The violet solution was acidified with ethereal 1M HCl to a bright yellow endpoint. The mixture was cooled below room temperature, filtered and dried under high vacuum for several days at 45° C. to yield 0.413 g (68%) of the title compound as a bright orange solid, mp >246° C.; $^1$H NMR (DMSO-d$_6$) δ 13.40 (s, 1H), 9.25 (s, 1H), 8.88 (dd, J=10, J=4.4, 1H), 8.80 (d, J=8.4, 1H), 8.44 (dd, J=8.8, J=2.8, 1H), 8.11 (td, J=6.8, J=2.8, 1H), 7.94 (t, J=15.2, 1H), 7.85 (d, J=8.4, 1 H) , 7.51 (t, J=8.0, 1H), 5.05 (s, 3H); $^{13}$C NMR (DMSO-d$_6$) δ 159.35 (J=249), 145.89, 138.28, 134.08 (J=11), 132.39, 127.39 (J=10), 126.37, 123.62 (J=5.3), 121.86 (J=27), 121.41, 121.19 (J=9), 113.70, 113.20, 112.65 (J=24), 40.74; MS (LSIMS, m/z) 251 (M$^+$).

Example 74

7-Bromo-8-chloroquindoline-11-carboxylic Acid

A 5° C., nitrogen-purged solution of isatin (2.55 g, 17.3 mmol) in 4N KOH (80 mL, 277 mmol) was added to a nitrogen-purged flask containing 5-bromo-6-chloro indolyl acetate (5.00 g, 17.3 mmol). The mixture was mechanically stirred for 5 days at room temperature. Water (80 mL) was added, and the solution was heated to 70° C. for 20 minutes while air was drawn through the solution. The solution was hot filtered through a bed of celite and the celite bed was rinsed with warm water (75 mL). The yellow filtrate was combined with an equal volume of ethanol (300 mL). The mixture was acidified to pH 2 with dilute HCl, cooled below room temperature, and filtered. The filter cake was washed with water and ethanol and dried under high vacuum for two days to yield 3.32 g (51%) of a yellow solid, mp >243° C.; $^1$H NMR (DMSO-d$_6$) δ 14.2 (broad s, 1H), 11.60 (s, 1H), 9.10 (m, 1H), 8.63 (s, 1H), 8.26 (m, 1H), 7.97 (s, 1H), 7.71–7.77 (m, 2H); $^{13}$C NMR (DMSO-d$_6$) δ 167.44, 145.22, 143.78, 143.73, 134.01, 132.64, 129.63, 127.45, 126.57, 125.57, 125.08, 123.93, 122.60, 121.23, 114.04, 112.12; MS (EI, m/z) 375.9 (M+2$^+$).

Example 75

7-Bromo-8-chloroquindoline

7-Bromo-8-chloroquindoline-11-carboxylic acid from Example 74 (3.00 g, 7.99 mmol) was refluxed at 250° C. in diphenyl ether (30 mL) for 4 hours in an oversize flask. The mixture was cooled, diluted with petroleum ether (30 mL), and filtered. The filter cake was washed with petroleum ether (100 mL) and dried under high vacuum to yield 2.49 g (94%) of the title compound as a greenish solid, mp >246° C.; $^1$H NMR (DMSO-d$_6$) δ 11.70 (s, 1H), 8.62 (s, 1H), 8.36 (s, 1H), 8.18 (d, J=8.4, 1H), 8.12 (d, J=8.4, 1H), 7.84 (s, 1H),7.69 (t, J=6.8, 1H), 7.59 (t, J=7.2, 1H); $^{13}$C NMR (DMSO-d$_6$) δ 143.65, 143.15, 133.39, 132.95, 128.65, 127.66, 127.97, 126.75, 125.51 (two signals), 121.53, 114.34, 113.10, 111.11; MS (EI, m/z) 331.9 (M+2$^+$).

Example 76

7-Bromo-8-chloro-5-methylquindolinium Hydrochloride

In a large teflon lined steel bomb fitted with a stir bar was placed 7-bromo-8-chloroquindoline from Example 75 (0.350 g, 1.06 mmol) and methyl iodide (1.97 mL, 31.7 mmol). The bomb was flushed with nitrogen, sealed, and heated to 150° C. for 24 h. The bomb was cooled, opened and the contents were transferred to a flask using chloroform to wash the inside of the bomb. The chloroform suspension was concentrated to a dry orange residue. The orange residue was suspended in chloroform, adsorbed onto Na$_2$CO$_3$ and chromatographed over basic alumina using 100% chloroform until starting material could not be detected by TLC. The column was eluted with 2% methanol in chloroform and the violet fractions were collected. After concentrating to a small volume (~50 mL) the violet solution was acidified with ethereal 1M HCl to a bright yellow endpoint. The mixture was cooled below room temperature, filtered and dried under high vacuum at 45° C. for several days to yield 0.311 (77%) of the title compound as a bright orange solid, mp >246° C.; $^1$H NMR (DMSO-d$_6$) δ 13.33 (s, 1H), 9.38 (s, 1), 9.21 (s, 1H), 8.82 (d, J=8.8, 1), 8.60 (d, J=8.0, 1H), 8.17–8.35 (m, 2H), 7.98 (t, J=7.6, 1H) , 5.02 (s, 3H); $^{13}$C NMR (DMSO-d$_6$) δ 144.42, 137.91, 136.67, 135.73, 133.85, 133.09, 130.27, 130.00, 127.53, 126.76, 126.08, 118.02, 114.48, 114.36, 113.63, 40.46; MS (LSIMS, m/z) 347 (M+2$^+$).

Example 77

7-Bromo-6-chloroquindoline-11-carboxylic Acid

A 5° C., nitrogen-purged solution of isatin (2.23 g, 5.1 mmol) in 6N KOH (40 mL, 242 mmol) was added to a nitrogen-purged flask (using an additional 21 mL H$_2$O to aid transfer, final KOH concentration was 4M) containing 5-bromo-6-chloro-indolyl diacetate (5.00 g, 15.1 mmol). The mixture was mechanically stirred for 11 days at room temperature. Water (100 mL) was added and the solution was heated to 70° C. for 20 minutes while oxygen bubbled through the solution. The solution was hot filtered through a bed of celite and the celite bed was rinsed with warm water (70 mL). The yellow- brown filtrate was combined with an equal volume of ethanol (250 mL). The mixture was acidified to pH 2 with dilute HCl, cooled below room temperature, and filtered. The filter cake was washed sequentially with water, ethanol, and then dried under high vacuum for two days to afford 1.82 g (32%) of the title compound as a yellow solid; $^1$H NMR (DMSO-d$_6$) δ 14.2 (broad s, 1H), 11.77 (s, 1H), 9.07–9.11 (m, 1H), 8.26–8.29 (m, 1H), 7.95 (dd, J=8.8, J=1.6, 1H), 7.69–7.75 (m, 3H); $^{13}$C NMR (DMSO-d$_6$) δ 167.56, 145.19, 144.49, 143.71, 134.00, 132.11, 130.14, 127.77, 127.56, 126.43, 124.96, 123.57, 118.76, 113.24, 112.89, 112.01; MS (EI, m/z) 347 (M+2$^+$).

Example 78

7-Bromo-6-chloroquindoline

7-Bromo-6-chloroquindoline-11-carboxylic acid from Example 77 (1.75 g, 4.66 mmol) was refluxed at 252° C. in diphenyl ether (30 mL) for 4 hours in an oversize flask. The mixture was cooled, diluted with petroleum ether (30 mL), and filtered. The filter cake was washed with petroleum ether (100 mL) and dried to yield 1.48 g (96%) of the title compound as a brown solid; $^1$H NMR (DMSO-d$_6$) δ 11.92 (s, 1H), 8.39 (s, 1H), 8.21 (d, J=8.4, 1H), 8.13 (d, J=7.6, 1H), 7.90 (d, J=8.4, 1H), 7.69 (t, J=7.6, 1H), 7.60 (td, J=7.6, J=1.6, 1H), 7.52 (d, J=8.8, 1H); $^{13}$C NMR (DMSO-d$_6$) δ 143.88, 143.64, 143.59, 133.31, 132.56, 129.23, 127.82, 127.53, 126.62, 125.62, 119.09, 118.6, 113.96, 112.14, 111.89.

Example 79

2-(N-Bromoacetylamino)benzoic Acid

A solution of anthranilic acid (50 g, 364.6 mmol) in anhyd DMF (125 mL) and dioxane (125 mL) in a 1 L Morton flask equipped with a mechanical stirrer and a constant addition funnel was cooled with an ice-bath to 0° C. Freshly distilled bromoacetyl bromide (73.6 g, 31.77 mL, 364.6 mmol) was added dropwise keeping the internal temperature between 0°–1.5° C. over a 2.5 hour period. After addition of the bromoacetyl bromide was completed, the ice-bath was removed and stirring at rt was continued for 5 h. The reaction mixture was cooled in an ice-bath and slowly diluted with water (300 mL). A white precipitate formed, which was filtered, washed sequentially with 5% HBr solution (500 mL) and water (500 mL), and then dried in a vacuum desiccator. Further drying in a vacuum oven at 60° C. afforded 82.61 g (87.8%) of the title compound as a white powder, mp 164.6°–167.6° C. [lit 165.5°–172° C. (Hoffman LaRoche U.S. Pat. No. 3,244,698)]; $^1$H NMR (DMSO-d$_6$) δ 13.7 (bs, 1H), 11.60 (s, 1H), 8.44 (d, J=8.0, 1H), 8.00 (dd, J=8.0, J=1.6, 1H), 7.62 (dt, J=8.0, J=1.6, 1H), 7.21 (t, J=8.0, 1H); 4.26 (s, 2H); $^{13}$C NMR (DMSO-d$_6$) δ 169.20, 165.05, 139.95, 134.08, 131.13, 123.46, 120.02, 117.09, 30.67; MS (EI, m/z) 256.9 (M$^+$), 258.9 (M$^{3O}$ 2$^+$).

Example 80

2-[[N-(phenyl)amino]acetamido]benzoic Acid

A solution of 2-(N-Bromoacetylamino)benzoic acid from Example 79 (5.0 g, 19.37 mmol), aniline (4.51 g, 4.41 mL, 48.4 mmol) and anhyd DMF (50 mL) was heated in an oil bath at 85° C. for 4.5 h. The reaction mixture was cooled and poured into ice-water (500 mL). A solution of 5% KOH (100 mL) was added to dissolve the milky white suspension and the resulting homogenous solution was extracted with CH$_2$Cl$_2$ (200 mL, 2×100 mL). The combined CH$_2$Cl$_2$ extract was set aside and the aqueous layer was acidified to pH=3 (pH meter) with 5% HBr. The resulting precipitate was washed with 5% HBr solution and water, and then dried in a vacuum oven at 50° C. for 2 days, yielding 4.74 g (90.6%) of a white powder, mp 192.4°–192.8° C. (sealed tube); $^1$H NMR (DMSO-d$_6$) 13.41 (bs, 1H), 12.01 (s, 1H), 8.72 (d, J=8.4, 1H), 7.93 (dd, J=7.6, J=1.6, 1H), 7.59 (dt, J=8.8, J=1.6, 1H), 7.15-7.05 (m, 3H), 6.63-6.45 (m, 4H); 3.83 (s, 2H); $^{13}$C NMR (DMSO-d6) δ 170.85, 169.01, 148.11, 140.56, 134.13, 131.10, 128.94, 122.63, 119.38, 117.10, 115.96, 112.40, 48.93; MS (EI, m/z) 270.1 (M$^+$).

Example 81

11-Quindolone

A suspension of 2-[[N-(phenyl)amino]acetamido] benzoic acid from Example 80 (3.0 g, 11.10 mmol) and polyphosphoric acid (PPA) (100 g) was heated to 130° C. with mechanical stirring. The reaction mixture was poured into ice-water (300 mL) and stirred. The pH of the reaction mixture was adjusted to 8 by slowly adding saturated NaHCO$_3$ solution. The resulting green precipitate was filtered and washed with water. After drying the solid precipitate in a vacuum oven at 50° C. overnight, 5.38 g (>100%) of a green powder was obtained; $^1$H NMR (DMSO-d$_6$) δ 12.5 (bs, 1H), 11.70 (s, 1H), 8.34 (dd, J=8.0, J=0.8, 1H), 8.18 (d, J=7.6, 1H), 7.72 (d, J=8.4, 1H), 7.69 (dt, J=8.4, J=1.2, 1H), 7.51 (d, J=8.4, 1H), 7.46 (t, J=7.6, 1H), 7.28 (dt, J=8.0, J=1.2, 1H), 7.19 (dt, J=7.2, J=0.8, 1H); $^{13}$C NMR (DMSO-d$_6$) δ 167.33, 139.09, 138.59, 130.58, 128.98, 127.35, 125.15, 123.06, 122.85, 120.80, 120.40, 118.83, 117.80, 115.90, 112.96; MS (EI, m/z) 234 (M$^+$).

Example 82

11-Chloroquindolinium Chloride and 11-Chloroquindoline

A suspension of 11-quindolone (4.5 g) from Example 81 and freshly distilled POCl$_3$ (50 mL) was heated to reflux for 2 h. The mixture was cooled and the excess POCl$_3$ was removed in vacuo under a fume hood. The resulting residue was poured into ice-water (100 mL) and the pH of the mixture was adjusted to 8 with saturated NaHCO$_3$ solution. Dichloromethane (250 mL) was added, the mixture was stirred and then the layers were separated. The aqueous layer was extracted with additional dichloromethane (2×250 mL) and the combined dichloromethane layers were sequentially washed with brine (500 mL) and water (500 mL), and then dried (Na$_2$SO$_4$). Filtration followed by concentration of the filtrate afforded a yellow solid which was recrystallized (at −20° C.) from isopropanol-chloroform (2:1, 200 mL) to afford 1.18 g (50.4%) of 11-chloroquindolinium chloride as a yellow solid, mp 258.4°–261.2° C.; $^1$H NMR (DMSO-d$_6$) δ 12.5 (s, 1H), 8.73 (d, J=8.0, 1H), 8.54 (d, J=8.4, 1H), 8.41 (dd, J=8.4, J=1.2, 1H), 8.33 (s, 1H), 7.98 (dt, J=7.6, J=0.8, 1H), 7.88 (dt, J=7.6, J=0.8, 1H), 7.80 (dt, J=7.2, J=0.8, 1H), 7.71 (d, J=8.0, 1H), 7.43 (dt, J=7.2, J=0.8, 1H); $^{13}$C NMR (DMSO-d$_6$; quaternary carbons broadened and indistinguishable) δ 144.99, 136.69, 131.15, 129.70, 127.44, 123.82 (br), 123.25, 122.98, 121.07, 112.68; MS (EI, m/z) 252 (M$^+$), 254 (M+2$^+$).

The filtrate was concentrated and adsorbed onto neutral alumina. The adsorbate was poured onto a silica gel column and eluted with hexane-ethyl acetate (2:1) to afford 0.30 g (12.8%) of 11-chloroquindoline as a yellow solid, mp 220.3°–222.3° C. [lit 220°–224° C. (Yamato, M.; Takeuchi, Y.; Chang, M.-r.; Hashigaki, K.; Tsuruo, T.; Tashiro, T.; Tsukagoshi, S. *Chem. Pharm. Bull.* 1990, 38, 3048)]; $^1$H NMR (DMSO-$d_6$) δ 11.84 (s, 1H), 8.36 (d, J=7.6, 1H), 8.33-8.25 (m, 2H), 7.81-7.60 (m, 4H), 7.34 (dt, J=8.0, J=0.8, 1H); $^{13}$C NMR (DMSO-$d_6$) a 146.07, 144.15, 143.84, 130.39, 130.11, 129.29, 126.85, 126.38, 123.63, 122.13, 121.72, 121.19, 120.24, 117.97, 112.04; MS (EI, m/z) 252 ($M^+$), 254 ($M+2^+$).

The 11-chloroquindolinium salt was converted to it free base form, 11-chloroquindoline upon treatment with 5% $K_2CO_3$ solution or 5% KOH solution and extraction into chloroform in quantitative yield.

Example 83

11-Chloro-5-methylquindolinium hydrotrifluoromethane sulfonate

A suspension of 11-chloroquindoline (0.54 g, 2.13 mmol) from Example 82 and methyl triflate (699 mg, 482 μL, 4.26 mmol) was stirred at rt for 2 days. The reaction mixture was filtered and the product was washed with diethyl ether and dried, yielding 0.86 g (97.7%) of crude 11-Chloro-5-methylquindolinium hydrotrifluoromethane sulfonate as an orange solid; $^1$H NMR (DMSO-$d_6$) δ 13.28 (s, 1H), 8.86 (t, J=9.2, 2H), 8.68 (J=8.40, 1H), 8.27 (t, J=8.4, 1H), 8.11 (t, J=8.4, 1H), 8.00 (t, J=8.4, 1H), 7.87 (d, J=8.0, 1H), 7.57 (t, J=8.0, 1H), 5.04 (s, 3H); $^{13}$C NMR (DMSO-$d_6$) δ 145.86, 138.87, 135.82, 134.62, 132.79, 131.85, 128.89, 128.42, 126.67, 124.58, 123.40, 122.09, 118.78, 114.56, 113.46, 40.47; MS (+FAB, m/z) 267 ($M^+$), 269 ($M^+2+$).

A suspension of the 11-chloro-5-methylquindolinium hydrotrifluoromethane sulfonate (184 mg, 0.44 mmol) obtained above, anhydrous $Na_2CO_3$ (5 scoops) and chloroform was sonicated and concentrated to dryness. The adsorbate was loaded onto a basic alumina column and eluted with chloroform to remove the quindoline impurity. Elution with 5% methanol in chloroform afforded 120 mg of 11-chloro-5-methylquindoline as a purple solid. The purple solid was dissolved in chloroform (20 mL) and acidified to a yellow endpoint with a 1M solution of HCl in ether. Filtration and washing of the solid with ether afforded, after drying, 123 mg of the pure title compound as a yellow solid; $^1$H NMR (DMSO-$d_6$) δ 13.51 (s, 1H, 8.87 (d, J=9.2, 1H), 8.83 (d, J=8.8, 1H), 8.66 (dd, J=8.8, J=1.2, 1H), 8.29-8.23 (m, 1H), 8.10 (t, J=8.4, 1H), 7.97 (t, J=8.0, 1H), 7.89 (d, J=8.4, 1H), 7.56 (dt, J=8.0, J=1.2, 1H), 5.03 (s, 3H); $^{13}$C NMR (DMSO-$d_6$) δ 145.94, 138.79, 135.80, 134.54, 132.78, 131.81, 128.91, 128.40, 126.64, 124.60, 123.38, 122.06, 118.81, 114.48, 113.53, 40.49; MS (+FAB, m/z) 267 ($M^+$), 269 ($M^+2^+$).

Example 84

2-[[N-(4-Methoxyphenyl)amino]acetamido]benzoic Acid

A solution of 2-(N-bromoacetylamino)benzoic acid from Example 79 (8.00 g, 31.0 mmol) , para-methoxyaniline (9.55 g, 77.5 mmol) and DMF (80 mL) was heated to 80° C. for 8 h. The mixture was cooled, poured over $H_2O$ (1 L) and 5% KOH (300 mL) and washed with $CH_2Cl_2$ (3×300 mL). The aqueous layer was acidified to pH 2 with 2N HCl, cooled below room temperature, and filtered. The filter cake was rinsed with cold water (100 mL) and dried under high vacuum at 45° C. to yield 7.62 g (85%) of the title compound as a white solid; $^1$H NMR (DMSO-$d_6$) δ 13.5 (broad s, 1H), 12.04 (s, 1H), 8.73 (dd, J=8.4, J=1.0, 1H), 7.93 (dd, J=7.8, J=1.8, 1H), 7.59 (td, J=8.0, J=1.8, 1H), 7.13 (td, J=7.6, J=1.2, 1H), 6.73 (dt, J=8.8, J=2.2, 2H), 6.54 (dt, J=9.2, J=2.4, 2H), 6.2 (broad s, 1H), 3.77 (s, 2H), 3.62 (s, 3H); $^{13}$C NMR (DMSO-$d_6$) δ 171.18, 168.95, 151.53, 142.2, 140.58, 134.12, 131.12, 122.62, 119.42, 116.03, 114.57, 113.42, 55.20, 49.76; MS (EI, m/z) 300 ($M^+$).

Example 85

2-[[N-(4-Fluorophenyl)amino]acetamido]benzoic Acid

A solution of 2-(N-bromoacetylamino)benzoic acid from Example 79 (8.00 g, 31.0 mmol), para-fluoroaniline (7.34 mL, 77.5 mmol) and DMF (80 mL) was heated to 75° C. for 8 h. The mixture was cooled, poured over $H_2O$ (1 L) and 5% KOH (300 mL) and washed with $CH_2Cl_2$ (3×300 mL). The aqueous layer was acidified to pH 2 with 2N HCl, cooled below room temperature and filtered. The filter cake was rinsed with water (60 mL) and dried under high vacuum at 45° C. to yield 7.98 g (89%) of the title compound as an off-white solid; $^1$H NMR (DMSO-$d_6$) δ 13.45 (broad s, 1H), 12.00 (s, 1H), 8.72 (d, J=8, 1H), 7.94 (dd, J=8, J=1.2, 1H), 7.59 (td, J=7.2, J=1.6, 1H), 7.13 (td, J=7.2, J=0.8, 1H), 6.95 (m, 2H), 6.58 (m, 2H), 6.47 (s, 1H), 3.82 (s, 2H); $^{13}$C NMR (DMSO-$d_6$) δ 170.73, 169.04, 154.95 (J=232.0), 144.78, 140.54, 134.15, 131.13, 122.69, 119.43, 116.00, 115.38 (J=21.9), 113.22 (J=7.6), 49.31.

Example 86

11-Chloro-7-fluoroquindoline

A slurried suspension of 2-[[N-(4-fluorophenyl) amino] acetamido]benzoic acid from Example 85 (7.50 g, 26.0 mmol) in polyphosphoric acid (330 g) was heated to 130° C. for 5.5 h with mechanical stirring. The mixture was diluted with ice-water (2 L) and placed in an ice-bath where the internal temperature was kept below 45° C. while the mixture was neutralized to pH 7 with a saturated KOH solution. The cold, precipitated solution was filtered, and the precipitate was washed with water (400 mL), and dried under high vacuum at 45° C. for several days to afford 7.14 g (109%) of crude 7-fluoro-11-quindolone as a green solid; $^1$H NMR (DMSO-$d_6$) δ 12.47 (s, 1H), 11.81 (s, 1H), 8.35 (d, J=8.0, 1H), 7.93 (dd, J=9.2, J=2.4, 1H), 7.69 (m, 2H), 7.52 (dd, J=8.8, J=4.4, 1), 7.35 (td, J=9.2, J=2.4, 1H), 7.31-7.28 (m, 1H); $^{13}$C NMR (DMSO-$d_6$) δ 167.69, 156.03 (J=233.5), 139.09, 135.28, 130.97, 128.60 (J=4.5), 125.24, 124.43, 122.69, 120.56, 117.78, 116.03 (J=25.8), 115.53 (J=10.7), 114.04 (J=9.1), 105.39 (J=24.3).

The crude 7-fluoro-11-quindolone obtained above (7.00 g) was refluxed in $POCl_3$ (100 mL) for 2.5 h. The mixture was cooled and slowly poured over ice (1L). The mixture was neutralized to pH 7 with a cold slurry of aqueous KOH while maintaining an internal temperature. below 45° C. with an external ice-bath. The total aqueous portion (1.4 L) was extracted with chloroform (5×500 mL). The combined organic extracts were washed with water (500 mL) and brine (500 mL), dried ($Na_2SO_4$), filtered and concentrated. The brown crude concentrate was adsorbed onto neutral alumina with acetone. Chromatography of the adsorbent over neutral alumina, eluting with ethyl acetate-hexane (1:5), afforded 2.71 g (39% overall) of the title compound as a yellow solid; $^1$H NMR (DMSO-$d_6$) δ 11.87 (s, 1H), 8.27-8.24 (m, 2H), 8.08 (dd, J=8.4, J=2.8, 1H), 7.78-7.71 (m, 2H), 7.61 (dd, J=8.8, J=4.4, 1H), 7.53 (td, J=9.2, J=2.8, 1H); $^{13}$C NMR (DMSO-$d_6$) δ 156.94 (J=236.5), 145.38 (J=4.6), 143.75, 140.50, 130.98, 129.33, 127.01, 126.65, 123.75, 122.16, 121.68 (J=9.1), 118.41, 118.14 (J=25.8), 113.21 (J=9.1), 107.09 (J=23.5).

Example 87

7-Fluoro-11-iodo-5-methylquindolinium Hydrochloride

In a large teflon lined steel bomb fitted with a stir bar was placed 11-chloro-7-fluoroquindoline from Example 86 (1.00 g, 3.69 mmol) and methyl iodide (8.00 mL, 129 mmol). The bomb was flushed with nitrogen, sealed, and heated to 150° C. for 24 h. The bomb was cooled, opened and the contents were transferred to a flask using chloroform to wash the inside of the bomb. The suspension was concentrated to a dry orange residue. The orange residue was suspended in chloroform, adsorbed onto Na$_2$CO$_3$ and chromatographed over basic alumina using 100% chloroform until starting material could not be detected by TLC. The column was eluted with 2% methanol in chloroform and the violet fractions were collected. After concentrating to a small volume (120 mL) the violet solution was acidified with ethereal 1M HCl to a bright yellow endpoint. The mixture was cooled below room temperature, filtered and dried under high vacuum at 45° C. for several days to yield 1.27 g (83%) of the title compound as a bright orange solid, which was contaminated with some 7-fluoro-11-chloro-5-methyquindolinium hydrochloride; $^1$H NMR (DMSO-$d_6$) δ 13.41 (s, 1H), 8.89 (d, J=8.8, 1H), 8.72 (dd, J=10.0, J=2.0, 1H), 8.65 (dd, J=8.4, J=1.2, 1H), 8.28 (ddd, J=8.8, J=7.2, J=1.2, 1H), 8.10 (t, J=7.8, 1H), 7.93-7.85 (m, 2H), 5.01 (s, 3H); $^{13}$C NMR (DMSO-$d_6$) δ 157.21 (J=237.3), 142.33, 138.09 (J=4.6), 135.90, 133.15, 132.38, 129.76 (C$_{11}$=chloro), 128.57, 124.60, 123.51, 123.18 (J=26.7), 118.84, 114.93 (J=8.5), 114.30 (J=10.8), 111.46 (J=26.7), 40.46; MS (LSIMS, m/z) 377 (M$^+$iodo, 100), 285 (M$^+$chloro, 17).

Example 88

2-[[N-(3-Fluorophenyl)amino]acetamido]benzoic acid

A solution of 2-(N-bromoacetylamino) benzoic acid from Example 79 (8.00 g, 31.0 mmol), meta-fluoroaniline (7.45 mL, 77.5 mmol) and DMF (80 mL) was heated to 80° C. for 8 h. The mixture was cooled, poured over H$_2$O (1 L) and 5% KOH (300 mL) and washed with CH$_2$Cl$_2$ (3×300 mL). The aqueous layer was acidified to pH 2 with 2N HCl, cooled below room temperature, and filtered. The filter cake was rinsed with cold water (100 mL) and dried under high vacuum at 45° C. to yield 7.00 g (78%) of the title compound as a grey solid; $^1$H NMR (DMSO-$d_6$) δ 13.5 (broad s, 1H), 11.94 (s, 1H), 8.70 (d, J=8.4, 1H), 7.94 (dd, J=7.8, J=1.4, 1H), 7.60 (td, J=8.0, J=1.4, 1H), 7.15-7.07 (m, 2H), 6.83 (broad s, 1H), 6.43-6.35 (m, 3H), 3.88 (s, 2H); $^{13}$C NMR (DMSO-$d_6$) δ 170.29, 169.12, 163.25 (J=240.3), 150.17 (J=10.6), 140.52, 134.18, 131.13, 130.43 (J=10.6), 122.73, 119.40, 115.98, 108.42, 103.09 (J=21.2), 98.97 (J=25), 48.48; MS (EI, m/z) 388 (M$^+$).

Example 89

11-Chloro-6-fluoroquindoline and 11-Chloro-8-fluoroquindoline

A slurried suspension of 2-[[N-(3-fluorophenyl) amino] acetamido]benzoic acid from Example 88 (6.75 g, 23.4 mmol) in polyphosphoric acid (420 g) was heated to 140° C. for 5 h with mechanical stirring. The mixture was poured over ice (1 L) and placed in an ice-bath where the internal temperature was kept below 45° C. while the mixture was neutralized to pH 7 with a saturated KOH solution (total volume 2 L). The cold, precipitated solution was filtered, and the precipitate was washed with water (250 mL) and dried under high vacuum at 45° C. for several days to afford 7.37 g (125%) of a mixture of 6-fluoro-11-quindolone and 8-fluoro-11-quindolone as a green solid; MS (FAB, m/z) 253 (MH$^+$).

The crude mixture obtained above (7.29 g) was refluxed in POCl$_3$ (60 mL) for 3 h. The mixture was cooled and slowly poured over ice (1 L). The mixture was neutralized to pH 7 with a cold slurry of aqueous KOH while maintaining an internal temperature below 45° C. with an external ice-bath. The total aqueous portion (1.3 L) was extracted with chloroform (5×400 mL). The combined organic extracts were washed with water (600 mL) and brine (600 mL), dried (Na$_2$SO$_4$) filtered and concentrated. The brown crude concentrate was adsorbed onto neutral alumina with acetone. Chromatography of the adsorbent over neutral alumina, eluting with ethyl acetate-hexane (1:5 gradiated to 1:4) and re-chromatography of mixed fractions in the same manner afforded 0.212 g (4% overall) of 11-chloro-6-fluoroquindoline and 1.39 g (22% overall) of 11-chloro-8-fluoro-quindoline as yellow solids.

Characterization of 11-chloro-6-fluoroquindoline: TLC R$_f$ 0.39 (ethyl acetate-hexane (1:2)); $^1$H NMR (DMSO-$d_6$) δ 12.09 (s, 1H), 8.28-8.25 (m, 2H), 7.79-7.71 (m, 2H), 7.65 (td, J=8.0, J=5.6, 1H), 7.44 (d, J=8.0, 1H), 7.10 (dd, J=10.4, J=8.0, 1H); $^{13}$C NMR (DMSO-$d_6$) δ 157.70 (J=254.0), 145.86 (J=8.5), 144.19, 143.68, 131.54 (J=9.2), 129.81, 129.41, 127.07, 126.71, 123.37, 122.08, 118.15, 109.26 (J=18.1), 108.20 (J=3.0), 106.10 (J=18.3); MS (FAB, m/z) 271 (MH$^+$).

Characterization of 11-chloro-8-fluoro-quindoline TLC R$_f$ 0.47 (ethyl acetate-hexane (1:2)); $^1$H NMR (DMSO-$d_6$) δ 11.95 (s, 1H), 8.34 (dd, J=8.4, J=5.6, 1H), 8.24 (m, 2H), 7.74 (ddd, J=17.6, J=6.8, J=1.6, 1H), 7.72 (ddd, J=17.6, J=6.8, J=1.6, 1H), 7.32 (dd, J=9.6, J=2.4, 1H), 7.14 (ddd, J=9.6, J=8.8, J=2.4, 1H); $^{13}$C NMR (DMSO-$d_6$) δ 163.80 (J=244.9), 145.35 and 145.21 and 145.08 (two carbons), 144.03, 130.44, 129.19, 127.05, 126.37, 123.51 (J=10.7), 123.35, 122.17, 118.06, 117.91, 108.41 (J=24.1), 98.57 (J=26.9); MS (FAB, m/z) 271 (MH$^+$).

Example 90

11-Chloro-6-fluoro-5-methylquindolinium Hydrochloride

To a solution of 11-chloro-6-fluoroquindoline from Example 89 (0.110 g, 3.89 mmol) and toluene (5 ml, freshly distilled) stirring under nitrogen was added methyl triflate (0.110 mL, 0.972 mmol). The mixture stirred for 24 h at room temperature and was diluted with diethyl ether (15 mL) and filtered. The orange filter cake was placed under high vacuum for 24 h. The orange residue was suspended in chloroform (400 mL), 5% KOH (150 mL) was added, and the resulting violet organic solution was separated. The violet organic solution was dried (Na$_2$SO$_4$) and filtered. The violet filtrate was acidified with ethereal 1M HCl to a bright yellow endpoint and adsorbed onto basic alumina. The adsorbent was chromatographed over basic alumina (eluting with chloroform-ethyl acetate gradient from 1:0 to 4:1 until the eluent was free of impurities by TLC then eluting with 2% methanol in chloroform). The violet fractions were collected and concentrated to a small volume (20 mL). The violet solution was acidified with ethereal 1M HCl to a bright yellow endpoint. The mixture was cooled below room temperature and filtered. The filter cake rinsed with diethyl ether (5 mL) and dried under high vacuum at 45° C. for several days to yield 0.109 g (98%) of the title compound as a bright orange solid. The title compound is poorly soluble in all common NMR solvents; $^1$H NMR (DMSO-$d_6$/CD$_3$OD 1:1 v/v) δ 8.64 (d, J=9.2, 1H), 8.63 (dd, J=8.0, J=1.2, 1H), 8.18 (ddd, J=9.2, J=6.6, J=1.2, 1H), 8.00 (ddd, J=8.4, J=6.2, J=1.2, 1H), 7.87 (td, J=8.4, J=5.2, 1H), 7.59 (dd, J=8.4, J=0.4, 1H), 7.22 (ddd, J=13.6, J=8.0, J=0.8, 1H), 4.98 (s, 3H).

Example 91

11-Chloro-8-fluoro-5-methylquindolinium Hydrochloride

To a solution of 11-chloro-8-fluoroquindoline from Example 89 (1.00 g, 3.69 mmol) in toluene (25 mL, freshly distilled) stirring under nitrogen was added methyl triflate (1.05 mL, 9.24 mmol). The mixture stirred for 24 h at room temperature and was diluted with diethyl ether (60 mL) and filtered. The orange filter cake was placed under high vacuum for 24 h. The orange residue was suspended in chloroform and adsorbed onto neutral alumina and chromatographed over basic alumina (eluting with chloroform-ethyl acetate gradient from 1:0 to 1:1 until the eluent was free of impurities by TLC then eluting with 3% methanol in chloroform). The violet fractions were collected and concentrated to a small volume (50 mL). The violet solution was acidified with ethereal 1M HCl to a bright yellow endpoint. The mixture was cooled below room temperature and filtered. The filter cake rinsed with diethyl ether (10 mL) and dried under high vacuum at 45° C. for several days to yield 0.949 g (90%) of the title compound as a bright orange solid. A portion of this material was further purified by HPLC. The title compound is poorly soluble in all common NMR solvents; $^1$H NMR (DMSO-$d_6$) δ 13.55 (s, 1H), 8.93 (dd, J=9.0, J=5.2, 1H), 8.87 (d, J=8.8, 1H), 8.68 (d, J=8.0, 1H), 8.27 (t, J=8.0, 1H), 8.11 (t, J=7.6, 1H), 7.64 (dd, J=9.0, J=2.2, 1H), 7.47 (J=9.2, J=2.2, 1H), 5.00 (s, 3H); MS (FAB, m/z) 285 (M$^+$).

Example 92

2-[[N-(2-Fluorophenyl)amino]acetamido]benzoic acid

A solution of 2-(N-bromoacetylamino)benzoic acid from Example 79 (8.00 g, 31.0 mmol), ortho-fluoroaniline (7.48 mL, 77.5 mmol) and DMF (80 mL) was heated to 75° C. for 8 h. The mixture was cooled, poured over H$_2$O (1 L) and 5% KOH (300 mL) and washed with CH$_2$Cl$_2$ (3×300 mL). The aqueous layer was acidified to pH 2 with 2N HCl, cooled below room temperature and filtered. The filter cake was rinsed with water (60 mL) and dried under high vacuum at 45° C. to yield 7.62 g (85%) of the title compound as an off-white solid; $^1$H NMR (DMSO-$d_6$) δ 13.54 (broad s, 1H), 12.01 (s, 1H), 8.72 (d, J=8.4, 1H), 7.93 (dd, J=8, J=1.4, 1H), 7.59 (td, J=7.2, J=1.6, 1H), 7.13 (t, J=7.6, 1H), 7.05 (dd, J=11.6, J=8.0, 1H), 6.94 (t, J=7.6, 1H), 6.58 (m, 2H), 6.37 (broad s, 1H), 3.90 (d, J=5.6, 2H); $^{13}$C NMR (DMSO-$d_6$) δ 170.30, 169.19, 151.02 (J=238.1), 140.56, 136.00 (J=11.3), 134.20, 131.12, 124.77 (J=3.1), 122.71, 119.35, 116.80 (J=6.8), 114.52 (J=18.2), 111.81 (J=3.1), 48.23.

Example 93

11-Chloro-9-fluoroquindoline

A slurried suspension of 2-[[N-(2-fluorophenyl)amino]acetamido]benzoic acid from Example 92 (7.50 g, 26.0 mmol) in polyphosphoric acid (330 g) was heated to 130° C. for 5.5 h with mechanical stirring. The mixture was diluted with ice-water (2 L) and placed in an ice-bath where the internal temperature was kept below 45° C. while the mixture was neutralized to pH 7 with a saturated KOH solution. The cold, precipitated solution was filtered, and the precipitate was rinsed with water (400 mL) and dried under high vacuum at 45° C. for several days to afford 10.82 g (165%) of crude 9-fluoro-11-quindolone as a brown solid; $^1$H NMR (DMSO-$d_6$) δ 12.57 (s, 1H), 12.20 (s, 1H), 8.38 (dd, J=8.0, J=1.2, 1H), 8.02 (dd, J=7.6, J=0.8, 1H), 7.75-7.67 (m, 2H), 7.35-7.28 (m, 2H), 7.17 (td, J=8.0, J=4.4, 1H); $^{13}$C NMR (DMSO-$d_6$) δ 167.70, 149.42 (J=245.7), 139.21, 131.02, 129.18 (J=3.8), 126.98 (J=14.4), 125.27, 123.72, 123.02, 120.71, 119.73 (J=6.0), 119.22 (J=5.3), 117.85, 116.94 (J=3.8), 112.96 (J=16.0).

The crude 7-fluoro-11-quindolone obtained above (10.5 g) was refluxed in POCl$_3$ (100 mL) for 2.5 h. The mixture was cooled and slowly poured over ice (1L). The mixture was neutralized to pH 7 with a cold slurry of aqueous KOH while maintaining an internal temperature below 45° C. with an external ice-bath. The total aqueous portion (1.4 L) was extracted with chloroform (5×500 mL). The combined organic extracts were washed with water (500 mL) and brine (500 mL), dried (NaSO$_4$), filtered and concentrated. The brown crude concentrate product was adsorbed onto neutral alumina with acetone. Chromatography of the adsorbent over neutral alumina, eluting with ethyl acetate-hexane (1:5), afforded 3.70 g (45% overall) of the title compound as a yellow solid; $^1$H NMR (DMSO-$d_6$) δ 12.26 (s, 1H), 8.28 (m, 2H), 8.18 (d, J=7.6, 1H), 7.80-7.72 (m, 2H), 7.55 (dd, J=11.2, J=8.4, 1H), 7.31 (td, J=7.8, J=4.4, 1H); $^{13}$C NMR (DMSO-$d_6$) δ 148.76 (J=244.9), 145.59, 144.13, 131.72 (J=13.8), 130.51, 130.30, 127.23, 126.66, 125.03 (J=5.3), 123.90, 122.28, 120.77 (J=5.3), 119.27, 117.58 (J=3.1), 115.59 (J=16.7); MS (LSIMS, m/z) 270 (M$^+$).

Example 94

9-Fluoro-11-iodo-5-methylquindolinium Hydrochloride

In a large teflon lined steel bomb fitted with a stir bar was placed 11-chloro-9-fluoroquindoline from Example 93 (1.00 g, 3.69 mmol) and methyl iodide (8.00 mL, 129 mmol). The bomb was flushed with nitrogen, sealed, and heated to 150° C. for 24 h. The bomb was cooled, opened and the contents were transferred to a flask using chloroform to wash the inside of the bomb. The suspension was concentrated to a dry orange residue. The orange residue was suspended in chloroform, adsorbed onto Na$_2$CO$_3$ and chromatographed over basic alumina using 100% chloroform until starting material could not be detected by TLC. The column was eluted with 2% methanol in chloroformand the violet fractions were collected and concentrated to a small volume (100 mL). The violet solution was acidified with ethereal 1M HCl to a bright yellow endpoint, cooled below room temperature, filtered and dried under high vacuum at 45° C. for several days to yield 0.844 g (55%) of a mixture of the title compound, contaminated with some 11-fluoro-9-chloro-5-methylquindolinium hydrochloride, as a bright orange solid; $^1$H NMR (DMSO-$d_6$) δ 13.74 (broad s, 1H), 8.88 (d, J=8.8, 1H), 8.67 (t, J=8.0, J=2.0, 2H), 8.32-8.26 (m, 1H), 8.10 (t, J=8.8, J=7.6, 1H), 7.87 (dd, J =10.8, J=8.0, 1H), 7.52 (td, J=8.0, J=4.8, 1H), 5.03 (s, 3H); $^{13}$C NMR (DMSO-$d_6$) δ 148.68 (J=248.0), 138.61 (J=3.8), 136.09, 134.1 (J=15), 133.35, 132.28, 130.50 ($C_{11}$=chloro) , 128.74, 124.72, 123.76, 122.66 (J=3.8), 122.39 (J=5.3), 118.92 (J=15.3), 118.94, 117.87 (J=5.3), 95.2 ($C_{11}$=iodo), 40.67; MS (LSIMS, m/z) 377 (M$^+$iodo, 100), 285 (M$^+$chloro, 20).

Example 95

2-[[N-(4-Phenylphenyl)amino]acetamido]benzoic acid

A solution of 2-(N-bromoacetylamino)benzoic acid from Example 79 (8.00 g, 31.0 mmol), para-aminobiphenyl (13.12 g, 77.5 mmol) and DMF (80 mL) was heated to 80° C. for 8 h. The mixture was cooled, poured over $H_2O$ (1 L) and 5% KOH (300 mL) and washed with $CH_2Cl_2$ (3×300 mL). The aqueous layer was acidified to pH 2 with 2N HCl, cooled below room temperature and filtered. The filter cake was rinsed with cold water (100 mL) and dried under high vacuum at 45° C. The resulting air-sensitive material was triturated with ethyl acetate (100 mL), filtered, and rinsed with ethyl acetate (2×25 mL) to yield, after drying, 8.18 g (76%) of the title compound as a tan solid; $^1$H NMR (DMSO-$d_6$) δ 13.4 (broad s, 1H), 12.05 (s, 1H), 8.75 (d, J=8.4, 1H), 7.95 (dd, J=7.4, J=1.2, 1H), 7.60 (td, J=7.2, J=1.2, 1H), 7.54 (d, J=7.6, 2H), 7.45 (d, J=8.8, 2H), 7.37 (t, J=7.6, 2H), 7.22 (t, J=7.6, 1H), 7.13 (t, J=7.6, 1H), 6.69 (d, J=8.4, 2H), 6.7 (broad s, 1H), 3.90 (s, 2H); $^{13}$C NMR (DMSO-$d_6$) a 170.74, 169.12, 147.71, 140.60, 140.36, 134.20, 131.14, 128.87, 128.74, 127.28, 125.96, 125.55, 122.69, 119.40, 115.97, 112.85, 48.87; MS (EI, m/z) 328 (M-$H_2O^+$).

Example 96

11-Chloro-7-phenylquindoline

A slurried suspension of 2-[[N-(4-phenylphenyl) amino]acetamido]-benzoic acid from Example 95 (8.00 g, 23.1 mmol) in polyphosphoric acid (480 g) was heated to 140° C. for 5 h with mechanical stirring. The mixture was partially cooled and poured over ice. The reaction mixture was placed in an ice-bath where the internal temperature was kept below 45° C. while the mixture was neutralized to pH 7 with a saturated KOH solution to a total volume of 2 L. The cold, precipitated solution was filtered, and the precipitate was rinsed with water (250 mL) and dried under high vacuum at 45° C. for several days to afford 10.54 g (147%) of crude 7-phenyl-11-quindolone as a green solid: MS (FAB, m/z) 311 (MH$^+$).

The crude 7-phenyl-11-quindolone obtained above (8.43 g) was refluxed in POCl$_3$ (80 mL) for 3 h. The mixture was cooled and slowly poured over ice (1L). The mixture was neutralized to pH 7 with a cold slurry of aqueous KOH while maintaining an internal temperature below 45° C. with an external ice-bath. The total aqueous portion (1.7 L) was extracted with chloroform (5×600 mL). The combined organic extracts were washed with water (600 mL) and brine (600 mL), dried (Na$_2$SO$_4$), filtered and concentrated. The crude concentrate was adsorbed onto neutral alumina with acetone. Chromatography of the adsorbent over neutral alumina, eluting with ethyl acetate-hexane (1:5 gradiated to 1:3), afforded 1.61 g (25% overall) of the title compound as a reddish solid: $^1$H NMR (DMSO-$d_6$) δ 11.92 (s, 1H), 8.58 (d, J=1.2, 1H), 8.30-8.27 (m, 2H), 7.98 (dd, J=8.4, J=1.6, 1H), 7.82-7.69 (m, 5H), 7.50 (t, J=7.8, 2H), 7.37 (t, J=7.2, 1H); $^{13}$C NMR (DMSO-$d_6$) δ 146.50, 144.31, 144.02, 140.81, 133.08, 131.00, 129.87, 129.73, 129.45, 127.38, 127.31, 127.19, 126.89, 124.15, 122.61, 122.30, 119.74, 118.64, 112.93; MS (FAB, m/z) 329 (MH$^+$).

Example 97

11-Chloro-7-phenyl-5-methylquindolinium Hydrochloride

To a solution of 11-chloro-7-phenylquindoline from Example 96 (0.250 g, 0.760 mmol) in toluene (10 ml, freshly distilled) stirring under nitrogen was added methyl triflate (0.130 mL, 0.114 mmol). The mixture stirred for 2 h at room temperature and was diluted with diethyl ether (40 mL) and filtered. The orange filter cake was placed under high vacuum for 24 h. The orange residue was suspended in chloroform and adsorbed onto neutral alumina. The adsorbent was chromatographed over basic alumina (eluting with chloroform until the eluant was free of impurities by TLC, then eluting with 0.2% methanol in chloroform). The violet fractions were collected and concentrated to a small volume (50 mL). The violet solution was acidified with ethereal 1M HCl to a bright yellow endpoint. The mixture was cooled below room temperature and filtered. The filter cake was dried under high vacuum to yield 0.121 g (42%) of the title compound as a red solid; $^1$H NMR (DMSO-$d_6$) δ 13.62 (s, 1H), 8.90-8.86 (m, 2H), 8.60 (d, J=8.4, 1H), 8.27-8.20 (m, 2H), 8.06 (t, J=7.6, 1H), 7.92-7.88 (m, 3H), 7.55 (t, J=7.6, 2H), 7.44 (t, J=7.6, 1H), 5.11 (s, 3H); $^{13}$C NMR (DMSO-$d_6$) δ 145.21, 139.37, 138.58, 135.80, 134.31, 133.73, 132.84, 132.04, 129.10, 129.00, 128.39, 127.55, 127.28, 126.96, 126.62, 124.55, 123.80, 123.37, 118.82, 114.93, 113.91, 40.65; MS (FAB, m/z) 343 (M$^+$).

Example 98

3-Chloro-2-[N-(phenylamino)acetamido]benzoic acid

A solution of 3-chloro-2-(bromoacetamido) benzoic acid from Example 39 (4.6 g, 15.7 mmol), aniline (3.58 mL, 39.3 mmol) and DMF (45 mL) was heated to 80° C. for 8 h. The mixture was cooled, poured over $H_2O$ (400 mL) and 5% KOH (125 mL) and washed with $CH_2Cl_2$ (3×125 mL). The aqueous layer was acidified to pH 2 with 2N HCl, cooled below room temperature and filtered. The filter cake was rinsed with cold water (50 mL) and dried under high vacuum at 45° C. to yield 3.19 g (67%) of the title compound as a tan solid; $^1$H NMR (DMSO-$d_6$) δ 13.1 (broad s, 1H), 9.85 (s, 1H), 7.74 (d, J=7.6, 1H), 7.71 (d, J=8.0, 1H), 7.35 (t, J=7.6, 1H), 7.10 (t, J=7.6, 2H), 6.65-6.58 (m, 3H), 6.1 (broad s, 1H), 3.82 (s, 2H); $^{13}$C NMR (DMSO-$d_6$) δ 169.62, 166.77, 148.33, 133.87, 132.70, 131.53, 130.93, 128.90, 128.82, 127.21, 116.59, 112.57, 47.16; MS (LSIMS, m/z) 305 (M+H$^+$).

Example 99

4,11-Dichloroquindoline

A slurried suspension of 3-chloro-2-[N-(phenylamino) acetamido]benzoic acid from Example 98 (3.10 g, 10.2 mmol) in polyphosphoric acid (180 g) was heated to 140° C. for 5 h with mechanical stirring. The mixture was partially cooled and poured over ice-water (400 mL). The mixture was placed in an ice-bath where the internal temperature was kept below 45° C. while the mixture was neutralized to pH 7 with a saturated KOH solution. The cold, precipitated solution was filtered. The precipitate was rinsed with water (50 mL) and dried under high vacuum at 45° C. for several days to afford 2.72 g (99%) of 4-chloro-11-quindolone as a brown solid; $^1$H NMR (DMSO-$d_6$) δ 11.88 (s, 1H), 11.72 (s, 1H), 8.69 (d, J=8.4, 1H), 8.37 (dd, J=8.0, 1.6, 1H), 7.87 (J=7.4, J=1.4, 1H), 7.53-7.45 (m, 2H), 7.31 (t, J=7.8, 1H), 7.20 (ddd, J=8.4, J=6.8, J=1.2, 1H); $^{13}$C NMR (DMSO-$d_6$) δ 166.97, 138.75, 135.60, 131.10, 128.84, 127.62, 124.60, 124.52, 123.26, 122.69, 121.12, 120.78, 118.89, 116.14, 112.41; MS (LSIMS, m/z) 269 (MH$^+$).

The crude 4-chloro-11-quindolone obtained above (2.70 g) was refluxed in POCl$_3$ (35 mL) for 3 h. The mixture was cooled and slowly poured over ice (500 mL). The mixture was neutralized to pH 7 with a cold slurry of aqueous KOH while maintaining an internal temperature below 45° C. with an external ice-bath. The total aqueous portion was extracted with chloroform (4×300 mL). The combined organic extracts were washed with water (300 mL) and brine (300 mL), dried ($Na_2SO_4$), filtered and concentrated. The crude was adsorbed onto neutral alumina with acetone. Chromatography of the adsorbent over neutral alumina, eluting with ethyl acetate-hexane (1:5 gradiated to 1:4), afforded 0.186 g (6% overall) of the title compound as a yellow solid; $^1H$ NMR (DMSO-$d_6$) δ 12.01 (s, 1H), 8.38 (d, J=8.4, 1H), 8.27 (dd, J=8.4, J=1.2, 1H), 7.95 (dd, J=7.6, J=1.2, 1H), 7.73-7.64 (m, 3H), 7.38 (t, J=7.2, 1H); $^{13}C$ NMR (DMSO-$d_6$) δ 146.16, 144.45, 139.52, 132.59, 130.87, 130.46, 127.02, 126.15, 124.96, 121.94, 121.75, 121.06, 120.56, 118.50, 112.22; MS (FAB, m/z) 329 (M-1).

7. EXAMPLE: HYPOGLYCEMIC ACTIVITY OF THE CRYPTOLEPINE ANALOGS

7.1 IN VIVO ACTIVITY OF THE CRYPTOLEPINE ANALOGS

Representative cryptolepine analogs were tested in the in vivo mouse model described below.

7.1.1 Protocol for In vivo Experiments

Genetically altered obese diabetic mice (designated C57BL/Ks-db/db) were purchased from The Jackson Laboratory (Bar Harbor, Me., USA), and served as experimental animals. Male animals between the ages of 8–9 weeks were employed in the studies described here. Animals were housed (4 mice/cage) under standard laboratory conditions at 22° C. and 50% relative humidity, and were maintained on a diet of Purina rodent chow and water ad libitum. Prior to treatment, blood was collected from the tail vein of each animal. Mice that had plasma glucose levels between 350 and 600 mg/dL were used. Each treatment group consisted of eight mice that were distributed so that the mean glucose levels were equivalent in each group at the start of the study. Diabetic C57BL/Ks-db/db mice were dosed orally by gavage once with either vehicle, the experimental compound administered at 100 mg (unless otherwise noted), or metformin [250 mg (1510 μmol)kg/day]. Compounds were delivered in a liquid vehicle containing 0.25% (w/v) carboxymethylcellulose, 1% (v/v) Tween™ 60, and up to 10% (v/v) dimethyl sulfoxide (DMSO) in a volume of 10 ml/kg. Blood was sampled from the tail vein three hours post-dosing, and analyzed for plasma glucose levels. Individual body weights and mean food consumption (each cage) were also measured after 24 h.

The cryptolepine compounds tested for hypoglycemic activity were prepared as described above in Section 6.2 above. Metformin (1,1-dimethylbiguanide) was purchased from Sigma Chemical Co. (St. Louis, Mo., USA; catalog# D-5035).

Plasma glucose levels were determined colorimetrically using glucose oxidase (Sigma Chemical Co.; Sigma catalog# 315). Significant differences between groups (comparing compound-treated to vehicle-treated) were evaluated using analysis of variance and Fisher's post-hoc test.

7.1.2 Results

The following test compounds were evaluated in diabetic C57BL/Ks-db/db animals for the ability to lower blood glucose:

2-Fluoro-5-methylquindolinium hydrochloride (Compound A);

7-Bromo-8-chloro-5-methylquindolinium hydrochloride (Compound B);

5-Ethylquindolinium hydrochloride (Compound C);

5-Butylquindolinium hydrochloride (Compound D);

7-Fluoro-11-iodo-5-methylquindolinium hydrochloride (Compound E);

9-Fluoro-11-iodo-5-methylquindolinium hydrochloride (Compound F);

5-(4'-Fluorobenzyl)quindolinium hydrochloride (Compound G);

2-Fluoro-5-methyl-11-(phenylamino)quindolinium hydrochloride (Compound H); and

2-Fluoro-5-methyl-11-(phenoxy)quindolinium hydrochloride (Compound I).

The test compounds were evaluated in a series of experiments which are summarized in Table 1 below.

Single doses of Compound A, Compound B, Compound C, Compound E, Compound G, Compound H, and Compound I (100 mg/kg) given to diabetic C57Bl/Ks db/db mice resulted in statistically significant reductions in plasma glucose relative to vehicle controls either 3 or 24 h after oral administration. Three hours after dosing, mean glucose levels for the active experimental compounds declined 59–196 mg/dL, depending on the sample, from the baseline values.

By comparison, the known hypoglycemic agent metformin, given at 250 mg/kg, caused a reduction in plasma glucose levels of 136–225 mg/dL.

TABLE 1

Effects of Cryptolepine Analogs on Blood Glucose in Diabetic db/db mice

| Exp. No. | Treatment | Change in Glucose (mg/dL) 3 h | P Value* | Change in Glucose (mg/dL) 24 h | P Value* |
|---|---|---|---|---|---|
| 1 | Metformin | −154 | 0.034 | −37 | NS** |
| 2 | Metformin | −182 | 0.0015 | 8 | NS |
|   | Compound A | −196 | 0.0007 | −159 | 0.0006 |
|   | Compound B | −152 | 0.011 | −87 | 0.037 |
|   | Compound C | −107 | 0.20 | −122 | 0.0213 |
|   | Compound D | −156 | 0.090 | −10 | NS |
| 3 | Metformin | −136 | 0.02 | −55 | 0.093 |
|   | Compound E | −128 | 0.028 | −51 | NS |
|   | Compound F | 77 | NS | −128 | 0.163 |
| 4 | Metformin | −225 | <0.0001 | −50 | 0.061 |
|   | Compound G | −161 | <0.0001 | −43 | 0.091 |
| 5 | Metformin | −195 | <0.0001 | 38 | NS |
|   | Compound H | −59 | 0.086 | −61 | 0.017 |
|   | Compound I | −67 | 0.050 | −43 | 0.045 |

*Statistical significance evaluated using analysis of variance and Fisher's post-hoc test.
**NS — not significant at p < 0.05 level Body weights and food consumption were adversely affected in animals treated with Compound A, Compound C, Compound E, Compound F, Compound G, Compound H, and Compound I during the test period (Table 2).

Although Compound D did not result in substantial reductions in plasma glucose in the 3–24 h time period under the conditions of the in vivo experiment, as will be described below, this compound does result in increased glucose transport in an in vitro, art-recognized system. This in vitro system represents an important mode of action for glucose utilization and disposal in mammals. Additionally, it would be recognized by those skilled in the art that under the conditions in which this compound was evaluated in vivo, i.e., a single dose, differences in pharmacokinetics, absorption, or pharmacology could explain the reduced activity compared to the "active" compounds.

TABLE 2

Effects of Cryptolepine Analogs on Body Weights and Food Consumption in Diabetic db/db Mice

| Exp. No. | Treatment | Body weight (g/mouse) (mean) 0 h | Body weight (g/mouse) (mean) 24 hr | Food Intake (g/mouse) 0–24 h |
|---|---|---|---|---|
| 1 | Vehicle | 45.6 | 45.7 | 5.5 |
|   | Metformin | 42.9 | 42.8 | 4.7 |
| 2 | Vehicle | 43.0 | 43.0 | 4.9 |
|   | Metformin | 44.5 | 44.7 | 4.6 |
|   | Compound A | 43.8 | 41.9 | 0.5 |
|   | Compound B | 45.7 | 45.5 | 2.8 |
|   | Compound C | 44.6 | 43.3 | 1.3 |
|   | Compound D | 45.7 | 45.8 | 2.6 |
| 3 | Vehicle | 43.9 | 43.3 | 3.5 |
|   | Metformin | 43.3 | 43.1 | 3.4 |
|   | Compound E | 42.2 | 41.8 | 2.7 |
|   | Compound F | 43.4 | 41.4 | 0.7 |
| 4 | Vehicle | 40.5 | 39.9 | 6.0 |
|   | Metformin | 39.9 | 39.6 | 4.8 |
|   | Compound G | 40.2 | 39.0 | 3.1 |
| 5 | Vehicle | 45.1 | 44.9 | 6.4 |
|   | Metformin | 44.7 | 44.5 | 4.8 |
|   | Compound H | 44.8 | 44.2 | 3.2 |
|   | Compound I | 46.6 | 45.2 | 1.6 |

7.2 IN VITRO ACTIVITY OF THE CRYPTOLEPINE ANALOGS

The following examples illustrate the ability of the cryptolepine analogs described herein to directly stimulate glucose transport in 3T3-L1 adipocytes, an art recognized in vitro system that represents an important mode of action for glucose utilization and disposal in mammals. Metformin, a drug that enhances glucose disposal and one that is currently used to treat NIDDM, exhibits significant stimulatory activity in this model system.

7.2.1 Protocol for In vitro Experiments

Cell culture and 2-deoxy-D-glucose uptake in differentiated 3T3-L1 adipocytes: Murine 3T3-L1 preadipocytes (American Type Culture Collection CL 173) were maintained in Dulbecco's modified Eagles medium (DMEM) containing 10% (v/v) supplemented calf serum, antibiotics, and 25 mM glucose. Cells were seeded in 24-well cluster plates (10,000 cells/well), grown to confluence (typically 5 days), and induced to differentiate 2 days post-confluence (day 0) according to the standard protocol of Frost and Lane [Frost, S. and Lane, M.D. *J. Biol. Chem.* 1985, 260, 2646–2652]. Following differentiation, adipocytes were maintained in DMEM containing 10% fetal bovine serum, and provided with fresh medium every 2–3 days. Adipocytes employed in this study were used on days 7–10 post-differentiation. On the day of the experiment, adipocytes were washed with phosphate- buffered saline and switched to serum-free DMEM medium. Adipocytes were treated (in triplicate) for 18 hr with a test compound, i.e., a cryptolepine analog (at 1, 3, 10, and 30 μM final concentrations) or metformin.

The following compounds were tested in the in vitro assay:

2-Fluoro-5-methylquindolinium hydrochloride (Compound A);

7-Bromo-8-chloro-5-methylquindolinium hydrochloride (Compound B);

5-Ethylquindolinium hydrochloride (Compound C);

5-Butylquindolinium hydrochloride (Compound D);

7-Fluoro-11-iodo-5-methylquindolinium hydrochloride (Compound E);

9-Fluoro-11-iodo-5-methylquindolinium hydrochloride (Compound F);

5-(4'-Fluorobenzyl)quindolinium hydrochloride (Compound G);

2-Fluoro-5-methyl-11-(phenylamino)quindolinium hydrochloride (Compound H);

2-Fluoro-5-methyl-11-(phenoxy)quindolinium hydrochloride (Compound I);

5-Methylquindoline (Compound J);

5-Methylquindolinium hydrochloride (Compound K);

5-Benzylquindolinium hydrochloride (Compound L);

5,10-Dibenzylquindolinium chloride (Compound M);

5,10 -Dimethyl-11-(methoxycarbonyl)quindolinium iodide (Compound N);

5-Methyl-11-(methoxycarbonyl)quindolinium hydroiodide (Compound O);

6-Methoxy-5-methylquindolinium hydrochloride (Compound P);

5-methyl-11-chloroquindolinium hydrochloride (Compound Q);

2-Fluoro-5-methyl-11-chloroquindolinium hydrochloride (Compound R);

11-Chloro-5-methylbenzofuro[3, 2- b]quinoline trifluoromethanesulfonate (Compound S);

2-Fluoro-5-methyl-11-phenylquindolinium hydrochloride (Compound T);

11-Chloro-5-methylbenzothieno[3, 2- b]quinolinium trifluoromethanesulfonate (Compound U);

11-(4-Chlorophenylthio)-5-methylbenzofuro[3, 2-b] quinolinium chloride (Compound V);

2-Fluoro-5-methyl-11-[(4-chlorophenyl) thio] quindolinium hydrochloride (Compound W);

11-Chloro-6-fluoro-5-methylquindolinium hydrochloride (Compound X);

2-Chloro-5-methyl-11-chloroquindolinium hydrochloride (Compound Y);

11-Chloro-5-methylindeno[1, 2-b]quinolinium trifluoromethanesulfonate (Compound Z);

11-[(4-Chlorophenyl)thio]-5-methylindeno[1,2-b] quinolinium chloride (Compound AA);

1-Chloro-5-methyl-11-chloroquindolinium hydrochloride (Compound AB);

11-Chloro-8-fluoro-5-methylquindolinium hydrochloride (Compound AC);

11-Chloro-7-phenyl-5-methylquindolinium hydrochloride (Compound AD);

5-Methylquindolinium hydroiodide (Compound AE); and 4,11-Dichloroquindolinium hydrochloride (Compound AF).

The compounds were tested at 1, 3, 10 and 30 mM (triplicate incubations).

Concentrated stock solutions of the cryptolepine analogs were freshly prepared in dimethyl sulfoxide (DMSO) and diluted into culture medium. The final concentration of DMSO was 0.2% (v/v) which was also included in basal conditions. Metformin was dissolved directly into culture medium and further diluted into the same medium. Following overnight (18 hr) treatment, the culture medium was aspirated and the monolayers washed with Krebs-Ringer Hepes buffer. To assess the effects of the compounds on glucose transport, 2-deoxy-D-glucose uptake (a non-metabolizable analog of glucose) was measured in the absence of insulin stimulation. Glucose transport assays were initiated by the addition of 2-deoxy-D-[$^3$H]glucose (0.5 mCi/mL; 100 mM final concentrations) to each well followed by incubation for 10 min at 22° C. Assays were terminated by aspirating the media and rapidly washing the monolayer two times with ice-cold phosphate-buffered saline solution. Cell monolayers were solubilized in 0.1N NaOH, transferred to scintillation vials, and radioactivity determined by liquid scintillation counting. All data were corrected for non-specific hexose uptake determined in parallel samples treated for 5 minutes with 200 mM cytochalasin B.

7.2.2 Results

The ability of the cryptolepine analogs to significantly stimulate glucose transport in 3T3-L1 adipocytes is shown in Table 3. The magnitude of stimulation ranged from approximately 120% of basal to approximately 780%. Under these experimental conditions, 3 mM metformin (the maximally effective concentration) stimulates glucose transport by approximately 350%. As would be recognized by those skilled in the art, these data indicate that the cryptolepine analogs listed in Table 3 directly stimulate glucose transport in vitro, an effect that is consistent with the enhancement of glucose disposal and the ability to lower blood glucose in vivo.

TABLE 3

Stimulatory Effects of Cryptolepine Analogs on 2-deoxy-D-glucose Uptake in 3T3-L1 Adipocytes

| Compound | Concentration (mM) | Stimulatory Activity (% Basal) |
|---|---|---|
| Compound J | 30 | 154 |
| Compound AE | 30 | 287 |
| Compound K | 30 | 175 |
| Compound A | 30 | 213 |
| Compound B | 3 | 127 |
| Compound C | 30 | 406 |
| Compound D | 3 | 378 |
| Compound L | 10 | 781 |
| Compound F | 10 | 254 |
| Compound M | 3 | 262 |
| Compound N | 30 | 260 |
| Compound O | 30 | 371 |
| Compound G | 30 | 278 |
| Compound P | 30 | 518 |
| Compound R | 10 | 177 |
| Compound H | 3 | 325 |
| Compound I | 10 | 146 |
| Compound T | 3 | 281 |
| Compound V | 10 | 142 |
| Compound W | 10 | 154 |
| Compound X | 10 | 385 |
| Compound Y | 30 | 215 |
| Compound Z | 30 | 297 |
| Compound AB | 30 | 352 |
| Compound AF | 10 | 232 |
| Compound AC | 10 | 159 |
| Compound AD | 10 | 146 |

Values shown for stimulatory activity are expressed as a percent of basal glucose transport (typically 50 nmoles 2-deoxyglucose/10 minutes/well), and represent the maximum stimulation observed along with the corresponding concentration). All compounds listed above demonstrated significant stimulation of glucose transport (P<0.05 or better) as judged using a Student's t-test (one-tailed, independent).

In addition to the compounds listed in Table 3, the following compounds did not demonstrate statistically significant glucose transport stimulatory activity: Compound E, Compound Q, Compound S, Compound U, and Compound AA.

What is claimed is:

1. A compound having the formula III

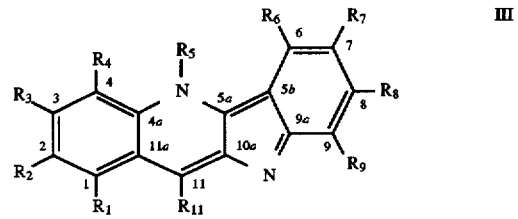

wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_5$ is selected from the group consisting of $C_1$–$C_{10}$ alkyl, $C_2$–$C_{10}$ alkenyl, and $C_2$–$C_{10}$ alkynyl groups; said $C_1$–$C_{10}$ alkyl, $C_2$–$C_{10}$ alkenyl and $C_2$–$C_{10}$ alkynyl groups being optionally substituted with one or more groups consisting of halogen, amino, methylamino, dimethylamino, trimethylamino, hydroxy, methoxy, ethoxy, phenoxy, and $C_1$–$C_6$ alkyl;

$R_6$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl;

$R_7$ is selected from the group consisting of hydrogen, halogen, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl; and with the proviso that $NHR_{13}$ is not $NH_2$;

$R_{11}$ is selected from the group consisting of hydrogen, halogen, azide, cyano, $OR_{13}$, $NHR_{13}$, $SR_{13}$, phenyl, optionally substituted phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, or phenyl; said $C_1$–$C_{10}$ alkyl group, $C_2$–$C_{10}$ alkenyl group or a $C_2$–$C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1$–$C_6$ alkyl or phenyl; with the proviso that $NHR_{13}$ is not $NH_2$ or $NH(C_1$–$C_6$ alkyl); and with the further proviso that $OR_{13}$ is not —O—($C_1$–$C_6$)alkyl;

each $R_{12}$ is selected from the group consisting of hydrogen and a $C_1$–$C_6$ alkyl group; said $C_1$–$C_6$ alkyl group being optionally substituted with one or more groups selected from the group consisting of phenyl and $C_1$–$C_3$ alkyl;

$R_{13}$ is selected from the group consisting of hydrogen, phenyl and a $C_1$–$C_6$ alkyl group; said $C_1$–$C_6$ alkyl group being optionally substituted with one or more groups selected from the group consisting of phenyl and $C_1$–$C_3$ alkyl; said phenyl being optionally substituted with one or more groups selected from the group consisting of halogen, methoxy, ethoxy, hydroxy, amino, and $C_1$–$C_6$ alkyl; and with the proviso that when $R_1$–$R_4$, $R_6$–$R_9$ and $R_{11}$ are H, $R_5$ is not $CH_3$ or $CH_2CH_3$.

2. A compound having the formula IV

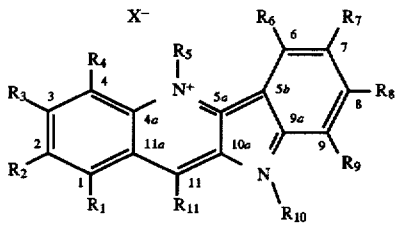

wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_5$ is selected from the group consisting of $C_1$–$C_{10}$ alkyl, $C_2$–$C_{10}$ alkenyl and $C_2$–$C_{10}$ alkynyl groups; said $C_1$–$C_{10}$ alkyl, $C_2$–$C_{10}$ alkenyl and $C_2$–$C_{10}$ alkynyl groups being optionally substituted with one or more groups consisting of halogen, amino, methylamino, dimethylamino, trimethylamino, hydroxy, methoxy, ethoxy, phenoxy, and $C_1$–$C_6$ alkyl;

$R_6$, $R_8$ and $R_9$ are independently selected from the group consisting of hydrogen, halogen, nitro, $SO_3H$, $COOR_{12}$, $OR_{13}$, $NHR_{13}$, $SR_{13}$, phenyl, optionally substituted phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of $C_1$–$C_6$ alkyl and phenyl;

$R_7$ is selected from the group consisting of hydrogen, halogen, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl; and with the proviso that $NHR_{13}$ is not $NH_2$;

$R_{10}$ is selected from the group consisting of hydrogen, acetyl, $C_1$–$C_{10}$ alkyl group, $C_2$–$C_{10}$ alkenyl group, $C_2$–$C_{10}$ alkynyl group and phenylmethyl; said $C_1$–$C_{10}$ alkyl, $C_2$–$C_{10}$ alkenyl and $C_2$–$C_{10}$ alkynyl groups being optionally substituted with one or more groups selected from the group consisting of halogen, amino, methylamino, dimethylamino, trimethylamino, hydroxy, methoxy, ethoxy, phenoxy, phenyl and $C_1$–$C_6$ alkyl; said phenylmethyl being optionally substituted with one or more groups selected from the group consisting of halogen, amino, dimethylamino, hydroxy, methoxy, ethoxy, $C_1$–$C_6$ alkyl, isopropyl, isobutyl, tert-butyl, and phenyl;

$R_{11}$ is selected from the group consisting of hydrogen, halogen, azide, cyano, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1$–$C_6$ alkyl and phenyl; with the proviso that $NHR_{13}$ is not $NH_2$ or $NH(C_1$–$C_6$ alkyl); and with the further proviso that $OR_{13}$ is not —O—($C_1$–$C_6$)alkyl;

$R_{12}$ is selected from the group consisting of hydrogen and a $C_1$–$C_6$ alkyl group; said $C_1$–$C_6$ alkyl group being optionally substituted with one or more groups selected from the group consisting of phenyl and $C_1$–$C_3$ alkyl;

each $R_{13}$ is selected from the group consisting of hydrogen, phenyl and a $C_1$–$C_6$ alkyl group; said $C_1$–$C_6$ alkyl group being optionally substituted with one or more groups selected from the group consisting of phenyl and $C_1$–$C_3$ alkyl; said phenyl being optionally substituted with one or more groups selected from the group consisting of halogen, methoxy, ethoxy, hydroxy, amino, and $C_1$–$C_6$ alkyl;

$X^-$ is selected from the group consisting of acetate, iodide, chloride, bromide, fluoride, hydroxide, sulfate, hydrogensulfate, methanesulfonate, trifluoromethanesulfonate, toluenesulfonate, benzenesulfonate, phosphate, hydrogenphosphate, dihydrogenphosphate, succinate, ascorbate, tartrate, gluconate, benzoate, malate, fumarate, and citrate;

with the proviso that when $R_1$–$R_4$, $R_6$–$R_9$ and $R_{11}$ are H, $R_5$ does not equal $CH_3$ or $CH_2CH_3$; and with the further proviso that the compound of Formula IV is not selected from the group consisting of:

5-methyl-10-benzyl-11-benzyloxycarbonylquindolinium iodide;

5,10-dimethyl-11-chloroquindolinium chloride; and 5,10-dimethyl-11-quindolinium dichloride.

3. The compound of claim 2 wherein $R_{10}$ is hydrogen.

4. A compound having the Formula VI

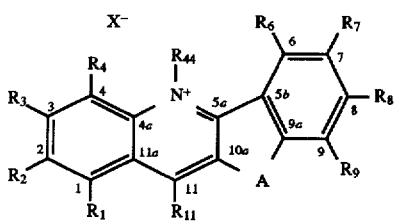

wherein:

$R_1$, $R_2$, $R_3$ and $R_4$ are independently selected from the group consisting of hydrogen, halogen, nitro, $SO_3H$, $COOR_{12}$, $OR_{13}$, $NHR_{13}$, phenyl, a $C_2$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl, $C_2$–$C_{10}$ alkenyl and $C_2$–$C_{10}$ alkynyl groups being optionally substituted with one or more groups selected from the group consisting of $C_1$–$C_6$ alkyl and phenyl;

$R_8$ and $R_9$ are independently selected from the group consisting of hydrogen, halogen, nitro, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and $C_2$–$C_{10}$ alkynyl groups being optionally substituted with one or more groups selected from the group consisting of $C_1$–$C_6$ alkyl and phenyl;

$R_6$ is selected from the group consisting of hydrogen, halogen, $SO_3H$, $COOR_{12}$, $OR_{13}$, $SR_{13}$, nitro, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl;

$R_7$ is selected from the group consisting of hydrogen, halogen, $SO_3H$, $COOR_{12}$, $OR_{13}$, $NHR_{13}$, $SR_{13}$, phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl group being optionally substituted with one or more groups selected from the group consisting of $C_1$–$C_6$ alkyl and phenyl; with the proviso that $NHR_{13}$ is not $NH_2$;

$R_{11}$ is selected from the group consisting of hydrogen, halogen, azide, cyano, $OR_{13}$, $NHR_{13}$, $SR_{13}$, phenyl, optionally substituted phenyl, a $C_1$–$C_{10}$ alkyl group, a $C_2$–$C_{10}$ alkenyl group and a $C_2$–$C_{10}$ alkynyl group; said phenyl being optionally substituted with one or more groups selected from the group consisting of halogen, amino, hydroxy, methoxy, ethoxy, $C_1$–$C_6$ alkyl, and phenyl; said $C_1$–$C_{10}$ alkyl group, $C_2$–$C_{10}$ alkenyl group and a $C_2$–$C_{10}$ alkynyl groups being optionally substituted with one or more groups selected from the group consisting of hydroxy, methoxy, ethoxy, mercapto, mercaptomethyl, cyano, $NH_2$, alkylammonium, dialkylammonium, trialkylammonium, $C_1$–$C_6$ alkyl and phenyl; with the proviso that $NHR_{13}$ is not $NH_2$ or $NH(C_1$–$C_6$ alkyl); with the further proviso that $OR_{13}$ is not —O—$(C_1$–$C_6)$alkyl; and with the still further proviso that when $R_{11}$ is halogen, $R_1$–$R_4$ and $R_6$–$R_9$ are not simultaneously hydrogen;

$R_{12}$ is selected from the group consisting of hydrogen and a $C_1$–$C_6$ alkyl group; said $C_1$–$C_6$ alkyl group being optionally substituted with one or more groups selected from the group consisting of phenyl and $C_1$–$C_3$ alkyl;

$R_{13}$ is selected from the group consisting of hydrogen, phenyl and a $C_1$–$C_6$ alkyl group; said $C_1$–$C_6$ alkyl group being optionally substituted with one or more groups selected from the group consisting of phenyl and $C_1$–$C_3$ alkyl; said phenyl being optionally substituted with one or more groups selected from the group consisting of halogen, methoxy, ethoxy, hydroxy, amino, and $C_1$–$C_3$ alkyl;

$X^-$ is selected from the group consisting of acetate, iodide, chloride, bromide, fluoride, hydroxide, sulfate, hydrogensulfate, methanesulfonate, trifluoromethanesulfonate, toluenesulfonate, benzenesulfonate, phosphate, hydrogenphosphate, dihydrogenphosphate, succinate, ascorbate, tartrate, gluconate, benzoate, malate, fumarate, and citrate;

$R_{44}$ is selected from the group consisting of oxygen, $C_1$–$C_{10}$ alkyl, $C_1$–$C_{10}$ alkenyl or $C_2$–$C_{10}$ alkynyl groups, $C_3$–$C_6$ cycloalkyl, and phenylmethyl; said $C_1$–$C_{10}$ alkyl, $C_2$–$C_{10}$ alkenyl and $C_2$–$C_{10}$ alkynyl groups being optionally substituted with one or more groups selected from the group consisting of halogen, amino, methylamino, dimethylamino, trimethylamino, hydroxy, methoxy, ethoxy, phenoxy, phenyl and $C_1$–$C_6$ alkyl; said $C_3$–$C_6$ cycloalkyl group being optionally substituted with one or more groups selected from the group consisting of halogen, phenyl, and $C_1$–$C_6$ alkyl; said phenylmethyl being optionally substituted with one or more groups selected from the group consisting of halogen, amino, dimethylamino, hydroxy, methoxy, ethoxy, $C_1$–$C_6$ alkyl, isopropyl, isobutyl, tert-butyl, and phenyl;

A is selected from the group consisting of O, S, $CH_2$, SO, or $SO_2$, with the proviso that when $R_1$–$R_4$ and $R_6$–$R_9$ are H, $R_{11}$ is a $C_1$ alkyl group, and $R_{44}$ is a $C_1$ alkyl group, A is not $CH_2$; and with the proviso that when $R_1$–$R_4$, $R_6$–$R_9$ and $R_{11}$ are H, $R_{44}$ is not oxygen.

5. A pharmaceutical composition useful for the treatment of diabetes mellitus when administered to warm-blooded animals, comprising a therapeutically effective amount of a compound of claim 1 and a pharmaceutically acceptable carrier or vehicle.

6. A pharmaceutical composition useful for the treatment of diabetes mellitus when administered to warm-blooded animals, comprising a therapeutically effective amount of a compound of claim 2 and a pharmaceutically acceptable carrier or vehicle.

7. A pharmaceutical composition useful for the treatment of diabetes mellitus when administered to warm-blooded animals, comprising a therapeutically effective amount of a compound of claim 3 and a pharmaceutically acceptable carrier or vehicle.

8. A pharmaceutical composition useful for the treatment of diabetes mellitus when administered to warm-blooded animals, comprising a therapeutically effective amount of a compound of claim 4 and a pharmaceutically acceptable carrier or vehicle.

9. A compound selected from the group consisting of:

5-Butylquindoline;
5,10-Dibenzylquindoline;
2-Fluoro-5-methyl-11-(phenoxy)quindoline;
2-Fluoro-5-methyl-11-(phenylamino)quindoline;
2-Fluoro-5-methyl-11-phenylquindolinium chloride;
2-Fluoro-5-methyl-11-((4-chlorophenyl) thio) quindoline);
6-Methoxy-5-methylquindoline;
7-Fluoro-11-iodo-5-methylquindoline;
9-Fluoro-11-iodo-5-methylquindoline;
11-Chloro-7-phenyl-5-methylquindoline;
6-Methoxy-5-methyl-10-acetylquindolinium iodide;
11-((4-Chlorophenyl)thio)-5-methylbenzofuro(3, 2-b) quinolinium chloride;
11-((4-Chlorophenyl)thio)-5-methylindeno(1, 2-b) quinolinium chloride; or pharmaceutically acceptable salts thereof.

10. The compound of claim 1 selected from the group consisting of:

2-Fluoro-5-methyl-11-chloroquindoline;
2-Chloro-5-methyl-11-chloroquindoline;
1-Chloro-5-methyl-11-chloroquindoline;
2-Fluoro-5-methylquindoline;
7-Bromo-8-chloro-5-methylquindoline;
7-Bromo-6-chloro-5-methylquindoline;
7-Fluoro-11-chloro-5-methylquindoline;
11-Chloro-6-fluoro-5-methylquindoline;
11-Chloro-8-fluoro-5-methylquindoline;
11-Chloro-9-fluoro-5-methylquindoline;
9-Fluoro-11-chloro-5-methylquindoline;
4,11-Dichloro-5-methylquindoline; and pharmaceutically acceptable salts thereof.

11. A compound selected from the group consisting of:

5-Butylquindolinium hydrochloride;
5-Butylquindolinium hydroiodide;
5,10-Dibenzylquindolinium chloride;
5,10-Dibenzylquindolinium bromide;
2-Fluoro-5-methyl-11-chloroquindolinium hydrotrifluoromethanesulfonate;
2-Fluoro-5-methyl-11-chloroquindolinium hydrochloride;
2-Fluoro-5-methyl-11-(phenoxy)quindolinium hydrochloride;
2-Fluoro-5-methyl-11-(phenylamino)quindolinium hydrochloride;
2-Fluoro-5-methyl-11-phenylquindolinium hydrochloride;
2-Fluoro-5-methyl-11-((4-chlorophenyl)thio) quindolinium hydrochloride;
6-Methoxy-5-methylquindolinium hydrochloride;
2-Chloro-5-methyl-11-chloroquindolinium hydrotrifluoromethanesulfonate;
2-Chloro-5-methyl-11-chloroquindolinium hydrochloride;
1-Chloro-5-methyl-11-chloroquindolinium hydrotrifluoromethanesulfonate;
1-Chloro-5-methyl-11-chloroquindolinium hydrochloride;
2-Fluoro-5-methylquindolinium hydroiodide;
2-Fluoro-5-methylquindolinium hydrochloride;
7-Bromo-8-chloro-5-methylquindolinium hydroiodide;
7-Bromo-8-chloro-5-methylquindolinium hydrochloride;
7-Fluoro-11-iodo-5-methylquindolinium hydroiodide;
7-Fluoro-11-iodo-5-methylquindolinium hydrochloride;
7-Fluoro-11-chloro-5-methylquindolinium; hydroiodide;
7-Fluoro-11-chloro-5-methylquindolinium hydrochloride;
11-Chloro-6-fluoro-5-methylquindolinium hydrotrifluoromethanesulfonate;
11-Chloro-6-fluoro-5-methylquindolinium hydrochloride;
11-Chloro-8-fluoro-5-methylquindolinium hydrotrifluoromethanesulfonate;
11-Chloro-8-fluoro-5-methylquindolinium hydrochloride;
9-Fluoro-11-iodo-5-methylquindolinium hydroiodide;
9-Fluoro-11-iodo-5-methylquindolinium hydrochloride;
9-Fluoro-11-chloro-5-methylquindolinium hydroiodide;
9-Fluoro-11-chloro-5-methylquindolinium hydrochloride;
11-Chloro-7-phenyl-5-methylquindolinium hydrotrifluoromethanesulfonate;
11-Chloro-7-phenyl-5-methylquindolinium hydrochloride;
4,11-Dichloro-5-methylquindolinium hydrotrifluoromethanesulfonate; and
4,11-Dichloro-5-methylquindolinium chloride.

12. A pharmaceutical composition useful for the treatment of diabetes mellitus when administered to warm-blooded animals, comprising a therapeutically effective amount of a compound of claim 10 and a pharmaceutically acceptable carrier or vehicle.

13. A pharmaceutical composition useful for the treatment of diabetes mellitus when administered to warm-blooded animals, comprising a therapeutically effective amount of a compound of claim 11 and a pharmaceutically acceptable carrier or vehicle.

* * * * *